(12) United States Patent
Pearce et al.

(10) Patent No.: US 11,364,226 B2
(45) Date of Patent: *Jun. 21, 2022

(54) DEUTERATED DOMPERIDONE COMPOSITIONS, METHODS, AND PREPARATION

(71) Applicant: CinRx Pharma, LLC, Cincinnati, OH (US)

(72) Inventors: Catherine Pearce, Montgomery, OH (US); Jon Isaacsohn, Cincinnati, OH (US); Piyush Patel, Garnet Valley, PA (US)

(73) Assignee: CinRx Pharma, LLC, Cincinnati, OH (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/621,107

(22) PCT Filed: Jun. 28, 2018

(86) PCT No.: PCT/US2018/039928
§ 371 (c)(1),
(2) Date: Dec. 10, 2019

(87) PCT Pub. No.: WO2019/006078
PCT Pub. Date: Jan. 3, 2019

(65) Prior Publication Data
US 2021/0137892 A1     May 13, 2021

Related U.S. Application Data

(63) Continuation-in-part of application No. 15/639,431, filed on Jun. 30, 2017, now Pat. No. 10,266,516.

(51) Int. Cl.
*A61K 31/4184* (2006.01)
*A61K 31/454* (2006.01)

(52) U.S. Cl.
CPC ........ *A61K 31/4184* (2013.01); *A61K 31/454* (2013.01)

(58) Field of Classification Search
None
See application file for complete search history.

(56) References Cited

U.S. PATENT DOCUMENTS

| | | | |
|---|---|---|---|
| 4,066,772 A | 1/1978 | Vandenberk et al. |
| 5,652,246 A | 7/1997 | Nanteuil et al. |
| 5,814,339 A | 9/1998 | Prudhoe |
| 6,126,969 A | 10/2000 | Shah et al. |
| 8,211,465 B2 | 7/2012 | Lee et al. |
| 8,679,544 B2 | 3/2014 | Dodd et al. |
| 8,734,847 B2 | 5/2014 | Dodd et al. |
| 8,735,450 B2 | 5/2014 | Dodd et al. |
| 8,808,751 B2 | 8/2014 | Cammarano et al. |
| 8,992,982 B2 | 3/2015 | Dodd et al. |
| 8,999,387 B2 | 4/2015 | Dodd et al. |
| 9,017,721 B2 | 4/2015 | Dodd et al. |
| 9,089,471 B2 | 7/2015 | Dodd et al. |
| 9,095,496 B2 | 8/2015 | Dodd et al. |
| 9,107,827 B2 | 8/2015 | Hovey et al. |
| 9,173,854 B2 | 11/2015 | Dodd et al. |
| 9,180,096 B2 | 11/2015 | Dodd et al. |
| 9,186,328 B2 | 11/2015 | Dodd et al. |
| 9,249,149 B2 | 2/2016 | Silverman et al. |
| 2005/0095295 A1 | 5/2005 | Maggi et al. |
| 2005/0106247 A1 | 5/2005 | Venkatesh et al. |
| 2007/0264323 A1 | 11/2007 | Shojaei et al. |
| 2009/0028929 A1 | 1/2009 | Stefanelli et al. |
| 2009/0028948 A1 | 1/2009 | Payne et al. |
| 2009/0076010 A1 | 3/2009 | Czarnik |
| 2009/0131485 A1 | 5/2009 | Liu et al. |
| 2010/0092563 A1 | 4/2010 | Raffaele et al. |
| 2010/0113405 A1 | 5/2010 | Gant et al. |
| 2010/0255096 A1 | 10/2010 | Aronchick |
| 2011/0160253 A1 | 6/2011 | Harbeson |
| 2012/0135048 A1 | 5/2012 | Dodd et al. |
| 2013/0209569 A1 | 8/2013 | Dodd et al. |
| 2013/0220526 A1 | 8/2013 | Yang et al. |
| 2013/0243854 A1 | 9/2013 | Dodd et al. |
| 2013/0333831 A1 | 12/2013 | Yang et al. |
| 2013/0345188 A1 | 12/2013 | Steiner et al. |
| 2014/0017299 A1 | 1/2014 | Dadey et al. |
| 2014/0070440 A1 | 3/2014 | Yang et al. |
| 2014/0163060 A1 | 6/2014 | Yang et al. |
| 2014/0194487 A1 | 7/2014 | Dodd et al. |
| 2014/0200276 A1 | 7/2014 | Dodd et al. |
| 2014/0220121 A1 | 8/2014 | Dodd et al. |
| 2014/0248359 A1 | 9/2014 | Dodd et al. |
| 2014/0255494 A1 | 9/2014 | Dodd et al. |
| 2014/0256781 A1 | 9/2014 | Dodd et al. |

(Continued)

FOREIGN PATENT DOCUMENTS

| CN | 1810805 A | 8/2006 |
|---|---|---|
| EA | 201891727 A1 | 12/2018 |

(Continued)

OTHER PUBLICATIONS

Toronto Research Chemicals Inc.; Safety Data Sheet—Version 5.0; Catalogue No. D531102; Apr. 2017; 6 pages.
Motilium Janssen-Ortho: "Motilium (Domperidone)", Jan. 1, 2015 (Jan. 1, 2015), pp. 1-3, XP55681442, Retrieved from the Internet: URL:https://www.rxmed.com/b.main/b2.pharmaceutical/b2.1.monographs/cps-_monographs/CPS-_(General_Monographs_M)/MOTILIUM.html [retrieved on Mar. 31, 2020], cited on p. 4.
Wako Organic Square; Sep. 2010; No. 33; p. 2-3 (contains English Translation).

(Continued)

*Primary Examiner* — Heidi Reese
(74) *Attorney, Agent, or Firm* — BakerHostetler

(57) ABSTRACT

Deuterated domperidone compositions, methods of synthesis, methods of use, and dosing formulations providing beneficial safety and other effects.

19 Claims, 9 Drawing Sheets

(56) References Cited

U.S. PATENT DOCUMENTS

| | | |
|---|---|---|
| 2014/0271787 A1 | 9/2014 | Bogue et al. |
| 2014/0271788 A1 | 9/2014 | Myers et al. |
| 2014/0272220 A1 | 9/2014 | Bogue et al. |
| 2014/0287039 A1 | 9/2014 | Bosch et al. |
| 2014/0288101 A1 | 9/2014 | DeWitt |
| 2014/0302127 A1 | 10/2014 | Dodd et al. |
| 2014/0326812 A1 | 11/2014 | Dodd et al. |
| 2015/0018782 A1 | 1/2015 | Hiraoka et al. |
| 2017/0298046 A1 | 10/2017 | Soldano et al. |

FOREIGN PATENT DOCUMENTS

| | | |
|---|---|---|
| JP | 52-017475 A | 2/1977 |
| JP | 2015-521621 A | 7/2015 |
| WO | WO 2004/030658 A1 | 4/2004 |
| WO | WO 2008/134540 A1 | 11/2008 |
| WO | 2010/054158 A2 | 5/2010 |
| WO | 2013/192097 A1 | 12/2013 |
| WO | WO 2017/136617 A1 | 8/2017 |

OTHER PUBLICATIONS

"Stable Isotopes in Pharmaceutical Research", vol. 26, Chapter 2, pp. 13-18, published 1997 and edited by Thomas R. Browne, M.D., referred to hereafter as "Browne".

International Patent Application No. PCT/US2018/039928; Invitation to Pay Add'l Fees; dated Oct. 1, 2018; 13 pages.

E.W-X. Wan et al.; "Dose-effect study of domperidone as galactagogue in preterm mothers with insufficient milk supply, and its transfer into milk"; British Journal of Clinical Pharmacology, 66:2, pp. 283-289 (May 27, 2008).

The Economist; "Drugs that live long will prosper"; (http://www.economist.com/news/science-and-technology/21663193-simple-change-some-pharmaceuticals-might-boost-their-efficacy-and-make-few); Science and Technology, 4 pages (Sep. 5, 2015).

Gaba et al.; "Nanostructured lipid (NLCs) carriers as a bioavailability enhancement tool for oral administration"; Drug Delivery, vol. 22, pp. 691-700 (Mar. 27, 2014).

Manivannan; "Oral disintegrating tablets: A future compaction"; Drug Invention Today, vol. 1, pp. 61-65 (Nov. 1, 2009).

Mulatero; "Domperidone"; (http://flipperdiff.org/apppathwaysaccount/items/6886); 7 pages (Jun. 16, 2014).

Synfine Research; "New Product Information", (http://synfine.com/pdfs/New_Product_Bulletin_November_26_2009.pdf); 1 page (Nov. 26, 2009).

PCT. International Search Report and Written Opinion, Patent Application No. PCT/US2017/016334, 13 pages (dated Apr. 28, 2017).

Yang et al.; "A Facile Route of Synthesis for Making Flibanserin"; Organic Process Research and Development; Aug. 2016; vol. 20 No. 9; p. 1576-1580.

International Patent Application No. PCT/US2018/039928; Int'l Search Report and the Written Opinion; dated Dec. 21, 2018; 21 pages.

European Search Report dated Jul. 5, 2019 for EP application No. 17748198.3; 5 pages.

"Gastroparesis"; About Motility; https://www.aboutgimotility.org/disorders-of-the-stomach/gastroparesis.html; Mar. 22017; accessed May 5, 2019; 5 pages.

Gant, Thomas G. "Using Deuterium in Drug Discovery: Leaving the Label in the Drug" Journal of Medicinal Chemistry; vol. 57; 2014; p. 3595-3611.

Brogden et al.; "Domperidone: A Review of its Pharmacological Activity, Pharmacokinetics and Therapeutic Efficacy in the Symptomatic Treatment of Chronic Dyspepsia and as an Antiemetic"; Drugs; vol. 24; 1982; p. 360-400.

Reddymasu et al.; "Domperidone: Review of Pharmacology and Clinical Applications in Gastroenterology"; American Journal of Gastroenterology; vol. 102(9); 2007; p. 2036-2045.

Timmins et al.; "Deuterated drugs; where are we now?"; Expert Opinion Ther Pat; vol. 24(10); Oct. 2014; p. 1067-1075.

Michaud et al.; "An improved HPLC assay with fluorescence detection for the determination of domperidone and three major metabolites for application in vitro drug metabolism studies"; Journal of Chromatography B; vol. 852; 2007; p. 611-616.

Youssef et al.; Identification of domperidone metabolites in plasma and urine of gastroparesis patients with LC-ESI-MS/MS; Xenobiotica; vol. 43(12); 2013; p. 1073-1083.

McLaughlin et al.; Orally Disintegrating Tablets: The Effect of Recent FDA Guidance on ODT Technologies and Applications; Pharmaceutical Technology; Sep. 2009; 6 pages.

Shukla et al.; "Mouth Dissolving Tablets I: An Overview of Formulation Technology"; Scientia Pharmaceutica; vol. 76; 2009; p. 309-326.

Pathan et al.; "Chemical Penetration Enhancers for Transdermal Drug Delivery Systems"; Tropical Journal of Pharmaceutical Research; vol. 8(2); Apr. 2009; p. 173-179.

"Gastroparesis"; International Foundation for Functional Gastrointestinal Disorders; http://www.aboutgimotility.org/site/about-gi-motility/disorders-of-the-stomach/gastroparesis; 2015; accessed Nov. 9, 2015; 3 pages.

Agrawal et al.; "Formulation development and evaluation of in situ nasal gel of poorly water soluble drug using mixed solvency concept"; Asian Journal of Pharmaceutics; 2011; p. 131-140.

Basu, Desai P.; "Design and Evaluation of Fast Dissolving Film of Domperidone"; Int'l Research Journal of Pharmacy; vol. 3(9); 2012; p. 134-145.

Blanes et al.; "Comparative Study "in vitro" of transdermal absorption of a series of antiemetic drugs"; Eur J Drug Metab Pharmacokinet; vol. 3; Jan. 1991; p. 410-414 (only English Abstract).

Buckles et al.; "The Treatment of Gastroparesis in the Age of the Gastric Pacemaker: A Review"; MedGenMed: Medscape General Medicine; vol. 5(4); Oct. 2003; 14 pages.

"Domperidone 10mg Film-Coated Tablets"; https://www.medicines.org.uk/emc/print-document?documentId=18865; accessed Dec. 3, 2015; 7 pages.

"PRAC recommends restricting use of domperidone"; European Medicines Agency; Mar. 2014; 3 pages.

Harbeson et al.; "Deuterium Medicinal Chemistry: A New Approach to Drug Discovery and Development"; MedChem; No. 2; May 2014; p. 8-22.

Helmy et al.; "Pharmacokinetics and comparative bioavailability of domperidone suspension and tablet formulations in healthy adult subjects"; Clinical Pharmacology in Drug Development; vol. 3 Issue 2; 2014; p. 126-131 (only Abstract).

"MOTILIUM@ 10mg Tablets"; Product Information; Janssen; 2014; 11 pages.

"MOTILIUM@—The comprehensive resource for physicians, drug and illness information"; http://www.rxmed.com/b.main/b2.pharmaceutical/b2.1.monographs/CPS-%20Monographs; RxMed; accessed Dec. 3, 2015; 5 pages.

Khan et al.; "Characterization and Ex-Vivo Skin Permeation Study of Domperidone Maleate Transdermal Patch"; Bulletin of Pharmaceutical Research; vol. 2(1); 2012; p. 15-21.

Koland et al.; "Fast Dissolving Sublingual Films of Ondansetron Hydrochloride: Effect of Additives on in vitro Drug Release and Mucosal Permeation"; J. Young Pharm.; vol. 2(3); 2010; p. 216-222.

Madishetti et al.; "Development of domperidone bilayered matrix type transdermal patches: physicochemical, in vitro and ex vivo characterization"; DARU Journal of Pharmaceutical Sciences.; vol. 18(3); 2010; p. 221-229.

Ng et al.; "Validation of a Static Franz Diffusion Cell System for In Vitro Permeation Studies"; AAPS PharmSciTech; vol. 11(3); Sep. 2010; p. 1432-1441.

Prabhu et al.; "Formulation development and investigation of domperidone transdermal patches"; Int'l Journal of Pharmaceutical Investigation; vol. 1(4); 2011; p. 240-246.

"Product Pipeline"; http://www.concertpharma.com/product-pipeline/; © 2016; 4 pages.

(56) References Cited

OTHER PUBLICATIONS

Scavone et al.; "Hyperprolactinemia induced by long-term domperidone treatment does not alter the sensitivity of striatal dopamine receptors"; Braz J Med Bio Res; vol. 24(6); 1991; p. 591-594 (only Abstract).

Riviere et al.; "The Isolated Perfused Porcine Skin Flap (IPPSF): I. A Novel in Vitro Model for Percutaneous Absorption and Cutaneous Toxicology Studies"; Toxicological Sciences; vol. 7; Oct. 1986; p. 444-453.

Bronaugh et al.; "Methods for In Vitro Percutaneous Absorption Studies IV: the Flow-Through Diffusion Cell"; Journal of Pharmaceutical Sciences; vol. 74; Jan. 1985; p. 64-67.

Patra et al.; Osmotic Drug Delivery Systems: Basis and Design Approaches; Recent Patents on Drug Delivery and Formulations; vol. 7; 2013; 12 pages.

Lehr et al.; "In vitro evaluation of mucoadhesive properties of chitosan and some other natural polymers"; Int'l Journal of Pharmaceutics; vol. 78; Jan. 1992; p. 43-48.

Borchard et al.; "The potential of mucoadhesive polymers in enhancing intestinal peptide drug absorption. III: Effects of chitosan-glutamate and carbomer on epithelial tight junctions in vitro"; Journal of Controlled Release; vol. 39; May 1996; p. 131-138.

Artursson et al.; "Effect of Chitosan on the Permeability of Monolayers of Intestinal Epithelial Cells (Caco-2)"; Pharmaceutical Research; vol. 11; Sep. 1994; p. 1358-1361.

Schipper et al.; "Chitosans as Absorption Enhancers for Poorly Absorbable Drugs. 1: Influence of Molecular Weight and Degree of Acetylation on Drug Transport Across Human Intestinal Epithelial (Caco-2) Cells"; Pharmaceutical Research; vol. 13; Nov. 1996; p. 1686-1692.

Luessen et al.; "N-Trimethyl Chitosan Chloride as a Potential Absorption Enhancer Across Mucosal Surfaces: In Vitro Evaluation in Intestinal Epithelial Cells (Caco-2)"; Pharmaceutical Research; vol. 14; Sep. 1997; p. 1197-1202 (abstract only).

James L. Madara; "Loosening Tight Junctions"; J Clin. Invest.; vol. 83; Apr. 1989; p. 1089-1094.

Meza et al.; "Occluding Junctions in MDCK Cells: Modulation of Transepithelial Permeability by the Cytoskeleton"; Journal of Cellular Biochemistry; vol. 18; 1982; p. 407-421.

J. L. Madara; "Intestinal absorptive cell tight junctions are linked to cytoskeleton"; Cell Physiology; vol. 253; Jul. 1987; p. C171-C175.

Schipper et al.; "Chitosans as Absorption Enhancers for Poorly Absorbable Drugs 2: Mechanism of Absorption Enhancement"; Pharmaceutical Research; vol. 14; Jul. 1997; p. 923-929.

CAS# 1329614-18-7; Sep. 2011; Abinter SARL.

TCI; No. 156(1); 2013; p. 2-5 (contains English Translation).

| 10 mg/kg, Oral | Domperidone | Compound 2 ($d_4$) | Compound 6 ($d_6$) |
|---|---|---|---|
| $C_{max}$, ng/mL | 340 ± 51 | 254 ± 31 | 429 ± 21 |
| $t_{max}$, h | 0.7 ± 0.3 | 2 ± 0 | 2 ± 0 |
| $AUC_{0-t}$, ng*h/mL | 1732 ± 238 | 2042 ± 422 | 2291 ± 469 |
| $AUC_{0-\infty}$, ng*h/mL | 1482 ± 211 | 1456 ± 301 | 1633 ± 335 |
| $t_{1/2}$, h | 3.6 ± 0.6 | 3 ± 0.1 | 3.6 ± 0.3 |
| Mean ± SD, n=3 | Dose normalized to 10 mg/kg | | |

FIG. 1B

DEUTERATED DOMPERIDONE COMPOSITIONS, METHODS, AND PREPARATION

CROSS-REFERENCE TO RELATED APPLICATIONS

This application is a U.S. national phase application under 35 U.S.C. 371 of International Patent Application No. PCT/US2018/039928, filed on Jun. 28, 2018, which is a continuation-in-part of U.S. patent application Ser. No. 15/639,431, filed Jun. 30, 2017, granted as U.S. Pat. No. 10,266,516 on Apr. 23, 2019, the disclosures of which are incorporated by reference in their entireties.

BACKGROUND

Gastroparesis (GP) is a condition in which the motility of the stomach does not function or does not function properly, which prevents the stomach from emptying and interferes with digestion.

GP may be caused by damage to the vagus nerve, which regulates digestive processes. Damage to the vagus nerve can be caused by diseases, such as type I or type II diabetes, or by stomach or small intestine surgery, and can limit the ability of the nervous system to send signals to the stomach muscles. Viral infections, certain medications, certain cancer treatments, scleroderma, nervous system disorders such as Parkinson's disease or multiple sclerosis, or hypothyroidism may also lead to or result in GP.

Diagnosis of GP is typically by upper gastrointestinal (GI) endoscopy, computerized tomography (CT), enterography, magnetic resonance enterography, upper GI series (x-ray), gastric emptying study, and/or a breath test. Symptoms of GP include nausea, vomiting, blood glucose alterations, abdominal pain, bloating, feelings of fullness after only a few bites, lack of appetite, weight loss, and malnutrition. Untreated GP can lead to severe dehydration, malnutrition, hardening of undigested food in the stomach (bezoar), and erratic alternations in blood glucose that can exacerbate diabetes.

Treatment of GP involves identifying and treating the underlying pathology. GP arising from diabetes may be treated by dietary alterations. GP may be treated with medications to stimulate the stomach muscles, e.g., metoclopramide, erythromycin, and cisapride. Metoclopramide poses serious side effects, such as development of movement disorders or adverse interactions with other medications; erythromycin is susceptible to loss of efficacy as patient drug tolerance increases; and cisapride has limited accessibility. Medications to control nausea and vomiting include prochlorperazine, thiethylperazine, diphenhydramine, and ondansetron.

The symptoms of GP may be treated surgically, such as jejunostomy tube placement in the small intestine or gastric venting tube installation. For severe cases, a feeding tube may be inserted orally or nasally for direct placement into the small intestine, or administered parenterally.

Domperidone is an effective dopamine antagonist that does not readily cross the blood-brain barrier; as such, domperidone exhibits only minimal extrapyramidal side effects. Domperidone exhibits both gastrokinetic and antiemetic activity, and exerts its gastrokinetic action by acting on the peripheral dopamine receptors in the stomach. Domperidone acts as a peripherally selective antagonist of the dopamine D2 and D3 receptors, and acts to block the dopamine receptors that register nausea. Domperidone can block dopamine receptors in the pyloric antrum and duodenum to increase motility in the upper GI tracts. Domperidone can also block dopamine receptors in the pituitary gland, which can increase the release of prolactin leading to increased lactation, so is used to treat insufficient lactation. Domperidone has been evaluated for use in treating nausea and vomiting, gastroparesis, Parkinson's disease, functional dyspepsia, insufficient lactation, pediatric reflux, gastroesophageal reflux disease, and other GI motility disorders or conditions.

SUMMARY

In some embodiments, the present disclosure provides therapeutic methods to ameliorate any of all of gastroparesis, nausea as a disorder separated from or associated with gastroparesis, vomiting as a disorder separate from or associated with gastroparesis, gastroesophageal reflux disease (GERD), functional dyspepsia, nausea and vomiting associated with chemotherapy, and/or lactation insufficiency, by administering domperidone deuterated with four (4) deuteriums in the unchlorinated aromatic ring ($d_4$) or six (6) deuteriums in the linking propyl group ($d_6$). In one embodiment, domperidone-$d_4$ is administered and is preferred over domperidone-$d_6$.

In further embodiments, the present disclosure provides methods for ameliorating gastroesophageal reflux disease, functional dyspepsia, or nausea and vomiting associated with chemotherapy, in a patient, comprising administering a therapeutically effective amount of a compound that is $d_2$-domperidone 4, $d_4$-domperidone 2, $d_6$-domperidone 3, or $d_{10}$-domperidone 5, or a pharmaceutically acceptable salt thereof to the patient:

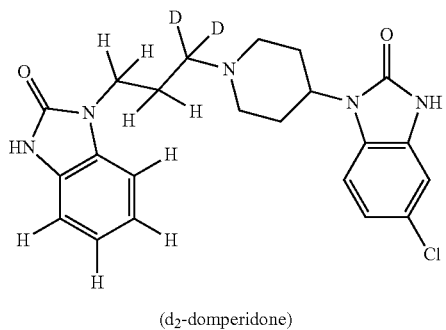

($d_2$-domperidone)

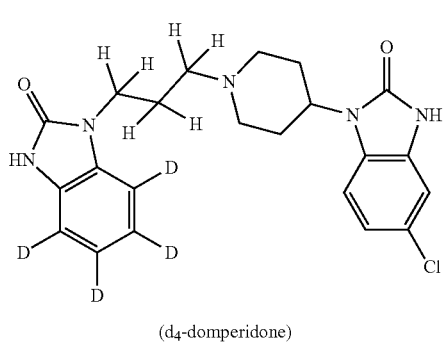

($d_4$-domperidone)

-continued

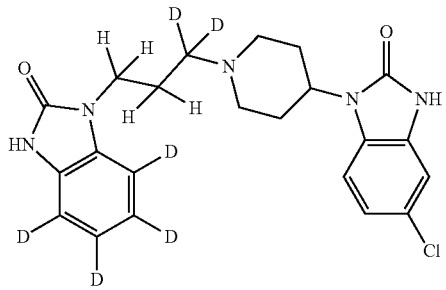

(d₆-domperidone)

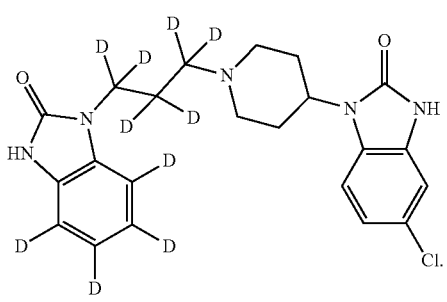

(d₁₀-domperidone)

In some aspects, the compound is d₄-domperidone.

In other embodiments, the present disclosure provides methods of preparing deuterated domperidone. In some aspects, the methods include reacting 1,2-diaminobenzene having 0-4 deuteriums with a reactive carbonyl species to produce a cyclic imide, reacting the cyclic imide with a protecting group to produce a monoprotected cyclic imide, reacting the monoprotected cyclic imide with a 1,3-bifunctional propyl derivative having 0-6 deuteriums to produce an intermediate, reacting the intermediate with 5-chloro-1-(4-piperidinyl)-1,3-dihydro-2H-benzimidazol-2-one, and removing the protecting group either before or after reacting the intermediate with the 5-chloro-1-(4-piperidinyl)-1,3-dihydro-2H-benzimidazol-2-one.

In yet further embodiments, the present disclosure provides a compound that is of formula 16, wherein R=H or D:

16

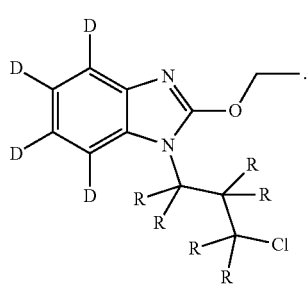 [SMILES: [2H]c1c([2H])c([2H])c2c(nc(OCC)n2C([2H])([2H])C([2H])([2H])C([2H])([2H])Cl)c1[2H]]

In still other embodiments, the present disclosure provides a compound that is 1-(3-chloropropyl-1,1,2,2,3,3-d₆)-4,5,6,7-tetradeutero-2-ethoxy-benzimidazole:

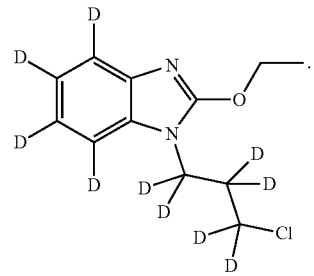

In further embodiments, the present disclosure provides a compound that is

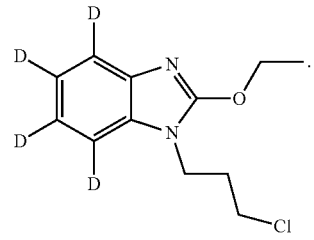 [SMILES: [2H]c1c([2H])c([2H])c2c(nc(OCC)n2CCCCl)c1[2H]]

BRIEF DESCRIPTION OF THE FIGURES

FIGS. 1A-1B show a plasma profile of orally administered domperidone and deuterated domperidone (FIG. 1A) and an analysis of the data shown in FIG. 1A (FIG. 1B).

DETAILED DESCRIPTION

Figure 1A:
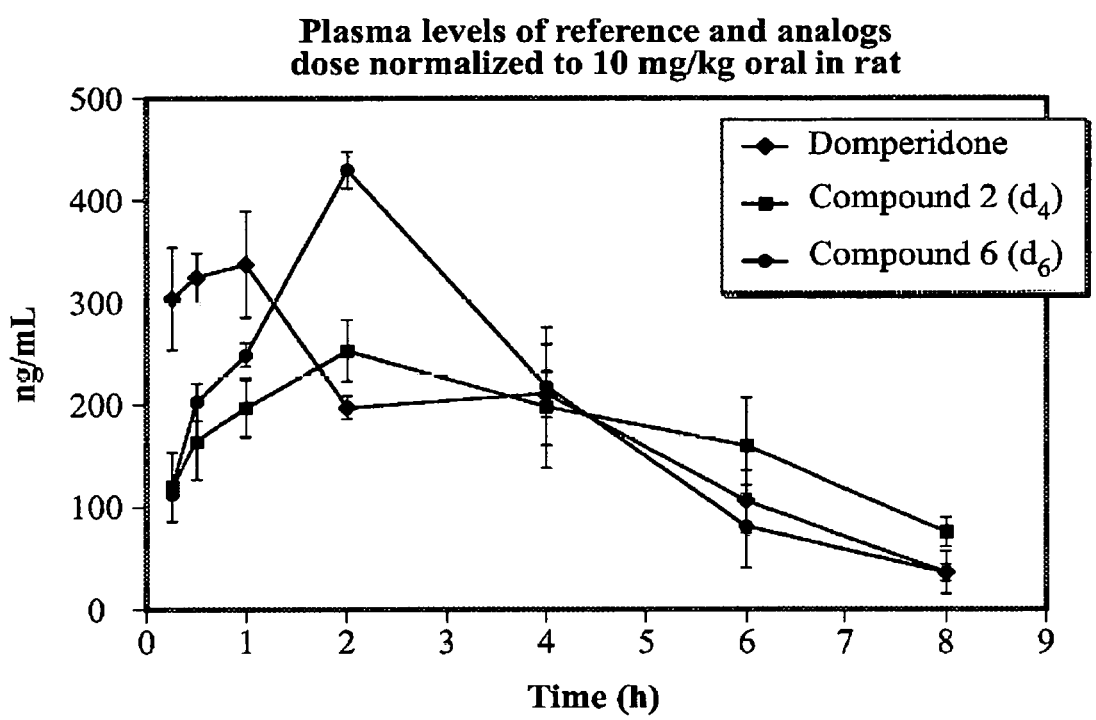

In the disclosure, the singular forms "a,", "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude an optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

If not specified herein, percentages refer to weight/volume.

The terms "subject" and "patient" are used interchangeably and typically refer to mammals. In some embodiments, the patient or subject is a human. In other embodiments, the patient or subject is a veterinary or farm animal, a domestic animal or pet, or animal used for conducting clinical research.

"Ameliorating" or variations thereof refers eliminating or reducing the development of a disease or disorder, i.e., delaying the onset of the disease. In other embodiments, "treating" refers to eliminating or reducing at least one physical parameter of the disease or disorder.

"Domperidone" has referenced herein refers to 5-chloro-1-(1-[3-(2-oxo-2,3-dihydro-1H-benzo[d]imidazol-1-yl)propyl]piperidin-4-yl)-1H-benzo[d]imidazol-2(3H)-one, which has the following structure:

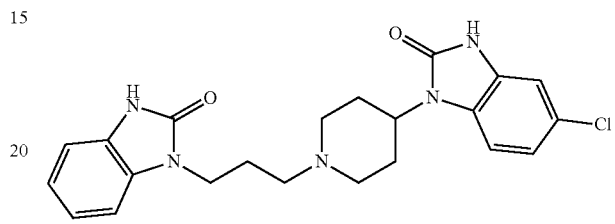

Any reference to domperidone also includes pharmaceutically acceptable salts, esters, hydrates, solvates, prodrug forms, and derivatives of these, which is broadly defined as domperidone compounds that are modified or partially substituted, examples include but are not limited to adding a single atom, adding a reactive group, adding a functional group, forming a dimer or multimer, conjugating to another molecule such as an antibody, etc.

"Pharmaceutically acceptable" refers to properties and/or substances that are acceptable to the patient from a pharmacological/toxicological vantage, and to the manufacturing pharmaceutical chemist from a physical/chemical vantage regarding composition, formulation, stability, patient acceptance, and bioavailability.

A pharmaceutically acceptable salt includes salts with a pharmaceutically acceptable acid or base, e.g., inorganic acids, e.g., hydrochloric, sulfuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal, e.g. sodium or potassium, and alkali earth metal, e.g. calcium or magnesium, hydroxides, and organic bases, e.g., alkyl amines, arylalkyl amines and heterocyclic amines.

The abbreviation "D," as used herein, refers to a stable isotope of hydrogen that is deuterium (heavy hydrogen or $^2$H). Such instances of "D" include an amount of deuterium that is above the naturally occurring distribution of deuterium. In some embodiments, D has deuterium enrichment of no less than about 1%. In other embodiments, D has a deuterium enrichment of no less than about 5%. In further embodiments, D has a deuterium enrichment of no less than about 10%. In still other embodiments, D has a deuterium enrichment of no less than about 20%. In still other embodiments, D has a deuterium enrichment of no less than about 30%. In still other embodiments, D has a deuterium enrichment of no less than about 40%. In yet further embodiments, D has a deuterium enrichment of no less than about 50%. In still other embodiments, D has a deuterium enrichment of no less than about 60%. In other embodiments, D has a deuterium enrichment of no less than about 70%. In further embodiments, D has a deuterium enrichment of no less than about 80%. In yet other embodiments, D has a deuterium enrichment of no less than about 90%. In still further embodiments, D has a deuterium enrichment of no less than about 98% of deuterium. In still further embodiments, D has a deuterium enrichment of no less than about 99% of deuterium. In still further embodiments, D has a deuterium enrichment of at least 99% of deuterium.

Like all drugs, the safety of domperidone is dependent upon its metabolism. A decreased metabolism renders a drug to have a longer residence time in the body. Doses of domperidone required to treat gastroparesis, i.e., 10 mg administered three times a day for a total of 30 mg, and up to 60 mg, can result in cardiac QT prolongation, which is dose related. Because of this effect, it is not approved for this indication in the United States, but is approved in Europe and Canada.

Domperidone is extensively metabolized; its major metabolic pathways produce a 5-hydroxy form, an N-dealkylated form, and a hydroxylated form. Methods that decrease domperidone metabolism would thus permit a lower dose to be administered to achieve the same degree of efficacy in a patient, decreasing or eliminating the cardiac effect, and/or decreasing the number of doses required to be administered, and/or providing more consistent exposure that could enhance patient tolerance or efficacy.

Overall peak plasma levels of domperidone depend on its route of administration. Intramuscular (IM) and oral administration in a fasting individual resulted in peak plasma levels at 10 min and 30 min post administration; suppository administration resulted in peak plasma levels at 1-2 hr post administration. Plasma concentrations were lower two hours after oral versus IM administration, likely due to hepatic first pass and gut wall metabolism. Peak plasma concentration was 40 ng/ml after 10 mg IM injection, 20 ng/ml after oral ingestion of a 10 mg tablet, and 70-100 ng/ml oral ingestion of a 60 mg tablet or drops. Human plasma protein binding of 10 and 100 ng/ml tritiated domperidone was 91.7% and 93.0% respectively. Bioavailability was relatively high at 90% after IM injection, and relatively low at 13%-17% after oral administration, even further decreased by antacid use because of increased stomach pH. RxMed: Pharmaceutical Information—MOTILIUM®, Janssen-Ortho, Domperidone Maleate.

Compared to the tritiated spiperone, the classic ligand used in central nervous system (CNS) models, domperidone binds selectively and specifically to striatal dopamine receptors. However, intravenous (IV) domperidone administration, even at high doses, does not displace labeled spiperone in animal brain models because of its poor penetration of the blood-brain barrier (Reddymasu et al., Am. J. Gastroenterology). Domperidone also has a high affinity for GI tissue; high concentrations are found in the esophagus, stomach, and small intestine. Domperidone blocks dopaminergic inhibition of GI transit. It is rapidly metabolized by the liver; after oral administration, 32% is excreted in urine and 66% is excreted in feces. Elimination half-life is 7.5 hr in individuals that are healthy, and about three times longer in individuals with renal dysfunction.

The efficacy of domperidone is based on its ability to increase the amplitude of esophageal motor function, enhance antral-duodenal contractions, and better coordinate peristalsis across the pylorus with subsequent acceleration of gastric emptying. Domperidone has effective antiemetic activity at the chemoreceptor trigger zone (CTZ) in the fourth ventricle of the brain but outside the blood-brain barrier. It has no cholinergic activity and is not inhibited by atropine.

Domperidone modulates gastric emptying of both solids and liquids, and does not alter gastric acid secretion, secretory volume, intragastric pH, or serum gastrin concentration.

At doses ranging from 10 mg to 30 mg orally, four times daily at one-half hour prior to meals and at bedtime, domperidone significantly reduced gastrointestinal symptoms and hospitalizations from gastroparesis, had a positive effect on the central control of vomiting and nausea, and accelerated emptying of a solid meal (Buckels et al., Medscape General Medicine. 2003; 5(4) www.medscape.com).

One method to decrease domperidone metabolism is to administer a deuterated form of domperidone. Domperidone is extensively metabolized. Deuteration slows metabolism at key sites and routes of metabolism, producing higher efficacy with a lower dose. A deuterated form of a small molecule increases its retention and thus decreases its metabolism, permitting a lower dose to be administered while achieving the same efficacy as the higher dose without cardiac symptoms.

Deuterated domperidone can be synthesized or prepared by several routes. In general, any hydrogen in the chemical structure of domperidone can be either hydrogen or deuterium. Beneficially, the sites of domperidone metabolism, i.e., all non-substituted sites on the aromatic rings, can be blocked by adding a commercially available deuterated alkyl halide, and the metabolite can be blocked by adding a commercially available deuterated alkyl halide for the propyl linker. This can considerably lower domperidone metabolism and improve its bioavailability.

Deuteration of a drug increases drug half-life, allowing for less frequent dosing as well as improved pharmacokinetics, i.e., absorption, distribution, and metabolism. The kinetic isotope effect (KIE) and deuterium kinetic isotope effect (DKIE) are used to incorporate deuterium into drugs. Gant, J. Med. Chem. (2014) 57, 3595-3611.

Deuterium forms more stable bonds with carbon than hydrogen. In some cases, deuterium substitution may provide altered drug metabolism. Altered drug metabolism may take many forms, e.g., improved metabolite stability, reduced formation of toxic metabolites, and/or increased formation of active metabolites. Deuterated compounds may have an increased half-life and increased systemic exposure compared to corresponding non-deuterated forms. The increased half-life and decreased metabolism may provide enhanced efficacy, tolerance, safety, and convenience so that lower doses of the deuterated form may yield similar results as higher doses of the non-deuterated form. Deuterated compounds generally retain the biochemical potency and selectivity as the corresponding non-deuterated forms. Any effects of deuterium substitution on metabolic parameters are highly dependent on the specific molecular positions at which deuterium is substituted for hydrogen.

Metabolic effects of deuterium substitution are not obvious or predictable, even in compounds having similar chemical structures. For example, U.S. Publication No. 2009/0076010 discloses deuterium enriched lamotrigine, an anticonvulsant. Deuteration is 14% to 100%, depending upon the position of the hydrogen replaced by deuterium. Enrichment methods can be by proton exchange with deuterium, or by molecule synthesis with deuterium enriched starting materials. U.S. Publication No. 2009/0131485 discloses deuterium enriched pirfenidone, an inhibitor of collagen production blocking fibroblast proliferation and stimulation in response to cytokines, investigated for treating neurofibromatosis, multiple sclerosis, and other fibroid related diseases. It discloses synthesis methods and isotopes, and methods for enhancing bioavailability and dosing. Deuterated pirfenidone has a half-life ranging from 110%-140% or more, depending on the degree of deuteration. The effective amount ranges from 80% to 40% or less compared to non-deuterated forms. U.S. Publication no. 2011/0160253 discloses deuterium enriched tizanidine, a benzothiazole that acts as a centrally acting $\alpha_2$-adrenoceptor agonist used to manage muscle hypertonia and muscle spasticity associated with multiple sclerosis, spinal cord injury, etc. It discloses deuteration methods; enrichment ranges from 52.5%-99.5% and pharmaceutical compositions, effective amounts, and doses are discloses. Harbeson and Tung, MECHEM NEWS No. 2 May 2014, 8-22 disclose deuterium substitution can improve safety, efficacy, and/or tolerance of a therapeutic agent.

Deuterated drugs have been used in non-clinical settings and as metabolic and pharmacokinetic probes, but none are approved as a human therapeutic. Depending on the desired deuteration sites, $D_2O$ may be exchanged directly into the finished drug compounds, or into reagents used for synthesizing drugs. Deuterium has low systemic toxicity. Deuterium gas may be used as a starting material for incorporating deuterium. Catalytic deuteration of olefinic and acetylenic bonds can rapidly incorporate deuterium. Metal catalysts such as Pd, Pt, and Rh in the presence of deuterium gas can be used to directly exchange deuterium for hydrogen in functional groups containing hydrocarbons. Deuterated regents and synthetic building blocks are commercially available. The shape and size of a molecule is very similar in a deuterated versus non-deuterated form. Minor physical property changes in partially or fully deuterated compounds are reduced hydrophobicity, decreased acidity of carboxylic acids and phenols, and increased basicity of amines but most of these small differences have negligible effects on biochemical potency or target selectivity. Binding isotope effects are well known and can contribute either positively or negatively to a measured deuterium kinetic isotope effect. There are also reduced metabolic rates and metabolic switching, where the ratio of metabolites is changed. Changes in an individual's exposure to parent drug and metabolites can have ramifications on pharmacodynamics, tolerance, and efficacy of the deuterated drug. Deuteration reduces formation of undesired or toxic metabolites, as well as enhancing formation of desired metabolites. An example of positive effects of metabolic shunting is deuterated nevirapine that resulted in reduced rash incidence and severity, and each of deuterated efavirenz, indilon, and odanacatib resulted in lower side effects with enhanced efficacy in a rat model. Deuterated rofecoxib, also known as BDD-11602, had an improved pharmacokinetic profile in a rat model compared to non-deuterated rofecoxib. Deuterated telaprevir, an inhibitor of hepatitis C viral NS3-4A protease, had a 13% increase in epimerization rate, but negligible effect on antiviral activity. Deuterated effects on the metabolic profile of any particular drug are not predictable, although there is potential for improved safety, tolerability, efficacy, and dosing.

One method to decrease domperidone metabolism is to administer a deuterated form of domperidone. A deuterated form of a small molecule may increase its retention and thus decrease its metabolism, permitting a lower dose to be administered but achieving the same efficacy as the higher dose, but without the cardiac symptoms. Domperidone is extensively metabolized, but deuteration slows metabolism at key sites and key routes of metabolism, producing higher efficacy with a lower dose. This is demonstrated in FIGS. 1A and 1B, subsequently described, where the area under the curve is higher for the deuterated compounds. Table 1, subsequently described, shows the reduction in metabolite formation for compound 2 over a 60 min time period.

Compound 1 below shows a general deuterated form of domperidone where R=either H or D, independently, thereby allowing for 1 to 10 deuterium to be present. Any and all permutations of deuterated sites may be used without limitation. The most significant sites for deuteration are the aromatics as shown, and the methylene of the alkyl linker alpha to the piperidine nitrogen. The primary hydroxylated metabolites are in this aromatic ring and the presence of deuterium may reduce the rate at which these metabolites are formed. The dealkylation metabolic pathway involves those alpha protons via an elimination mechanism of the N-oxide; deuterium is slower to eliminate thus slowing this route of metabolism. In one embodiment, deuterated compounds of compound 1 are used and/or prepared as described herein.

Domperidone may be deuterated at any hydrogen site. In compound 2, deuteration of the aromatic H atoms, of the unsubstituted aromatic ring, yields domperidone-$d_4$. Additional deuteration of one or more methylene sites in the linking propyl group, yields compound 3 (domperidone-$d_6$) or domperidone-$d_8$ (not shown) or compound 5 (domperidone-$d_{10}$). It is also possible to deuterate one or more of the methylene sites while retaining H at the aromatic sites. For example, deuteration of one methylene group yields compound 4 (domperidone-$d_2$), and deuteration of two methylene groups yields domperidone-$d_4$ (not shown).

In one embodiment, any of compounds 2, 3, 4, 5, or 6 are administered. Any of compounds 2, 3, and 4 impact reducing the rate of metabolism and are preferred.

Raw materials with deuterium only at the alpha methylene are likely more expensive and less readily available than those where the propyl group is fully deuterated.

Compound 2 is used and is preferred in one embodiment.

Compound 3 is used and is preferred in another embodiment.

Compound 4 is used and is preferred in a further embodiment.

Compound 5 is used and is preferred in one embodiment.

Compound 6 is used and is preferred in yet another embodiment.

Compounds 2 and 5 are used and are preferred in one embodiment.

Compounds 2, 5, and 6 are used in one embodiment.

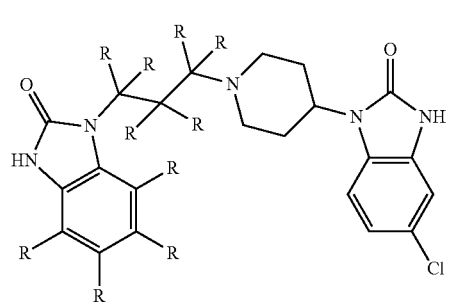

1

R = H or D

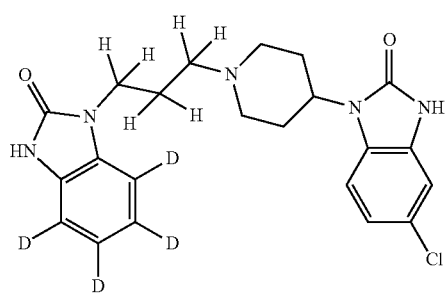

2

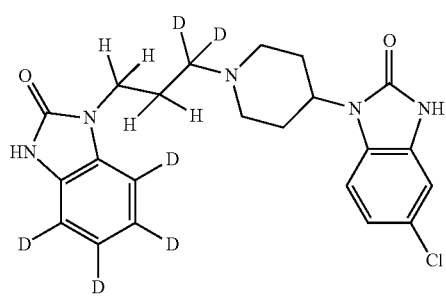

3

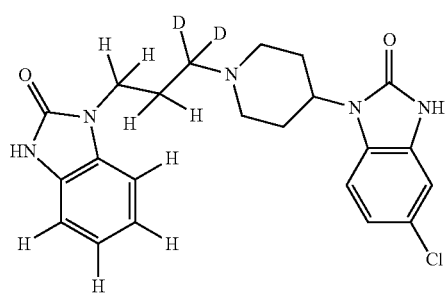

4

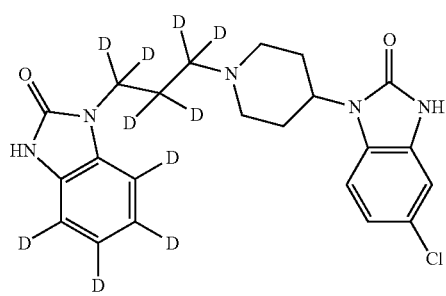

5

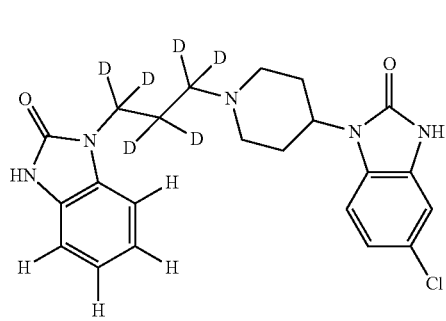

6

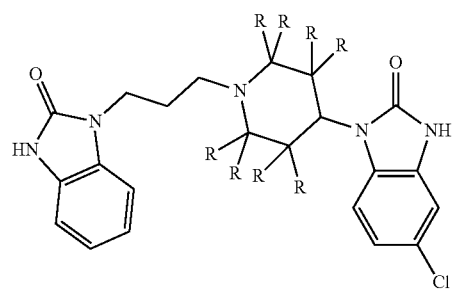

13

R = H or D

Thus, the present disclosure provides methods for ameliorating gastroesophageal reflux disease, functional dyspepsia, or nausea and vomiting associated with chemotherapy, in a patient, comprising administering a therapeutically effective amount of a compound that is $d_2$-domperidone 4, $d_4$-domperidone 2, $d_6$-domperidone 3, or $d_{10}$-domperidone 5, or a pharmaceutically acceptable salt thereof to the patient:

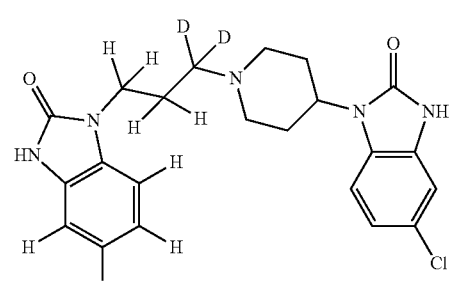

($d_2$-domperidone)

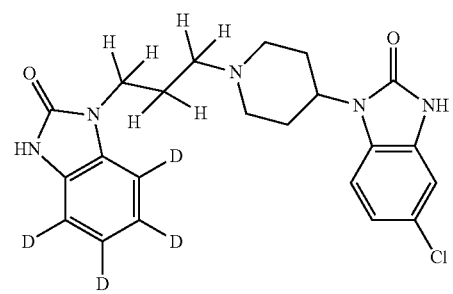

($d_4$-domperidone)

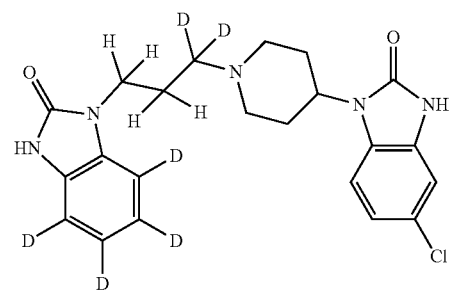

($d_6$-domperidone)

In one embodiment, compounds containing 1-8 deuteriums in the cyclohexyl amine, such as compound 13, are used.

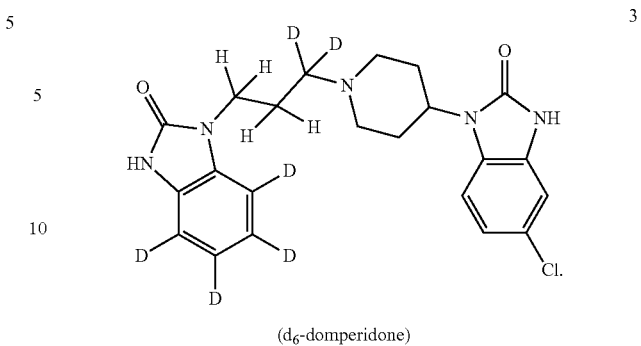

(d₆-domperidone)

In some embodiments, the compound is d₂-domperidone 4 or a pharmaceutically acceptable salt thereof:

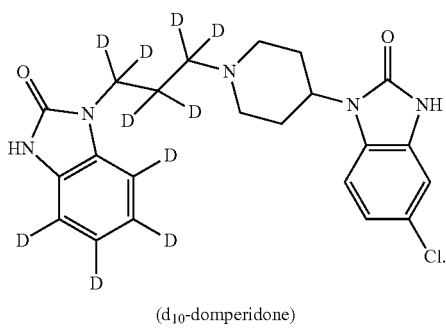

(d₂-domperidone)

In other embodiments, the compound is d₄-domperidone 2 or a pharmaceutically acceptable salt thereof:

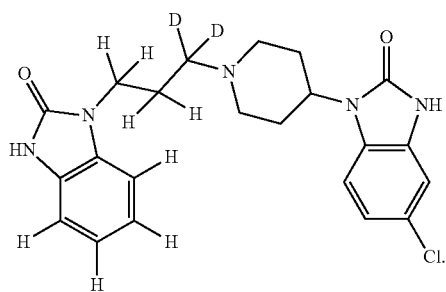

(d₄-domperidone)

In yet further embodiments, the compound is d₆-domperidone 3 or a pharmaceutically acceptable salt thereof:

In still other embodiments, the compound is d₁₀-domperidone 5 or a pharmaceutically acceptable salt thereof:

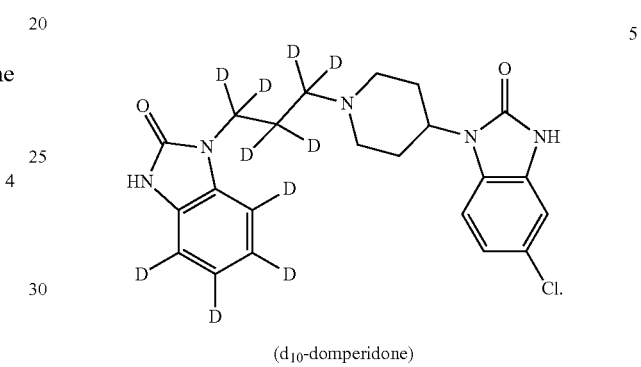

(d₁₀-domperidone)

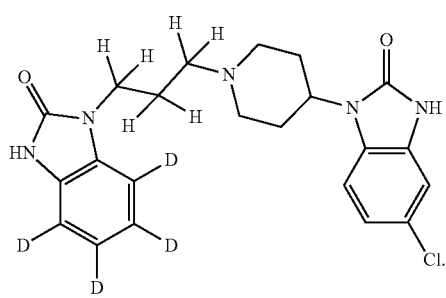

(d₁₀-domperidone)

In some embodiments, the deuterated compounds may be used in the methods described herein for ameliorating gastroesophageal reflux disease.

In other embodiments, the deuterated compounds may be used in the methods described herein for ameliorating functional dyspepsia.

In further embodiments, the deuterated compounds may be used in the methods described herein for ameliorating nausea and vomiting associated with chemotherapy.

Scheme 1 shows a general synthesis for preparing various deuterated domperidone compounds generally shown as compound 1. Synthesis is based on the non-deuterated analog in Vandenberk U.S. Pat. No. 4,066,772. The process begins with 1,2-diaminobenzene substituted with 0 to 4 deuteriums on the aromatic ring. The imide is closed using ethyl chloroformate, or another similar reactive carbonyl species, in an appropriate solvent such as, but not limited to, an ether such as tetrahydrofuran (THF), halocarbons such as dichloromethane, ketones such as acetone, hydrocarbons such as heptane, and amides such as N,N-dimethylformamide (DMF). Compound 8 is then monoprotected with an appropriate protecting group such as, but not limited to, carbamates, sulfonamides, and vinyl alkyls. The second nitrogen is then reacted with a 1,3-bifunctional propyl derivative containing 0 to 6 deuteriums. The functionality can be independently either halogen (Br, Cl, I), hydroxyl, or an appropriate leaving group such as tosylate or mesylate. In a preferred embodiment, the two groups are differentiated. The remaining leaving group X of compound 10 may be optionally exchanged for a more reactive species, e.g., if X is chloride the chloride may be exchanged for an iodide, or if X is a tosylate the tosylate may be exchanged for a trifluoromethanesulfonate (triflate). Protecting group P may also be removed in this step.

Intermediate 10 or 12 is then reacted with compound 14 using either a base or other appropriate coupling procedure. Compound 14 is prepared using methods known in the art. Removal of the protecting group yields the desired deuterated domperidone derivative 1. Alternatively, protecting group P may be removed prior to alkylation with 14. All compounds are prepared in accord with this general scheme using the appropriately substituted deuterated starting materials.

Synthesis of compound 13 follows known methods for non-deuterated material but beginning with a deuterated 4-aminopiperidine derivative.

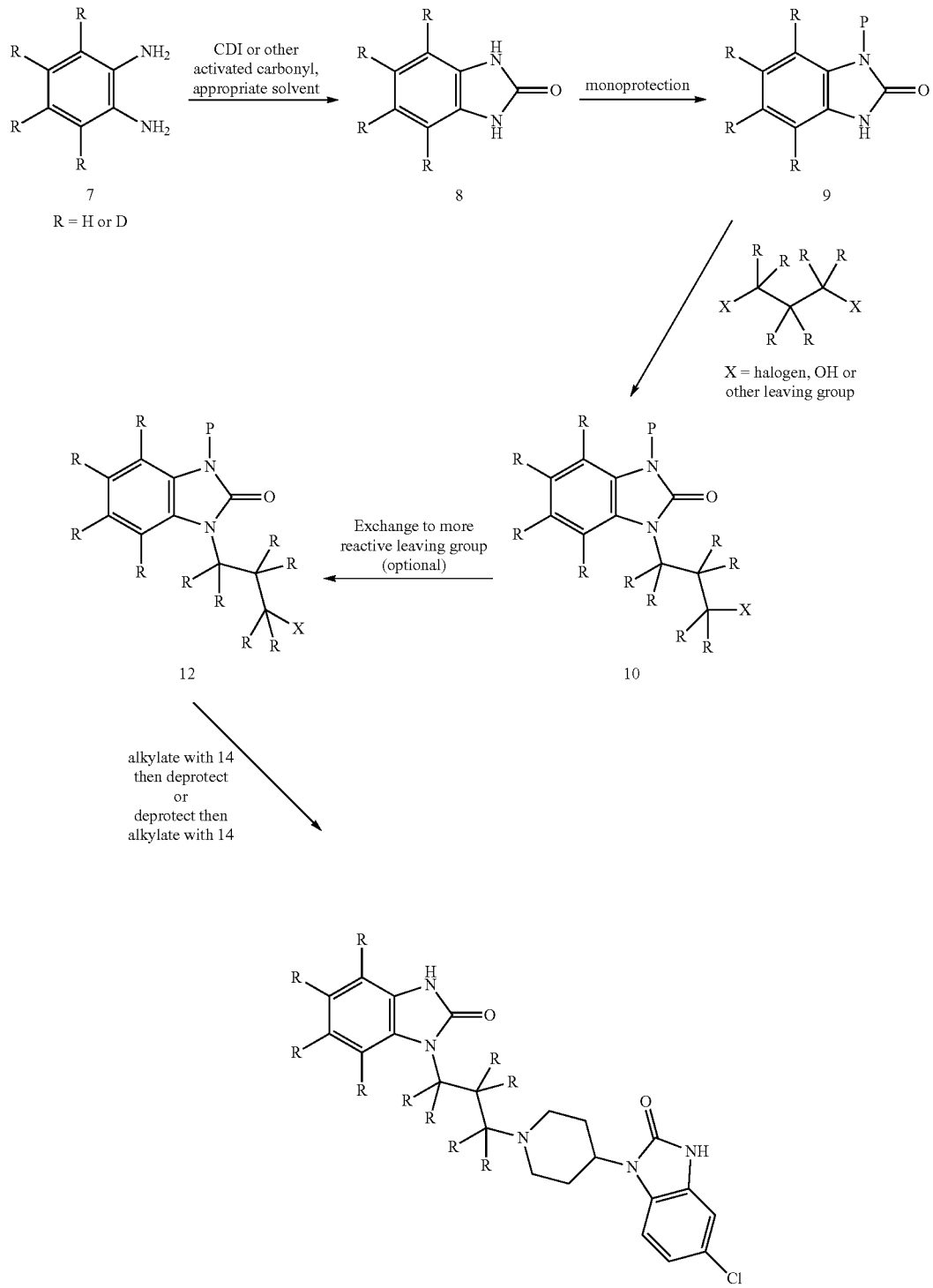

Scheme 1 General Synthesis of Deuterated Domperidone

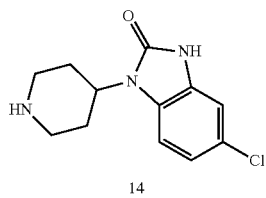

14

Scheme 2 shows an alternative synthesis for deuterated domperidone. An appropriately deuterated 1,2-aminobenzene is reacted with tetraethyl orthocarbonate in the presence of a catalyst and in a suitable solvent, resulting in compound 15. In one embodiment the catalyst is acetic acid. In one embodiment the solvent is ethanol. In another embodiment the catalyst is propionic acid. In another embodiment the solvent is isopropyl alcohol. In embodiments, an appropriate organic or inorganic acid in an appropriate solvent may be used, non-limiting examples include an ether or alcohol. A 1,3-bifunctional propyl derivative containing 0-6 deuteriums is then reacted with the protonated nitrogen N of imide 15 in the presence of base and in a solvent to provide compound 16. In one embodiment the base is K$_2$CO$_3$. In one embodiment the solvent is methyl isobutyl ketone (MIBK). In another embodiment the base is sodium hydride. In another embodiment the solvent is dimethylformamide (DMF). In embodiments, organic bases such as N,N-diisopropylethylamine (DIPEA), n-butyllithium (nBuLi), lithium bis(trimethylsilyl)amide (LHMDS), etc., or inorganic bases such as potassium hydride as examples may be used. Substitution of compound 14 and deprotection of the benzimidazole results in deuterated domperidone 1.

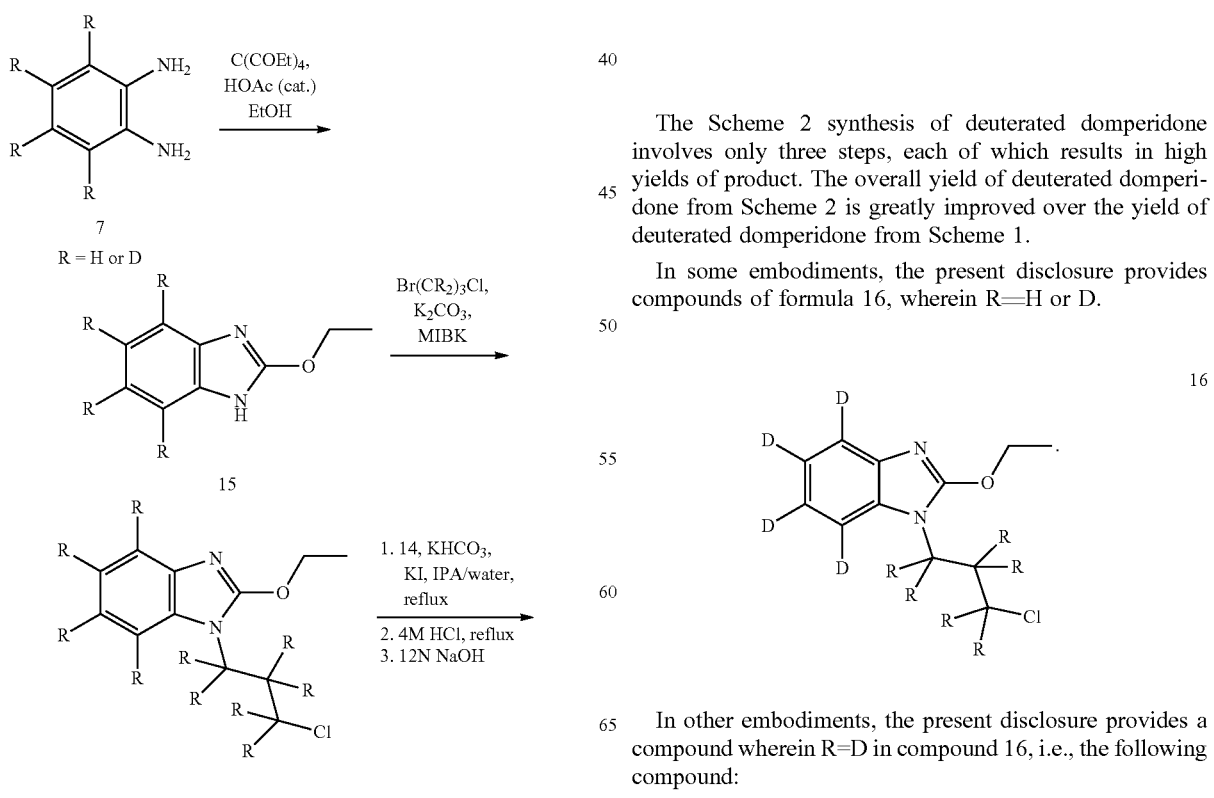

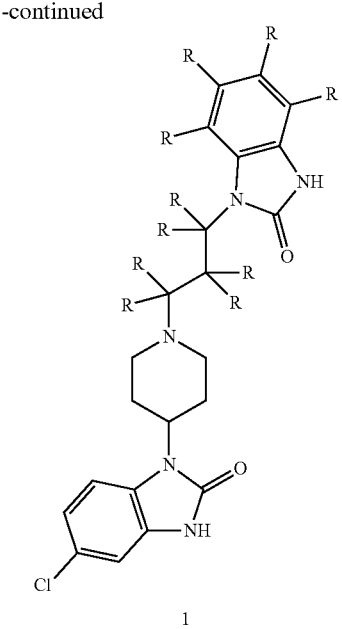

1

The Scheme 2 synthesis of deuterated domperidone involves only three steps, each of which results in high yields of product. The overall yield of deuterated domperidone from Scheme 2 is greatly improved over the yield of deuterated domperidone from Scheme 1.

In some embodiments, the present disclosure provides compounds of formula 16, wherein R=H or D.

In other embodiments, the present disclosure provides a compound wherein R=D in compound 16, i.e., the following compound:

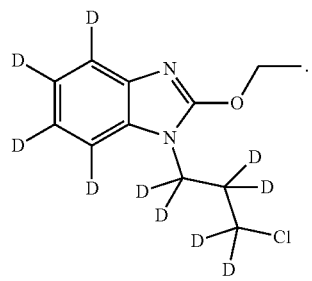 [SMILES: [2H]c1c([2H])c([2H])c2c(nc(OCC)n2C([2H])([2H])C([2H])([2H])C([2H])([2H])Cl)c1[2H]]

In further embodiments, present disclosure provides a compound of formula 16, wherein R=H, i.e., a compound of the following structure:

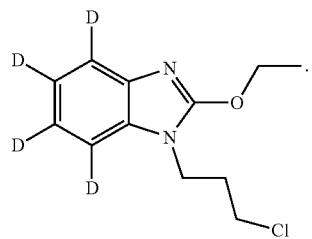 [SMILES: [2H]c1c([2H])c([2H])c2c(nc(OCC)n2CCCCl)c1[2H]]

In some embodiments, methods of preparing deuterated domperidone Compound 1 are provided. The method comprise (i) reacting a 1,2-diaminobenzene having 0-4 deuterium atoms with tetraethyl orthocarbonate; (ii) reacting the product of step (i) with Br(CR$_2$)$_3$Cl to produce an intermediate; and (iii) reacting the intermediate with 5-chloro-1-(4-piperidyl)-1H-benzimidazol-2(3H)-one.

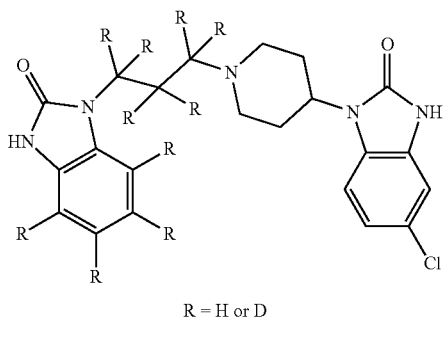

R = H or D

In other embodiments, methods of preparing deuterated domperidone Compound 2 are provided. These methods comprise (i) reacting 1,2-diaminobenzene having 4 deuterium atoms with tetraethyl orthocarbonate; (ii) reacting the product of step (i) with Br(CH$_2$)$_3$Cl to produce an intermediate; and (iii) reacting the intermediate with 5-chloro-1-(4-piperidyl)-1H-benzimidazol-2(3H)-one.

2

The deuterated domperidone compounds may be administered by any route as determined by one skilled in the art including, without limitation, oral, rectal, nasal, parenteral (i.e., subcutaneous, intradermal, intramuscular, intraperitoneal, intravenous, intraarticular, intramedullar), intraperitoneal, transmucosal, transdermal, or topical (i.e., dermal, buccal, sublingual, intraocular). In some embodiments, the deuterated domperidone compounds are administered in the form of pharmaceutical compositions.

The formulations can be administered orally in solid form, such as a tablet, capsule, lozenge, or gum, or in liquid form as a syrup, emulsion, solution, or suspension in an aqueous or non-aqueous vehicle. In solid forms, formulations may be controlled release or rapid dissolution for rapid onset. The formulations can also be administered by injection, which can be subcutaneous, intradermal, intramuscular, intravenous, or other injection methods. Formulations for administration through injection can include suspensions, solutions, or emulsions in aqueous or non-aqueous vehicles. Other formulations can be delivered intranasally, vaginally, rectally, or transdermally. Formulations can also be delivered transmucosally. The preparation can be administered once a day to four times a day.

Typically, the pharmaceutical compositions are formulated to tailor to the particular administration route. In some embodiments, the pharmaceutical compositions are in the form of tablets, capsules (hard and soft gelatin capsules), sachets, dragees, powders, granules, lozenges, powders for reconstitution, liquid preparations (solutions, emulsions, suspensions, or syrups), patches, inhalants, or suppositories. Thus, the pharmaceutical compositions typically contain pharmaceutically acceptable excipients.

For inclusion in the pharmaceutical compositions, the pharmaceutically acceptable excipients are selected based on the mode of administration and may include inert and/or active components. In some embodiments, the pharmaceutically acceptable excipient is sterile, non-toxic, and/or biologically suitable for administration to a subject, i.e., buffered to an appropriate pH and isotonicity. In other embodiments, the pharmaceutically acceptable excipients include diluents (such as inert), carrier, adjuvant, fillers.

The deuterated domperidone or pharmaceutical composition comprising same may also contain and/or be administered with other active agents. In some embodiments, the additional active agent is useful for treating GERD. In other embodiments, the additional active agent is useful for treating functional dyspepsia. In further embodiments, the additional active agent is useful for treating nausea and/or vomiting associated with chemotherapy. Thus, the additional active agent may include antacids, H-2-receptor blockers (such as cimetidine, famotidine, nizatidine, or ranitidine), proton pump inhibitors (such as lansoprazole, omeprazole, pantoprazole, rabeprazole, or dexlansoprazole), medications that strengthen the lower esophageal sphincter (such as baclofen), anti-nausea or anti-vomiting drugs such as aprepitant, dolasetron, granisetron, ondansetron, palonosetron, proclorperazine, promethazine, netupitant-palonosetron, rolapitant, lorazepam, metoclopramide, or dexamethasone, or combinations thereof.

In some embodiments, the deuterated domperidone is administered orally, transdermally, parenterally, or a combination thereof. In other embodiments, the deuterated domeridone is administered transdermally. In further embodiments, the deuterated domperidone is administered parenterally. In yet other embodiments, the deuterated domperidone is administered orally.

FIG. 1 shows decreased metabolism caused by deuteration of domperidone, where the area under the curve of rat plasma levels of orally administered domperidone is higher for the deuterated domperidone compounds 2 and 6 relative to undeuterated domperidone. The table below shows reduced metabolite formation in human hepatocytes for domperidone compounds 2 and 6 over a 60 min. time period relative to undeuterated domperidone.

TABLE 1

Percentage of metabolite formation in human hepatocytes

| Sample | % of oxidative metabolite | % of sulfonated metabolite |
|---|---|---|
| Domperidone 0 min | 0.08 | 0 |
| Domperidone 30 min | 2.64 | 0.23 |
| Domperidone 60 min | 3.79 | 0.37 |
| Compound 2 0 min | 0 | 0 |
| Compound 2 30 min | 0.15 | 0.01 |
| Compound 2 60 min | 0.21 | 0.02 |
| Compound 6 0 min | 0.03 | 0 |
| Compound 6 30 min | 1.42 | 0.13 |
| Compound 6 60 min | 1.91 | 0.22 |

Another method to decrease domperidone metabolism is to administer the drug sublingually, so that the active is immediately available in the circulatory system and bypasses the digestive system where metabolism occurs. A sublingual form of domperidone or a deuterated domperidone, formulated as a tablet, film, or other suitable formulation, can be administered at a lower dose but with comparable efficacy as an orally administered form. The pharmacokinetics of domperidone, particularly its $t_{1/2}$, $pK_a$, log P, and $K_d$ make it favorable for sublingual administration.

Another method to decrease domperidone metabolism is to administer the active in a particulate form providing increased surface area. For example, domperidone or a deuterated domperidone can be formulated as microparticles or nanoparticles. Using the biopharmaceutics classification system (BCS), it is known that Class II drugs have high permeability and low solubility, such that their bioavailability is limited by their rate of solvation. In this embodiment, the microparticle or nanoparticle or other formulation providing increased surface area increases bioavailability by increasing the rate of solvation, and can be administered at a lower dose but with comparable efficacy as an orally administered form.

It will be appreciated that other formulations may achieve similar or the same results, e.g., using a spray formulation, a powder, a thin film, etc., and using either domperidone or a deuterated domperidone.

It will be appreciated that the embodiments may be used in combination. As one example, a microparticle or nanoparticle form of domperidone may be applied to or incorporated in a thin film and administered sublingually. As another example, a deuterated form of domperidone may be formulated as a microparticle or nanoparticle, and may in some embodiments be administered sublingually, e.g., in or on a thin film, as a spray, etc. In these combination examples, the dose of domperidone may be further reduced due to its increased bioavailability and decreased metabolism.

The following preparations and formulations can be used for either deuterated or non-deuterated forms of domperidone.

Nanoparticles can be prepared using dry milling or wet milling. Examples of dry milling processes include those disclosed in U.S. Patent Publication Nos. 2013/0209569, 2010/0092563, 2014/0287039, 2014/0200276, 2014/0194487, 2014/0255494, 2013/0243854, 2014/0248359, 2014/0256781, 2014/0302127, 2014/019395, 2014/0220121, 2012/0135048, 2014/0326812, 2009/0028948, and U.S. Pat. Nos. 9,089,471; 9,095,496; 9,180,096; 9,173,854; 9,017,721; 8,679,544; 8,999,387; 8,734,847; 8,992,982; 9,180,096; 9,186,328; 8,735,450; and 8,808,751. An exemplary wet milling process is disclosed in U.S. Pat. No. 9,107,827. Any of these formulations, including but not limited to thin films, tablets, sprays, solutions, etc. include a sublingual dosage form.

Domperidone, either deuterated or non-deuterated forms, can be administered through the skin, i.e., transdermally. Absorption through the skin, also referred to as percutaneous delivery, transdermal delivery, or dermal delivery, transports domperidone from the outer epidermal surface both into the skin and into the systemic circulation. The epidermal surface is the primary route of absorption in transdermal delivery, although small amounts of agent may also be transferred through hair follicles or glands. From the epidermal starting surface, the agent passes through seven epidermal layers prior to entering the dermis, from which the agent enters the circulatory and/or lymphatic systems. The stratum corneum is the outermost or surface exposure skin layer, and is the rate-limiting barrier for entry of an external agent, thus the rate of passage through the stratum corneum determines overall absorption. The primary stratum corneum components are the lipophilic compounds cholesterol, cholesterol esters, and ceramides. Agents with greater lipid-solubility thus more rapidly penetrate the stratum corneum and achieve systemic exposure, compared to agent with less lipid-solubility, but the majority of all agents penetrate the stratum corneum to some extent. The solubility of domperidone is related to its pH; domperidone is a weak base, $pK_a$ 7.89, with limited solubility in water having a lipid to water ratio of 3.90.

The health and integrity of the stratum corneum affects agent penetration. For example, agents such as strong acids that injure or disrupt the stratum corneum composition are rapidly absorbed. Skin damage due to burns, abrasions, wounds, and disease also affect absorption. Some solvents, e.g., dimethyl sulfoxide (DMSO) increase the permeability of stratum corneum, acting as carriers and thus used as penetration enhancers or facilitators. Some surfactants, e.g., sodium lauryl-sulfate, increase skin penetration of water soluble agents, possibly in increasing skin permeability of water.

Transdermal delivery may be achieved by topical administration, environmental exposure, and/or injection. Absorption through the skin depends on agent factors including but not limited to concentration, molecular weight, and lipophilic/hydrophilic nature or solubility, but also contact duration, physical condition of the skin, surface exposed, and the presence or absence of hair follicles on the exposed surface. For example, agent absorption from various skin surfaces occurs according to the following scheme from quickest to slowest:

scrotal>forehead>axilla>scalp>back>abdomen>palm/foot undersurface due to the keratinized, stratified squamous cell layer of stratum corneum that functions to prevent water loss from underlying tissues.

Dermal application of domperidone may permit more localized therapy, and may avoid or minimize first pass hepatic metabolism. Dermal administration may thus achieve higher systemic concentrations. Dermal administration formulations include patches, lotions, liniments, ointments, tinctures, creams, powders, aerosols, gels, etc. Patches may be controlled release and may permit domperidone release for 7 days, in one embodiment. Patches may include a penetration enhancer, which may facilitate or in some cases be important for delivery. In a transdermal patch, domperidone or a prodrug form of domperidone is present in as a free base and/or salt.

The amount of domperidone that is absorbed by transdermal application can be measured directly or indirectly using methods known in the art and as subsequently described. Even with in vivo studies, species differences may be notable. Moreover, the different formulations previously described may affect concentrations delivered. Direct concentration measurement may be performed using in vivo methods by directly applying domperidone to the skin and measuring domperidone in blood and urine at set times, then plotting the results on a graph and measuring the area under the curve (AUC). Ex vivo methods may be used because the permeability of the stratum corneum is not significantly changed when skin is carefully removed. Chamber studies, using any formulation of domperidone (e.g., films, patches, lotions, etc., see e.g., Basu, IRJP 3 (2012) 134-45; Madishetti et al. Dam 18 (2010) 221-29; Khan et al. Bull. Pharm. Res. 2 (2012) 15-21) applied to one surface of an isolated skin sample and its concentration measured on the other surface of the same sample, are known, e.g., isolated perfused porcine flap (Riviere, Fundam Appl Toxicol 7 (1986) 444-53). In vitro methods include static and flow-through diffusion cells, examples of which are Franz cells and Bronaugh cells (Bronaugh and Stewart, J. Pharm. Sci, 74 (1985) 64-67), respectively. The static Franz cell apparatus has an upper donor chamber and a lower receiving chamber containing a fluid, with the upper and lower chambers separated by the skin sample as a membrane. The receiving fluid in the lower chamber is typically buffered saline with a known amount of protein, e.g., bovine serum albumen or a biological fluid, and is in contact with the skin membrane. In use, a known volume and concentration of domperidone in a vehicle is applied to the upper chamber and permeates through the skin membrane, diffusing or otherwise entering into the receiving fluid in the lower chamber. This receiving fluid is sampled, typically via a sampling port that also replaces the fluid volume removed, and analyzed at regular intervals to determine the amount of domperidone that permeated the skin membrane. The flow-through Bronaugh cell apparatus is similar to the Franz cell apparatus, but uses a flow-through system in the lower chamber from which samples are obtained and analyzed continuously rather than at set time points.

Methods for domperidone transmucosal delivery are disclosed in U.S. Publication No. 2010/0255096. Mucoadhesive delivery technologies provide safe and efficacious delivery of an agent such as domperidone. These mucoadhesive delivery technologies include all methods of diffusion in the oral mucosa: passive diffusion including trans-cellular (through cells) and para-cellular (through lipid rich domains around the cells), carrier mediated transport, and endocytosis/exocytosis for active cellular uptake and excretion by the endocytic pathway.

Mucous membranes, mucosae, line body cavities that are either externally exposed to the environment or are internal organs. The oral mucosa is the mucous membrane lining the inside of the mouth and consists of stratified squamous epithelium (oral epithelium) and an underlying connective tissue (lamina propria). It can be further divided into three main categories based on function and histology: masticatory mucosa of keratinized stratified squamous epithelium found on the dorsum of the tongue, hard palate and attached gingiva; lining mucosa of non-keratinized squamous epithelium found almost everywhere else in the oral cavity including the buccal mucosa which lines the cheeks, the labial mucosa which is the inside lining of the lips, and the alveolar mucosa which is the mucosa between the gums and the buccal/labial mucosa; and specialized mucosa in the regions of the taste buds on lingual papillae on the dorsal surface of the tongue. Bioadhesive polymers adhere to any moist surface, thus a mucoadhesive/bioadhesive formulation adheres to both saliva-moistened keratinized and non-keratinized mucosa.

Exemplary transdermal formulations are provided below, all percentages are weight/weight. While the following formulations list domperidone, one of ordinary skill in the art is aware that domperidone may refer to either domperidone or deuterated domperidone.

| Formulation | | Formulation | |
|---|---|---|---|
| 1 | Domperidone 1%<br>Dimethyl sulfoxide<br>qs to 100% | 2 | Domperidone 1%<br>Diethyl sebacate 15%<br>Dimethyl sulfoxide<br>qs to 100% |
| 3 | Domperidone 1%<br>Diisopropyl adipate 20%<br>Dimethyl sulfoxide<br>qs to 100% | 4 | Domperidone 1%<br>Dimethyl isosorbide 15%<br>Dimethyl sulfoxide<br>qs to 100% |
| 5 | Domperidone 1%<br>Dipropylene glycol 10%<br>Dimethyl sulfoxide<br>qs to 100% | 6 | Domperidone 1%<br>Hexylene glycol 12%<br>Dimethyl sulfoxide<br>qs to 100% |
| 7 | Domperidone 1%<br>Propylene carbonate 5%<br>Dimethyl sulfoxide<br>qs to 100% | 8 | Domperidone 1%<br>TRANSCUTOL ® 20%<br>Dimethyl sulfoxide<br>qs to 100% |

| Formulation | | Formulation | |
|---|---|---|---|
| 9 | Domperidone 1%<br>Lauric diethanolamide 15%<br>Dimethyl sulfoxide<br>qs to 100% | 10 | Domperidone 1%<br>PEG 400 20%<br>Dimethyl sulfoxide<br>qs to 100% |
| 11 | Domperidone 1%<br>Cocamide DEA 5%<br>Dimethyl sulfoxide<br>qs to 100% | 12 | Domperidone 1%<br>Oleic acid 20%<br>Dimethyl sulfoxide<br>qs to 100% |
| 13 | Domperidone 1%<br>PEG-7 methyl ether 20%<br>Dimethyl sulfoxide<br>qs to 100% | 14 | Domperidone 1%<br>Polysorbate 80 15%<br>Dimethyl sulfoxide<br>qs to 100% |
| 15 | Domperidone 1%<br>BRIJ ® L23 69 LQ 5%<br>Dimethyl sulfoxide<br>qs to 100% | 16 | Domperidone 1%<br>BRIJ ® S 20 So MH 5%<br>Dimethyl sulfoxide<br>qs to 100% |
| 17 | Domperidone 1%<br>BRIJ ® L4 LQ 5%<br>Dimethyl sulfoxide<br>qs to 100% | 18 | Domperidone 1%<br>Isopropyl palmitate 8%<br>Dimethyl sulfoxide<br>qs to 100% |
| 19 | Domperidone 1%<br>Levulinic acid 5%<br>Dimethyl sulfoxide<br>qs to 100% | 20 | Domperidone 1%<br>Lauryl lactate 5%<br>Dimethyl sulfoxide<br>qs to 100% |
| 21 | Domperidone maleate 1%<br>Dimethyl sulfoxide<br>qs to 100% | 22 | Domperidone maleate 1%<br>Diethyl sebacate 15%<br>Dimethyl sulfoxide<br>qs to 100% |
| 23 | Domperidone maleate 1%<br>Diisopropyl adipate 20%<br>Dimethyl sulfoxide<br>qs to 100% | 24 | Domperidone maleate 1%<br>Dimethyl isosorbide 15%<br>Dimethyl sulfoxide<br>qs to 100% |
| 25 | Domperidone maleate 1%<br>Dipropylene glycol 10%<br>Dimethyl sulfoxide<br>qs to 100% | 26 | Domperidone maleate 1%<br>Hexylene glycol 12%<br>Dimethyl sulfoxide<br>qs to 100% |
| 27 | Domperidone maleate 1%<br>Propylene carbonate 5%<br>Dimethyl sulfoxide<br>qs to 100% | 28 | Domperidone maleate 1%<br>TRANSCUTOL ® 20%<br>Dimethyl sulfoxide<br>qs to 100% |
| 29 | Domperidone maleate 1%<br>Lauric diethanolamide 15%<br>Dimethyl sulfoxide<br>qs to 100% | 30 | Domperidone maleate 1%<br>PEG 400 20%<br>Dimethyl sulfoxide<br>qs to 100% |
| 31 | Domperidone maleate 1%<br>Cocamide DEA 5%<br>Dimethyl sulfoxide<br>qs to 100% | 32 | Domperidone maleate 1%<br>Oleic acid 20%<br>Dimethyl sulfoxide<br>qs to 100% |
| 33 | Domperidone maleate 1%<br>PEG-7 methyl ether 20%<br>Dimethyl sulfoxide<br>qs to 100% | 34 | Domperidone maleate 1%<br>Polysorbate 80 15%<br>Dimethyl sulfoxide<br>qs to 100% |
| 35 | Domperidone maleate 1%<br>BRIJ ® L23 69 LQ 5%<br>Dimethyl sulfoxide<br>qs to 100% | 36 | Domperidone maleate 1%<br>BRIJ ® S 20 So MH 5%<br>Dimethyl sulfoxide<br>qs to 100% |
| 37 | Domperidone maleate 1%<br>BRIJ ® L4 LQ 5%<br>Dimethyl sulfoxide<br>qs to 100% | 38 | Domperidone maleate 1%<br>Isopropyl palmitate 8%<br>Dimethyl sulfoxide<br>qs to 100% |
| 39 | Domperidone maleate 1%<br>Levulinic acid 5%<br>Dimethyl sulfoxide<br>qs to 100% | 40 | Domperidone maleate 1%<br>Lauryl lactate 5%<br>Dimethyl sulfoxide<br>qs to 100% |
| 41 | Domperidone maleate 1%<br>DURO-TAK ® 387-2516 79%<br>Dimethyl sulfoxide<br>qs to 100% | 42 | Domperidone maleate 1%<br>DURO-TAK ® 387-2516 60%<br>TRANSCUTOL ® 20<br>Dimethyl sulfoxide<br>qs to 100% |
| 43 | Domperidone maleate 1%<br>DURO-TAK ® 387-2516 68%<br>Hexylene glycol 12%<br>Dimethyl sulfoxide<br>qs to 100% | 44 | Domperidone maleate 1%<br>DURO-TAK ® 387-2516 75%<br>BRIJ ® S 20 So MH 5%<br>Dimethyl sulfoxide<br>qs to 100% |
| 45 | Domperidone maleate 1%<br>DURO-TAK ® 387-2516 75%<br>BRIJ ® L4 LQl 5% | 46 | Domperidone maleate 1%<br>DURO-TAK ® 387-2516 60%<br>Diethyl sebacate 20% |

-continued

| Formulation | | Formulation | |
|---|---|---|---|
| | Dimethyl sulfoxide<br>qs to 100% | | Dimethyl sulfoxide<br>qs to 100% |
| 47 | Domperidone maleate 1%<br>DURO-TAK ® 387-2516 60%<br>Diisopropyl adipate 20%<br>Dimethyl sulfoxide<br>qs to 100% | 48 | Domperidone maleate 1%<br>DURO-TAK ® 387-2516 70%<br>Levulinic acid 10%<br>Dimethyl sulfoxide<br>qs to 100% |
| 49 | Domperidone maleate 1%<br>DURO-TAK ® 387-2516 70%<br>Lauryl lactate 10%<br>Dimethyl sulfoxide<br>qs to 100% | 50 | Domperidone maleate 1%<br>DURO-TAK ® 387-2516 60%<br>Polysorbate 80 20%<br>Dimethyl sulfoxide<br>qs to 100% |
| 51 | Domperidone maleate 1%<br>DURO-TAK ® 387-2516 55%<br>BRIJ ® S 20 So MH 5%<br>TRANSCUTOL ® 20%<br>Dimethyl sulfoxide<br>qs to 100% | 52 | Domperidone maleate 1%<br>DURO-TAK ® 387-2516 63%<br>BRIJ ® S 20 So MH 5%<br>Hexylene glycol 12%<br>Dimethyl sulfoxide<br>qs to 100% |
| 53 | Domperidone maleate 1%<br>DURO-TAK ® 387-2516 70%<br>BRIJ ® S 20 So MH 5%<br>BRIJ ® L4 LQ 5%<br>Dimethyl sulfoxide<br>qs to 100% | 54 | Domperidone maleate 1%<br>DURO-TAK ® 387-2516 55%<br>BRIJ ® S 20 So MH 5%<br>Diisopropyl adipate 20%<br>Dimethyl sulfoxide<br>qs to 100% |
| 55 | Domperidone maleate 1%<br>DURO-TAK ® 387-2516 65%<br>BRIJ ® S 20 So MH 5%<br>Lauryl lactate 10%<br>Dimethyl sulfoxide<br>qs to 100% | 56 | Domperidone maleate 1%<br>DURO-TAK ® 387-2516 54%<br>TRANSCUTOL ® 20%<br>BRIJ ® L4 LQ 5%<br>Dimethyl sulfoxide<br>qs to 100% |
| 57 | Domperidone maleate 1%<br>DURO-TAK ® 387-2516 62%<br>Hexylene glycol 12%<br>BRIJ ® L4 LQ 5%<br>Dimethyl sulfoxide<br>qs to 100% | 58 | Domperidone maleate 1%<br>DURO-TAK ® 387-2516 54%<br>Diethyl sebacate 20%<br>BRIJ ® L4 LQ 5%<br>Dimethyl sulfoxide<br>qs to 100% |
| 59 | Domperidone maleate 1%<br>DURO-TAK ® 387-2516 54%<br>Diisopropyl adipate 20%<br>BRIJ ® L4 LQ 5%<br>Dimethyl sulfoxide<br>qs to 100% | 60 | Domperidone maleate 1%<br>DURO-TAK ® 387-2516 64%<br>Lauryl lactate 10%<br>BRIJ ® L4 LQ 5%<br>Dimethyl sulfoxide<br>qs to 100% |
| 61 | Domperidone maleate 1%<br>DURO-TAK ® 387-2516 54%<br>TRANSCUTOL ® 10%<br>BRIJ ® L4 LQ 5%<br>Diethyl sebacate 10%<br>Dimethyl sulfoxide<br>qs to 100% | 62 | Domperidone maleate 1%<br>TRANSCUTOL ® 40%<br>BRIJ ® L4 LQ 5%<br>Diethyl sebacate 20%<br>Dimethyl sulfoxide<br>qs to 100% |
| 63 | Domperidone maleate 5%<br>TRANSCUTOL ® 40%<br>BRIJ ® L4 LQ 5%<br>Diethyl sebacate 20%<br>Dimethyl sulfoxide<br>qs to 100% | 64 | Domperidone maleate 10%<br>TRANSCUTOL ® 35%<br>BRIJ ® L4 LQ 5%<br>Diethyl sebacate 20%<br>Dimethyl sulfoxide<br>qs to 100% |
| 65 | Domperidone maleate 1%<br>DURO-TAK ® 387-2516 59%<br>TRANSCUTOL ® 5%<br>BRIJ ® L4 LQ 5%<br>Diethyl sebacate 5%<br>Limonene 5%<br>Dimethyl sulfoxide<br>qs to 100% | 66 | Domperidone maleate 1%<br>DURO-TAK ® 387-2516 74%<br>Limonene 5%<br>Dimethyl sulfoxide<br>qs to 100% |
| 67 | Domperidone maleate 1%<br>DURO-TAK ® 387-2516 64%<br>TRANSCUTOL ® 5%<br>BRIJ ® L4 LQ 5%<br>Diethyl sebacate 5%<br>Dimethyl sulfoxide<br>qs to 100% | 68 | Domperidone 1%<br>DURO-TAK ® 387-2516 64%<br>TRANSCUTOL ® 5%<br>BRIJ ®L4 LQ 5%<br>Diethyl sebacate 5%<br>Dimethyl sulfoxide<br>qs to 100% |

| Formulation | Formulation |
|---|---|
| 69 | Domperidone maleate 1%<br>DURO-TAK ® 387-2516 59%<br>TRANSCUTOL ® 5%<br>BRIJ ® L4 LQ 5%<br>Diethyl sebacate 5%<br>Limonene 5%<br>Dimethyl sulfoxide<br>qs to 100 |

One embodiment is a composition and method for treating gastroparesis with domperidone or deuterated domperidone or pharmaceutically acceptable salts thereof, provided in a sublingual dosage form. Examples of sublingual dosage forms include sublingual tablets, biocompatible thin films, and sublingual sprays. For example, sublingual tablets could be prepared as rapidly disintegrating tablets (RDT). RDT are solid dosage forms containing a medicament that rapidly (≤30 seconds) disintegrates when placed on or under the tongue, i.e., upon saliva contact. Formulation of domperidone or deuterated domperidone in RDT enables oral domperidone administration without water or without chewing. Commercially available RDT technologies are lyophilized tablets, compressed tablets, molded tablets, spray dried powders, thin films, and sugar-floss systems (McLaughlin et al., Pharmaceutical Technology, Supplement to September 2009 issue).

One embodiment is a composition and method for treating gastroparesis with domperidone or deuterated domperidone or pharmaceutically acceptable salts thereof, in a biocompatible nanoparticle formulation. In one embodiment, domperidone or deuterated domperidone is formulated for topical application. In one embodiment, domperidone or deuterated domperidone is formulated in and/or on a film, either directly or indirectly. For example, domperidone or deuterated domperidone may be formulated to be contained in the film matrix, or may be formulated as a layer of the film, or may be formulated in a vehicle that is applied to the film. The vehicle may be a suspension, foam, emulsion, etc. In one embodiment, domperidone or deuterated domperidone is formulated in a topically applied foam. In one embodiment, domperidone or deuterated domperidone is formulated in, on, or associated with a nanoparticle. In other embodiments, domperidone or deuterated domperidone is formulated as a solid tablet, or in a liquid such as a syrup, suspension, solution, or emulsion, or as an injectable.

Thin films formulations include, but are not limited to, those disclosed in U.S. Patent Publication Nos. 2014/0271788, 2014/0272220, 2014/0271787, 2014/0163060, 2014/0070440, 2014/0017299, 2013/0333831, and 2013/0220526.

Nanoparticle formulations include any nanosized structure that includes, but is not limited to, quantum dots including graphene quantum dots, graphene-oxide quantum dots, and graphene-zinc oxide quantum dots, nanotubes including graphene nanotubes and/or carbon nanotubes, fullerenes, buckyballs, dendrimers, liposomes, aptamers, micelles, etc.

The formulations provide ready patient compliance and optimal dose delivery for treating the symptoms of gastroparesis. It will be appreciated that other gastric motility disorders may also be treated with the disclosed compositions and methods.

In one embodiment, a domperidone or deuterated domperidone solution or suspension is put into a blister pack and lyophilized to prepare a unit dose. A lyophilized suspension may include regular particles, micronized particles, or nanoparticles. The following lyophilized technology platforms include ZYDIS® (Catalent), LYOC™ (Cephalon), PHARMAFREEZE® (SPI Pharmaceuticals), and QUICKSOLV® (Janssen).

For a lyophilized RDT product for sublingual administration domperidone or deuterated domperidone, as the active pharmaceutical ingredient (API), is dispersed in a matrix of a polymeric structure former, e.g., gelatin, and a saccharide, typically mannitol, dissolved in water. In the finished product, the glassy amorphous structure of the polymeric component imparts strength and resilience while retaining some flexibility. The specific gelatin grade and its associated dissolution characteristics ensure a smooth, rapid melt in the mouth. Mannitol crystallizes during freezing, providing an elegant appearance and rigidity and ensuring that the product is robust to handling and transport. Mannitol is readily soluble so also improves texture, taste, and mouthfeel. Domperidone or deuterated domperidone may be dissolved in the matrix or dispersed to form a homogenous suspension for dosing. Liquid dosing ensures good dose uniformity and accommodates extremely low-dose strengths, e.g., micrograms. Suspension dose strengths up to 400 mg can be accommodated, and domperidone or deuterated domperidone is typically micronized. Particle size is a consideration because particles >50 μm may feel gritty. Solution products, due to depression of freezing point by soluble API, can accommodate dose strengths up to 60 mg. Both solution and suspension based products use finely dispersed domperidone or deuterated domperidone in the dried unit, contributing to rapid dispersion and smooth mouthfeel. Other excipients, as subsequently described, may be included. Domperidone or deuterated domperidone is dispensed into preformed blister packs and rapidly cooled by liquid nitrogen for rapid freezing.

Freezing results in a network of ice crystals that are sublimed during lyophilization to produce a highly porous structure. The matrix components maintain the structure of the dried unit, but on contact with moisture, the high porosity results in rapid water penetration. The matrix quickly dissolves, resulting in fast disintegration (<10 seconds).

After freezing, the domperidone or deuterated domperidone is lyophilized, dosed, and dried in blister packs which are sealed providing physical and environmental protection. The product slightly adheres to the pack, resulting in minimum movement of the product within the blister pockets to ensure robustness during transport. The product is a wafer-like structure but of minimum friability and of sufficient strength to be removed from the pack without breakage.

The lyophilized RDT formulations' wafer-like structure and high porosity reflect that water is typically the major component of the dosing formulation, so the weight of the dried product is significantly reduced and often dictated primarily by the dose of domperidone or deuterated domperidone. The recommended 500 mg weight limit for RDT is likely approached for the highest domperidone or deuterated domperidone dose in lyophilized formulations, offset by its rapid disintegration.

After administration and rapid dispersion on or under the tongue, the lyophilized formulation effectively reverts to the original domperidone or deuterated domperidone solution or suspension. The lyophilized RDT tablet thus provides the convenience of a solid oral dosage form with the benefits of a solution/suspension product, suitability for buccal and sublingual uptake to enhance bioavailability directly into the systemic circulation and avoid first-pass metabolism to minimize undesirable metabolites, and physical and chemical stability with shelf life comparable to conventional tablets, i.e., 2-5 years.

QUICKSOLV® starts with an aqueous domperidone or deuterated domperidone and matrix component dispersion that is formed and frozen. Water is removed from the frozen matrix by either lyophilization or submersion in alcohol (solvent extraction) to produce a dry unit. The product formed has uniform porosity and adequate strength for handling, with properties similar to those previously described.

LYOC™ starts with an oil-in-water emulsion and is placed directly into blister cavities followed by freeze drying. To maintain homogeneity during freezing, polymers must be included to increase the matrix viscosity to an almost paste-like consistency to prevent sedimentation. The increased matrix viscosity reduces the product porosity, thereby increasing freeze drying times and having a negative impact on disintegration.

In one embodiment, a relatively low immediate release is the initial dose, followed by administration of an extended release formulation. In one embodiment 10 mg is the low immediate release dose followed by 20 mg-30 mg extended release over 24 h.

Unless otherwise indicated, a formulation is a dosage form. A tablet is a non-limiting example of a dosage form. Dispersion and disintegration of the formulation are used synonymously. As used herein, the active agent, abbreviated "active", includes domperidone, derivatives of domperidone, analogs of domperidone, deuterated domperidone, etc.

The active includes all forms of the domperidone active, including deuterated forms of domperidone, and also includes but is not limited to intermediates, metabolites, enantiomers, polymorphs, crystalline structure, hydrates, stereoisomers, salts, bases, complexes, carriers, analogs, derivatives, and conjugates. As used herein, extended release and sustained release are generally used synonymously.

Each of a bead and a pellet is any discrete component of a dosage form, e.g., a capsule shell may be filled with a plurality of beads and/or a plurality of pellets.

Modified release (MR) dosage forms include, but are not limited to, the following:

An immediate release formulation and a delayed release formulation indicate the onset of release of the active in relationship to administration. An immediate release formulation indicates release of the active from the formulation beginning within a relatively shorter period of time post administration, e.g. a few minutes or less. A delayed release formulation indicates release of the active from the formulation does not begin within a relatively shorter period of time after administration, but instead is delayed and begins or is triggered after a relatively longer period of time post administration, e.g., more than one hour.

A rapid release formulation and a slow release formulation indicate the rate of release after onset. Once delivery of the active begins, the active may be released relatively rapidly or relatively slowly. A rapid release indicates that, after onset, a maximum or peak dose is reached in a relatively shorter period of time. A slow release indicates that, after onset, a maximum or peak dose is reached in a relatively longer period of time. Once reached, the maximum dose may fall off at any rate, e.g. fast, slow, or constant.

A sustained release formulation and a continuous release formulation indicate the period of on-going release, and means that the delivery of active continues or is sustained for an extended period of time after initial onset, typically more than one hour, whatever the shape of the dose release profile. For example, the release of active is sustained between a maximum and minimum value of more than zero for some relatively longer period of time. This release may be at a constant dose, or at a dose that diminishes over time.

A constant release formulation indicates the dose that is being released. A constant release means that an active is delivered at a relatively constant dose over a moderate or extended period of time. This can be represented by a dose release profile that is relatively flat or only gently sloped after initial onset, i.e. without highly distinct peaks and valleys. Thus, a constant release is typically sustained or continuous, but a sustained or continuous release may not be constant.

A pulsed release formulation indicates that an active is delivered in one or more doses that fluctuate between a maximum dose and a minimum dose over a period of time. This can be represented by a dose release profile having one or more distinct peaks or valleys. However, two or more pulsed releases may produce an overlapping, overall, or composite release profile that appears to be or effectively is constant. When two or more pulsed releases occur, there may or may not be a period of no release between pulses. Typically, pulsed release results in release of essentially all of an active within about 60 minutes or less.

An extended release formulation provides either a release of active within a targeted dose range for a relatively longer period, or a plasma level of drug within a targeted dose range for a relatively longer period, without regard for the particular mechanism or character of release, e.g. as sustained, pulsed, or constant.

A release profile for an orally administered drug indicates the manner and timing by which a formulation releases or delivers the active to the stomach, intestines, etc. upon administration. Various methods are known to evaluate drug release and produce release profiles, including in vitro tests that model in vivo behavior of a formulation and that include USP dissolution testing for immediate release and controlled release solid dosage forms.

Drug release profiles are distinct from plasma profiles. A plasma profile indicates the dose or level of active in the bloodstream of a mammal, e.g. a patient receiving a drug formulation. When an active is released from a formulation, e.g. into the gut, the amount of active present in the bloodstream over time can be determined.

A drug release profile may be designed to produce a desired or targeted plasma profile, and a plasma profile may mimic a release profile. For example, while a sustained release of active would be expected to produce a sustained dose in the plasma, and a pulsed release would be expected to produce a pulsed (peak and valley) plasma profile, this is not necessarily the case. The half-life ($t_{1/2}$) of the active in the blood stream (its rate of decay) may be such that a sustained or continuous plasma profile could result from a pulsed delivery profile. Other factors may also play a role, such as bioabsorption, bioavailability, and first pass effect. The plasma profile produced by a particular active release profile may also vary from patient to patient.

Measures of bioavailability are known in the art and include the area under the plasma concentration-time curve (AUC), the concentration maximum ($C_{max}$), and the time to $C_{max}$ ($T_{max}$).

AUC measures the area under a plasma concentration-time curve, and represents the amount of drug absorbed following administration of a single dose of a drug (Remington: The Science and Practice of Pharmacy, Editor Gennaro 2000, p. 999).

$C_{max}$ is the maximum plasma concentration achieved after oral drug administration (Remington, page 999). An oral drug administration results in one $C_{max}$, but may result in more than one peak plasma concentration, e.g., following administration of a pulsed dose formulation.

$T_{max}$ is the amount of time necessary to achieve the $C_{max}$ after oral drug administration, and is related to the rate of absorption of the active (Remington p. 999).

A "solubility-enhancing polymer" or "crystallization-inhibiting polymer" refer to a water-soluble polymer capable, at suitable concentrations, of forming a solid dispersion, as defined herein, of a weakly basic meclizine in the solubility-enhancing polymer, e.g., by first dissolving both the drug and polymer in the same solvent system, and then removing the solvent under appropriate conditions. The weakly basic drug is maintained substantially as a molecular dispersion or in amorphous form during storage, transportation, and commercial distribution of the composition containing the solid dispersion of the solubility-enhancing polymer and weakly basic drug.

A "controlled-release" coating encompasses coatings that delay release, sustain release, prevent release, and/or otherwise prolong the release of a drug from a particle coated with a controlled-release coating. The term "controlled-release" encompasses "sustained-release," "delayed release" and "timed, pulsatile release," thus a "controlled-release coating" encompasses a sustained release coating, timed, pulsatile release coating or "lag-time" coating.

An "enteric polymer" refers to a pH sensitive polymer that is resistant to gastric juice (i.e., relatively insoluble at the low pH levels found in the stomach), and which dissolves at the higher pH levels found in the intestinal tract.

"Immediate release," in reference to a pharmaceutical composition that can be a dosage form or a component of a dosage form, refers to a pharmaceutical composition that releases greater than or equal to about 50% of the active, in another embodiment greater than about 75% of the active, in another embodiment greater than about 90% of the active, and in other embodiments greater than about 95% of the active within about one hour following administration of the dosage form. The term can also refer to pharmaceutical compositions in which the relatively rapid release of active occurs after a lag time in which little or no release of active occurs.

An "immediate release (IR) bead" or "immediate release particle" broadly refers to a bead or particle containing active that exhibits "immediate release" properties with respect to the active.

A "sustained release (SR) bead" or "sustained release particle" broadly refers to a bead or particle containing a SR coating disposed over an active-containing core.

A "lag-time coating" or "timed, pulsatile release coating" (TRP) refers to a controlled-release coating combining water-insoluble and enteric polymers; a TPR coating by itself provides an immediate release pulse of the active after a predetermined lag-time. A timed, sustained release (TSR) bead with a TPR coating disposed over a barrier coating (SR coating) provides a sustained active-release profile after a predetermined lag time.

A "delayed release (DR) bead" or "delayed release particle" broadly refers to an active-containing core. A DR coating refers to a controlled-release coating comprising an enteric polymer, optionally in combination with a plasticizer.

A "controlled release (CR) bead" or "controlled release particle" broadly refers to an active-containing core having an inner SR coating optionally followed by an outer DR or TPR coating or an inner TPR coating followed by an outer DR coating.

"Lag-time" refers to a time period where less than about 10% of the active is released from a pharmaceutical composition after ingestion of the composition or a dosage form comprising the composition, or after exposure of the composition or dosage form comprising the composition, to simulated body fluid(s), e.g., evaluated with a USP apparatus using a two-stage dissolution medium (first 2 hours in 700 mL of 0.1N HCl at 37° C. followed by dissolution testing at pH 6.8 obtained by the addition of 200 mL of a pH modifier).

"Disposed over", e.g. in reference to a coating over a substrate, refers to the relative location of e.g. the coating in reference to the substrate, but does not require that the coating be in direct contact with the substrate. For example, a first coating "disposed over" a substrate can be in direct contact with the substrate, or one or more intervening materials or coatings can be interposed between the first coating and the substrate. For example, a SR coating disposed over an active-containing core can refer to a SR coating deposited directly over the active-containing core or acid crystal or acid-containing core, or can refer to a SR coating deposited onto a protective seal coating deposited on the active-containing core.

A "sealant layer" or "protective seal coating" refers to a protective membrane disposed over an active-containing core particle or a functional polymer coating, protecting the particle from abrasion and attrition during handling, and/or minimizing static during processing.

An "orally disintegrating tablet" or "ODT" refers to a tablet that disintegrates rapidly in the oral cavity after administration without chewing. The disintegration rate can vary, but is faster than the disintegration rate of conventional solid dosage forms (e.g., tablets or capsules) that are intended to be swallowed immediately after administration, or faster than the disintegration rate of chewable solid dosage forms, when tested e.g. the USP <701> test method The term "substantially disintegrates" refers to a level of disintegration amounting to disintegration of at least about 50%, at least about 60%, at least about 70%, at least about 80%, at least about 90%, or about 100% disintegration. "Disintegration" is distinguished from "dissolution"; "disintegration" refers to the breaking up of or loss of structural cohesion of, e.g., the constituent particles comprising a tablet, whereas "dissolution" refers to the solubilization of a solid in a liquid, e.g., the solubilization of a drug in solvents or gastric fluids.

A "water-insoluble polymer" is a polymer that is insoluble or very sparingly soluble in aqueous media, independent of pH, or over a broad pH range (e.g., pH 0 to pH 14). A polymer that swells but does not dissolve in aqueous media can be "water-insoluble".

A "water-soluble polymer" is a polymer that is soluble, i.e., a significant amount dissolves, in aqueous media, independent of pH.

An "enteric polymer" is a polymer that is soluble, i.e., a significant amount dissolves, under intestinal conditions; i.e., in aqueous media under neutral to alkaline conditions and insoluble under acidic conditions (i.e., low pH).

A "reverse enteric polymer" or "gastro-soluble polymer" refers to a polymer that is soluble under acidic conditions and insoluble under neutral and alkaline conditions.

Unless stated otherwise, the amount of the various coatings or layers described herein (the "coating weight") is expressed as the percentage weight gain of the particles or beads provided by the dried coating, relative to the initial weight of the particles or beads prior to coating. Thus, a 10% coating weight refers to a dried coating which increases the weight of a particle by 10%.

Bioequivalence is the absence of a significantly different rate and extent of absorption in the availability of the active ingredient when administered at the same dose under similar conditions. Bioequivalence can be measured by pharmacokinetic parameters, e.g., AUC and $C_{max}$.

One embodiment is an oral formulation that contains a modified release formulation (MR). In this embodiment, a single dosage form contains both an immediate release (IR) dosage form and an extended release (XR) dosage form. As used herein, an immediate release dosage form releases active immediately upon administration. As used herein, an extended release dosage form encompasses delayed release, time release, controlled release, or sustained release forms. As used herein, an extended release dosage form releases active at a predetermined rate over time in order to maintain a constant drug concentration for a specific period of time with minimum side effects. Extended release formulations may be achieved by a variety of formulations as subsequently described with illustrative but not limiting examples, including polymer conjugates with the active and liposome formulations of the active.

The delivery system may comprise a core, seed, or matrix that may or may not be loaded with active, and one or more coating layers comprising active and/or comprising a layer having release characteristics that controls the onset and release characteristics of the active. The core, seed, or matrix may be prepared or obtained commercially. As only one example, there may be a sugar or microcrystalline cellulose core, with a hydrophilic matrix made from, e.g., hydroxypropyl methylcellulose (HPMC), hydroxypropyl cellulose (HPC), poly(ethylene oxide), poly(vinyl alcohol), xanthan gum, carbomer, carrageenan, zooglan, etc.

Coating layers can provide immediate release, delayed pulsed release, or sustained release. Immediate release of the active from the immediate-release layer can be by, e.g., using a very thin layer or coating that gastric fluids can quickly penetrate, facilitating rapid leaching of the active; or incorporating the active in a mixture that includes a supporting binder or other inert material that readily dissolves and release active in gastric fluid; or using a supporting binder or other inert material that rapidly disintegrates upon contact with gastric fluid, with both the material and the active quickly dispersing into gastric fluid as small particles. Such rapidly disintegrating and dispersing materials include, e.g., lactose and microcrystalline cellulose. Hydroxypropyl methylcellulose is an example of a suspending agent and binder.

Enteric coatings for the delayed pulsed release component can be pH-dependent or pH-independent. Enteric coatings for the sustained release component are pH dependent. A pH dependent coating is activated to release drug within a known pH range, which typically is matched to the local pH of the environment where delayed release is desired. Exemplary pH dependent coatings include cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, e.g., materials known under the trade name EUDRAGIT® L12.5, L100, or EUDRAGIT® S12.5, S100 or similar compounds used to obtain enteric coatings. Aqueous colloidal polymer dispersions or re-dispersions can be also applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and. 30DP (BASF); EASTACRYL® 30D (Eastman Chemical).

Examples of commercially available pharmaceutical formulations using an enteric system in the form of a coating or layer to prevent the active from dissolving in the stomach include CYMBALTA® (duloxetine HCl, Lilly Indianapolis Ind.), NEXIUM® (esomeprazole, AstraZeneca LP), ACIPHEX® (rabeprazole sodium, Eisai Inc. and Ortho-McNeil-Janssen Pharmaceuticals, Inc.), ASACOL® HD (mesalamine, Procter & Gamble Pharmaceuticals, Inc.), LIALDA® (mesalamine, Shire US), PENTASA® (me-salamine, Shire US), ENTECORT® EC (budesonide capsules, AstraZeneca), LAMICTAL® XR (lamotrigine tablets, GlaxoSmithKline), KAPIDEX® (dexlansoprazole, Takeda Pharmaceuticals North America, Inc.), CREON® (pan-creatin capsules, Solvay S.A), ULTRASE® (pancrelipase capsules, Axcan Pharma US), PROTONIX® (pantoprazole, Pfizer) DEPAKOTE® (divalproex sodium, Abbott Laboratories), PRILOSEC® (omeprazole, AstraZeneca), PREVACID® (lanzoprazole, Novartis Consumer Health), ARTHOTEC® (diclofenac sodium, Pfizer); STAVZOR® (valproic acid, Noven Therapeutics), TRILIPIXI 4 (fenofibric acid delayed release capsules, Abbott Laboratories), and VIDEX® EC (didanosine, Bristol-Myers Squibb).

An alcohol-resistant pharmaceutical composition uses an "alcohol protectant" to prevent or retard ethanol-induced "dumping" of the active agent from the dosage form that could cause too high of a dose of domperidone or deuterated domperidone to be released into the patient, which could then produce a higher $C_{max}$, potentially causing QT prolongation. With an alcohol-resistant composition, dose dumping is avoided, alleviating this safety concern. The alcohol protectant may be a single material, e.g. a polymer, or a combination of materials, e.g., combination of polymers, in an excipient solution. The alcohol protectant is deposited in a layer or coating, or it is in the form of a matrix in alternative embodiments. Alcohol protectant materials include, but are not limited to, organic based cellulose acetate phthalate, ammonium methacrylate copolymers, methacrylate ester copolymers, methacrylic acid copolymers, natural and synthetic starches, polyalkylene oxides, and natural and synthetic celluloses including modified celluloses such as hydroxypropylmethylcellulose (HPMC), hydroxypropylcellulose (HPC) hydroxymethylcellulose (HMC), methylcellulose (MC), hydroxyethylcellulose (HEC), and carboxymethylcellulose (CMC), waxes such as insect and animal waxes, vegetable waxes, mineral waxes, petroleum waxes, and synthetic waxes. In one embodiment, the alcohol protectant is an organic based cellulose acetate phthalate Eastman C-A-P® or Cellacefate, NF (Eastman Chemical Company, Kingsport Tenn. USA). The alcohol protectant may be present in the formulation in an amount sufficient to impart alcohol resistance at a given ethanol concentration, e.g., added in an amount of 20%, 25%, 30%, 35%, 40%, 45%, 50%, 55%, 60%, 65%, 70%, 75%, 80%, 85%, 90%, 95% 100%, 150%, 200%, 250%, 300%, 350%, 400%, 450% and 500% by weight gain.

In one embodiment, the active composition comprises a plurality of CR and IR particles, where the CR particles each comprises a core coated with a water-insoluble polymer layer, followed by a coating layer comprising an enteric polymer optionally in combination with a water-insoluble polymer, where the core comprises domperidone and a pharmaceutically acceptable polymeric binder, followed by a first coating layer comprising a water-insoluble polymer optionally in combination with a water-soluble polymer and an optional second coating of an enteric polymer optionally in combination with a water-insoluble polymer.

One embodiment has a plurality of CR and IR particles. The CR particle comprises a core coated with a water-insoluble polymer layer, followed by a coating layer comprising an enteric polymer optionally in combination with a water-insoluble polymer; the core comprising the active and a pharmaceutically acceptable organic acid (e.g. fumaric acid) separated from each other at least by a SR layer. The IR particles each comprise the active in combination with suitable excipients. In certain embodiments, the composition comprises the active and at least one solubility-enhancing organic acid that is capable of creating an acidic pH microenvironment within the coated bead to solubilize the active prior to its release into a hostile pH environment of the intestinal tract where the drug is practically insoluble.

In one embodiment, the CR particles comprise an inert core (e.g., a sugar sphere, cellulosic sphere, etc.) sequentially coated with a pharmaceutically acceptable organic acid (e.g., succinic acid) and a pharmaceutically acceptable binder (e.g., hydroxypropyl cellulose); a SR layer (e.g., comprising a pharmaceutically acceptable water insoluble polymer such as ethyl cellulose, optionally plasticized with a pharmaceutically acceptable plasticizer such as triethyl citrate or polyethylene glycol); a active layer, and a pharmaceutically acceptable binder (e.g., povidone); an optional sealing layer (e.g. comprising a water soluble polymer such as hydroxypropyl methyl cellulose); and a SR layer comprising a water insoluble polymer such as ethyl cellulose (EC-10), and an enteric polymer such as hypromellose phthalate, HP-55, and an optional pharmaceutically acceptable plasticizer such as triethyl citrate (TEC).

A pH independent coating includes materials susceptible to enzymatic activation by azo-reductases in intestinal bacteria (i.e., azo-polymers) or materials susceptible to degradation by polysaccaridases in the colon (natural polysaccarides). Non-limiting examples of azo-polymers include co-polymers of 2-hydroxyethyl methacrylate (HEMA) and methyl methacrylate (MMA). Non-limiting examples of natural polysaccharides include amylose, chitosan, chrondoitin, dextran, and xylan.

An "enteric polymer" is a polymer having a polystyrene equivalent weight average molecular weight (MW) of about 50,000 to 150,000, and containing carboxyl groups that remain insoluble at a pH below about pH 4 (gastric pH range), but that ionize, and thus cause the polymer to dissolve, at a pH above about 5.0 (intestinal pH range). The enteric polymer may be film-forming, e.g., cellulose acetate phthalate (C-A-P), cellulose acetate trimellitate (C-A-T), hydroxypropylmethylcellulose phthalate (HPMCP), copolymer of methacrylic acid and ethyl acrylate, hydroxypropylmethyl-cellulose acetate succinate (HPMCAS), and polyvinyl acetate phthalate (PVAP). The MW of HPMCP may be between about 80,000 and 110,000, or between 95,000 and 100,000. The MW for C-A-P may be between about 55,000 and 75,000, or between 68,000 and 80,000.

The sustained release component can include sustained release coatings, sustained release matrices, and sustained release osmotic systems. Sustained release coatings can be prepared using a water-insoluble polymer, a combination of water-insoluble polymers, or a combination water-insoluble and water-soluble polymers. Conventional sustained release polymers are known to those of ordinary skill in the art can be used for the sustained release matrix.

Exemplary sustained release coatings include polyvinyl acetate, cellulose acetate, cellulose acetate butyrate, cellulose acetate propionate, ethyl cellulose, fatty acids and esters thereof, alkyl alcohols, waxes, zein (prolamine from corn), and aqueous polymeric dispersions such as EUDRAGIT® RS and RL30D, EUDRAGIT® NE30D, AQUACOAT®, SURELEASE®, KOLLICOAT® SR30D, and cellulose acetate latex.

Pellets or beads can be made of any pharmaceutically acceptable materials, based on compatibility with the active and the physicochemical properties of the pellets or beads.

Binders include cellulose derivatives such as methylcellulose, hydroxyethyl cellulose, hydroxypropyl cellulose, hydroxypropyl methylcellulose, polyvinylpyrrolidone, polyvinylpyrrolidone/vinyl acetate copolymer, etc.

Disintegration agents include corn starch, pregelatinized starch, cross-linked carboxymethylcellulose (AC-DI-SOL®), sodium starch glycolate (EXPLOTAB®), cross-linked polyvinylpyrrolidone (PLASDONE XL®), etc.

Filling agents include lactose, calcium carbonate, calcium phosphate, calcium sulfate, microcrystalline cellulose, dextran, starches, sucrose, xylitol, lactitol, mannitol, sorbitol, sodium chloride, polyethylene glycol, etc.

Surfactants include sodium lauryl sulfate, sorbitan monooleate, polyoxyethylene sorbitan monooleate, bile salts, glyceryl monostearate, PLURONIC® line (BASF), etc.

Solubilizers include citric acid, succinic acid, fumaric acid, malic acid, tartaric acid, maleic acid, glutaric acid, sodium bicarbonate, sodium carbonate, etc.

Stabilizers include antioxidation agents, buffers, acids, etc.

The following information illustrates exemplary but non-limiting manufacturing methods.

The core may be prepared by extrusion-spheronization, high-shear granulation, solution or suspension layering, In extrusion-spheronization, the active and other additives are granulated by adding a binder solution. The wet mass is passed through an extruder equipped with a certain size screen. The extrudates are spheronized in a marumerizer. The resulting pellets are dried and sieved.

In high-shear granulation, the active and other additives are dry-mixed, then the mixture is wetted by adding a binder solution in a high shear-granulator/mixer. The granules are kneaded after wetting by the combined actions of mixing and milling. The resulting granules or pellets are dried and sieved.

In solution or suspension layering, a drug solution or dispersion with or without a binder is sprayed onto starting seeds with a certain particle size in a fluid bed processor or other suitable equipment, thus coating the active on the surface of the starting seeds. The active-loaded pellets are dried.

Core particles have a diameter ranging from about 50 microns-1500 microns, preferably 100 microns-800 microns. Core particles may be coated in a fluidized bed apparatus with an alternating sequence of coating layers. The core may be coated directly with a layer or layers of the active, and/or the active may be incorporated into the core material. A separation or protective layer may be added on top of the active containing layer, and/or between active layers. A separation or protective layer may be added onto the surface of the active-loaded core, and then the enteric delayed pulsed or sustained release layer may be coated thereupon. Another active layer may also be added to the enteric delayed pulsed or sustained layer to deliver an initial dose. A protective coating layer may be applied immediately outside either an active-containing core or an active-layered core, by conventional coating techniques used in the art, such as pan coating or fluid bed coating, using solutions of polymers in water or suitable organic solvents, or aqueous polymer dispersions. Suitable materials for the protective layer include cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions (AQUACOAT®, SURELEASE®), EUDRAGIT® RL 30D, OPADRY®, cellulose acetate, cellulose acetate butyrate, cellulose acetate propionate, ethyl cellulose, fatty acids and their esters, waxes, zein, and aqueous polymer dispersions such as EUDRAGIT® RS and RL 30D, EUDRAGIT® NE 30D, AQUACOAT®, SURELEASE®, and/or cellulose acetate latex, alone or combined with hydrophilic polymers such as hydroxyethyl cellulose, hydroxypropyl cellulose (KLUCEL®, Hercules Corp.), hydroxypropyl methylcellulose (METHOCEL®, Dow Chemical Corp.), polyvinylpyrrolidone, etc. Coating levels range from about 1% w/w to about 6% w/w, preferably about 2% w/w to about 4% w/w.

The enteric delayed pulsed release or sustained release coating layer is applied to the core, with or without seal coating, by conventional coating techniques known in the art, e.g., pan coating or fluid bed coating, using solutions of polymers in water or suitable organic solvents, or using aqueous polymer dispersions. Suitable coaters are known in the art, e.g., commercially available pH-sensitive polymers so that the active is not released in the acidic stomach environment (pH<4.5), but is released and become available when the pH-sensitive layer dissolves at a higher pH, after a certain delayed time, or after the unit passes through the stomach.

Enteric polymers for the delayed pulsed release component and sustained release component include, e.g., cellulose acetate phthalate, cellulose acetate trimellitate, hydroxypropyl methylcellulose phthalate, polyvinyl acetate phthalate, carboxymethylethylcellulose, co-polymerized methacrylic acid/methacrylic acid methyl esters such as, e.g., materials known as EUDRAGIT® L12.5, L100, or EUDRAGIT® S12.5, S100 or similar compounds used to obtain enteric coatings. Aqueous colloidal polymer dispersions or re-dispersions can be also applied, e.g. EUDRAGIT® L 30D-55, EUDRAGIT® L100-55, EUDRAGIT® S100, EUDRAGIT® preparation 4110D (Rohm Pharma); AQUATERIC®, AQUACOAT® CPD 30 (FMC); KOLLICOAT MAE® 30D and. 30DP (BASF); EASTACRYL® 30D (Eastman Chemical).

The enteric delayed pulsed release and sustained release polymers can be modified by mixing with other known coating products that are not pH sensitive, e.g., neutral methacrylic acid esters with a small portion of trimethylammonioethyl methacrylate chloride commercially available as EUDRAGIT® RS and EUDRAGIT® RL; a neutral ester dispersion without any functional groups commercially available as EUDRAGIT® NE30D; and other pH independent coating products.

The modifying component of the protective layer used over the enteric delayed pulsed release or sustained release coating can include a water penetration barrier layer (semipermeable polymer) that can be successively coated after the enteric coating to reduce the water penetration rate through the enteric coating layer and thus increase the lag time of the active release. Coating is performed as previously described.

An protective or colorant overcoating layer can optionally be applied. OPADRY®, OPADRY II® (COLORCON®) and corresponding color and colorless grades from COLORCON® can protect the pellets from being tacky and provide colors to the product. In one embodiment the protectant or color coating ranges from 1% w/w to 6% w/w, preferably about 2% w/w to about 3% w/w. Talc can also be used.

Components may be incorporated into the overcoating formula, e.g., to facilitate and provide even more rapid release. Such components include, e.g., plasticizers including acetyltriethyl citrate, triethyl citrate, acetyltributyl citrate, dibutylsebacate, triacetin, polyethylene glycols, propylene glycol, etc.; lubricants including talc, colloidal silica dioxide, magnesium stearate, calcium stearate, titanium dioxide, magnesium silicate, etc.

The composition may be incorporated into hard gelatin capsules, either alone or with additional excipients. The composition may be incorporated into a tablet, e.g., by incorporation into a tablet matrix that rapidly disperses the particles after ingestion. To prevent particle destruction during the tableting process, a filler/binder is required, e.g., microcrystalline cellulose (AVICEL®), soy polysaccharide (EMCOSOY®), pre-gelatinized starches (STARCH® 1500, NATIONAL® 1551), and polyethylene glycols (CARBOWAX®), present in the range of about 5% w/w to about 75% w/w, with a preferred range of about 25% w/w to about 50% w/w.

Excipients typically include, but are not limited to, one or more inert fillers including microcrystalline cellulose, soy polysaccharides, calcium phosphate dihydrate, calcium sulfate, lactose, sucrose, sorbitol, etc.; one or more materials that impart flow to powders including fumed silicon dioxide, silica gel, magnesium stearate, calcium stearate, etc.; one or more lubricants to insure proper tableting including polyethylene glycol, leucine, glyceryl behenate, magnesium stearate, calcium stearate, stearic acid, hydrogenated vegetable oil, etc. present in the range of about 0.1% w/w to about 10% w/w, with a preferred range of about 0.3% w/w to about 3.0% w/w.

Disintegrants are added to disperse the beads once the tablet is ingested. Disintegrants include, but are not limited to, cross-linked sodium carboxymethyl cellulose (AC-DI-SOL®), sodium starch glycolate (EXPLOTAB®, PRIMOJEL®), cross-linked polyvinylpolypyrrolidone (PLASDONE-XL®), etc., present in the range of about 3% w/w to about 15% w/w, with a preferred range of about 5% w/w to about 10% w/w.

In one embodiment, tablets are formed from particles that are introduced into a blender with AVICEL®, disintegrants, and lubricant, mixed for a defined time (minutes) to achieve a homogeneous blend, then the blend is placed in the hopper of a tablet press with which tablets are compressed. The compression force used is adequate to form a tablet but not to fracture the beads or coatings.

A tablet can be constructed in three layers, where the immediate release component is dry blended, and the delayed pulsed release and the sustained release components are wet granulated. The tablet is then formed in a one layer or a three layer compression. Upon dissolution of layers, each component is released and acts as formulated: e.g., the immediate release particles provide immediate release, the delayed pulsed release particles provide delayed pulsed release, and the sustained release particles provide sustained release after a lag time.

One embodiment of the invention is an oral domperidone or deuterated domperidone formulation that contains, in a single dosage form, both an immediate release form and an extended release form. One embodiment of the invention is an oral domperidone or deuterated domperidone formulation that contains, in a single dosage form, both an immediate release form and an extended release form.

A dosage form of domperidone or deuterated domperidone that combines both an immediate release formulation of 10 mg, ranging from 5 mg to 20 mg, and an extended release formulation of 20 mg, ranging from 10 mg to 80 mg, provides agent delivery to the patient continuously over about a 12 hr period. Such a dosage formulation provides therapy over 12 hrs with a single patient dosage, providing patient convenience and extended therapy, e.g., a patient may beneficially experience a complete night of sleep, a complete work day, a complete leisure day, etc. without symptoms.

In embodiments, the inventive formulation contains an immediate release (IR) portion or component of the composition, and an extended release (XR) portion or component, or combinations thereof. The immediate release portion delivers 100% of the immediate release dose in less than about hour, and the extended release portion delivers the extended release dose over a period of 12 hours.

Figure 2:
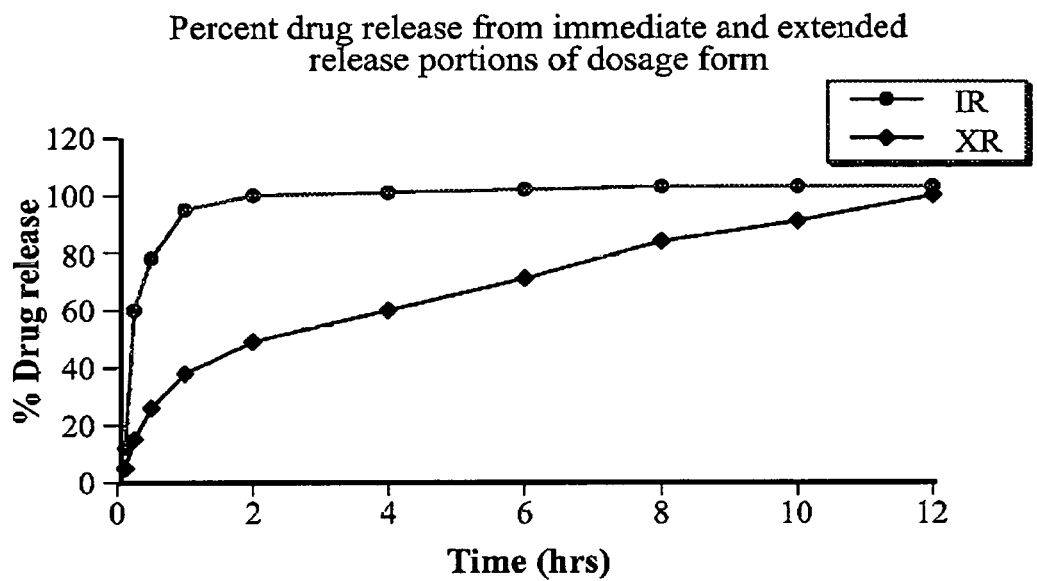
FIG. 2 shows a representative drug release profile for an immediate release (IR) formulation and an extended release (XR) formulation.
Figure 3:
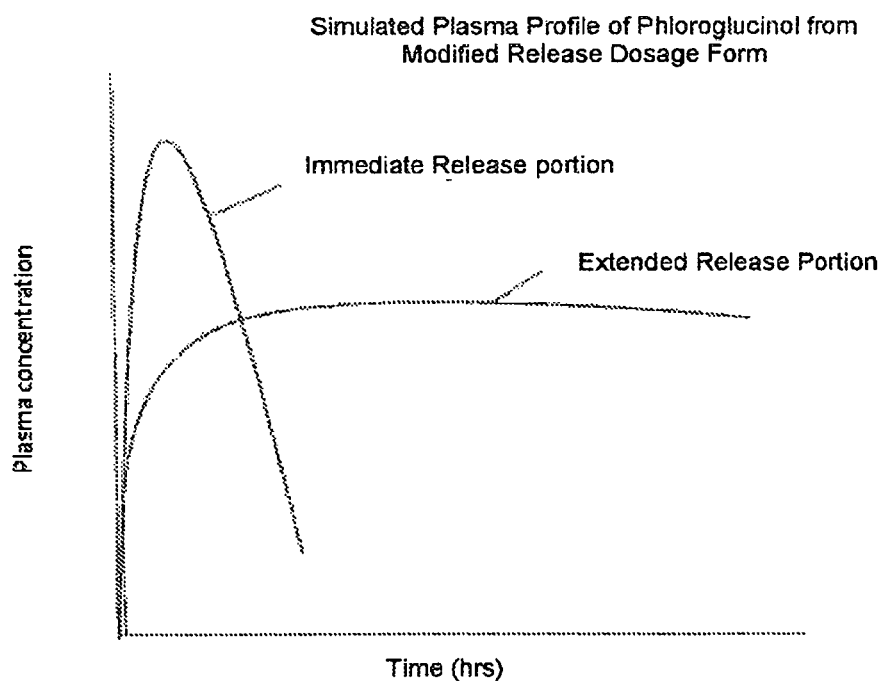
FIG. 3 is a simulated plasma profile of deuterated domperidone from an immediate release portion and an extended release portion.

A typical dissolution profile, also termed a release profile, of domperidone is shown in FIG. 2. The percent of drug release approaches 100% in less than or within one hour in the immediate release portion of the delivery system, and about 100% within or less than 12 hours for the extended release portion of the delivery system. FIG. 3 is a schematic of a simulated plasma concentration of domperidone, where the plasma drug concentration from the immediate release portion peaks at about twice the concentration at the same time the drug from the extended release portion reaches a plateau, about half of that from the immediate release portion.

In one embodiment, the active may be administered rectally. Rectal administration of the active may be 10 mg-20 mg three times daily. Rectal administration may be by a suppository formulation. In one embodiment, the formulation is administered rectally, e.g., by suppository.

The composition may take a variety of delivery forms or systems. The following formulations may be used, these are exemplary only and non-limiting. Oral formulations include a tablet, capsule, sachet, soft gel, liquid, gel, strip, film, powder, granule, gel, pulsatile release, coated core, delayed extended release form, banded drug form, sustained release form, tablet capsule, granulation caplet, layered tablet, etc., including combinations of these, e.g., a tablet capsule, a granulation caplet, a layered tablet, etc. with active and at least one pharmaceutically acceptable excipient.

Figure 4:
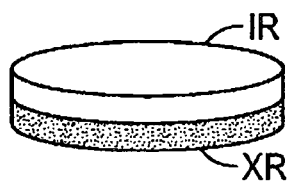
FIG. 4 shows a bilayer tablet with IR and ER layers.
Figure 5:
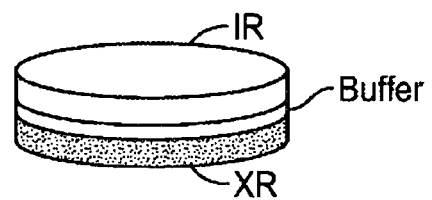
FIG. 5 shows a trilayer tablet containing IR, ER, and a buffer layer.
Figure 6:
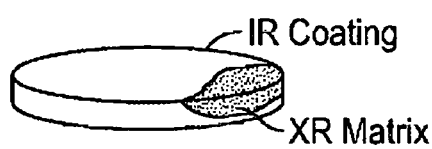
FIG. 6 shows a tablet with an ER matrix and an IR coating.

A tablet formulation is known to one skilled in the art. The tablet may be of any shape or size convenient for oral administration, e.g., circular, elliptical, etc. In one embodiment, the tablet may be either for immediate release (IR), extended release (XR), or combinations thereof. The tablet may be a bilayer tablet containing IR and XR layers adjacent to each other (FIG. 4); a trilayer tablet containing both IR and XR layers separated by a pharmaceutically acceptable buffer layer (FIG. 5); or a XR tablet containing the active in the matrix layer and coated with an IR layer of active (FIG. 6).

Figure 7:
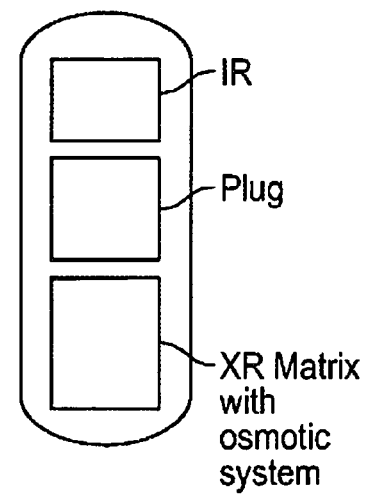
FIG. 7 shows a capsule containing an IR tablet, a plug, and an ER tablet with an osmotic system.
Figure 8:
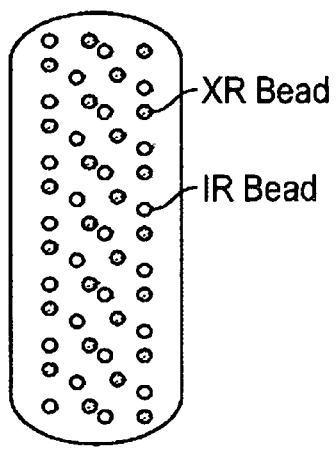
FIG. 8 shows a capsule containing IR and ER beads.
Figure 9:
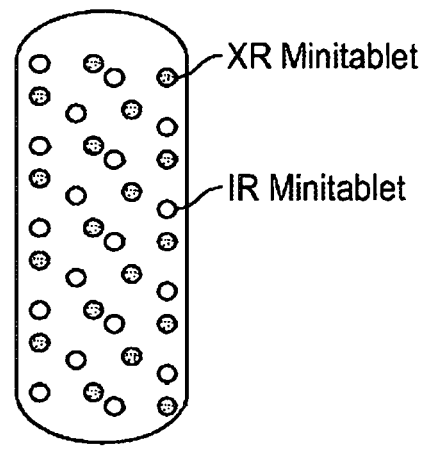
FIG. 9 shows a capsule containing IR and ER mini-tablets.
Figure 10:
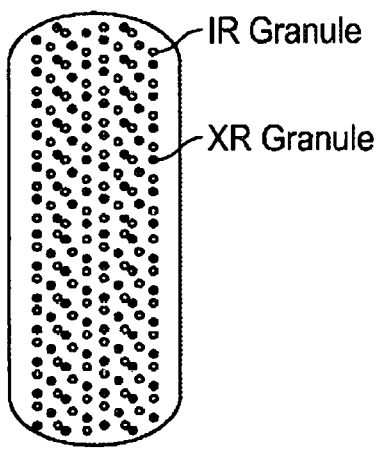
FIG. 10 shows a capsule containing IR and ER granules.
Figure 11:
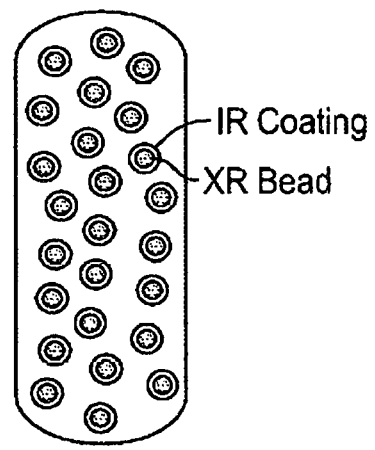
FIG. 11 shows a capsule containing an ER bead coated with an IR layer.
Figure 12:
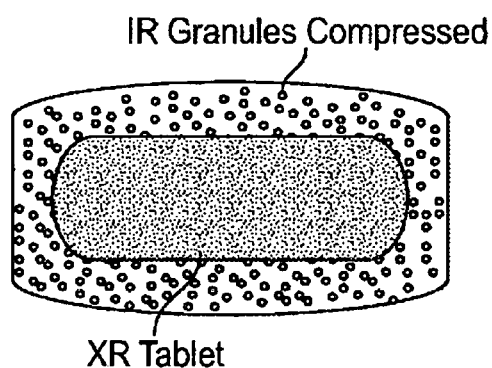
FIG. 12 shows a compressed tablet containing IR granules and a coated ER tablet embedded within the compressed tablet.
Figure 13:
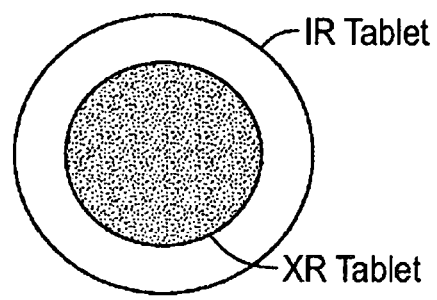
FIG. 13 shows a compressed IR tablet with an ER tablet embedded within the IR tablet.
Figure 14:
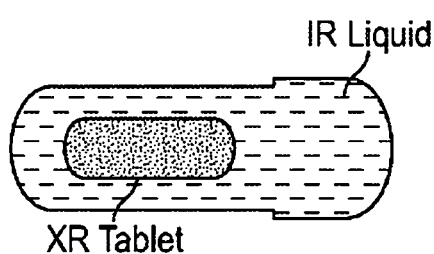
FIG. 14 shows an ER tablet suspended in an IR liquid.

The composition may also be provided in other delivery forms, e.g., a capsule containing an IR tablet, a plug, and a XR tablet within an osmotic drug delivery system for controlled delivery of the composition over a duration of 12 hours (FIG. 7); a capsule containing IR beads and XR beads mixed in the appropriate ratios (FIG. 8); a capsule containing IR mini-tablets mixed with XR mini-tablets (FIG. 9); a capsule containing IR granules and XR granules that are coated with extended release polymers (FIG. 10); a capsule containing XR beads that are coated with a IR layer (FIG. 11), etc. Other delivery forms of the active may be a compressed tablet containing IR granules and coated XR beads that are embedded within the tablet (FIG. 12); a compressed tablet containing a XR tablet embedded within the IR tablet (FIG. 13); or a XR tablet suspended in an immediate release liquid drug solution within a capsule (FIG. 14).

Figure 15:
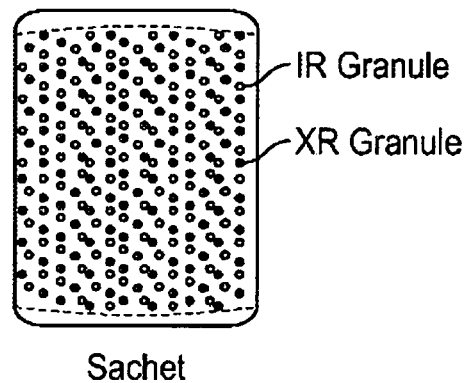
FIG. 15 shows a sachet containing a mixture of IR and ER granules or beads.
Figure 16:
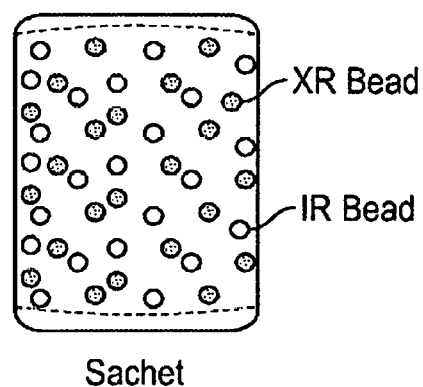
FIG. 16 shows a sachet containing effervescent IR granules or beads and coated ER granules or beads.

Another delivery form is a sachet. A sachet may contain a mixture of IR and XR granules or beads (FIG. 15), or it may contain a mixture of effervescent IR granules and coated XR granules (FIG. 16).

Other immediate, extended, or sustained, modified, and delayed pulse release systems are described in each of the following references U.S. Publication Nos. 2005/0095295, 2005/0106247, and 2007/0264323; and U.S. Pat. Nos. 6,126,969 and 8,211,465. As one example, U.S. Publication No. 2005/0106247 describes a drug (cyclobenzaprine hydrochloride) in extended release particles such as beads, pellets, granules, etc. having an extended release coating comprising a water insoluble polymer, and/or water soluble polymer, and some of the particles are contained in a gelatin capsule. As another example, U.S. Publication No. 2007/0264323 describes delivery systems for a drug (ADDERALL®) such as beads within capsules, tablets, or sachets including coating layers, delayed pulsed release components, immediate release formulations, intermediate release formulations, sustained release formulations, and controlled release capsules. U.S. Pat. No. 6,126,969 describes delivery systems for a drug (acetaminophen) such as a combination of coated and uncoated drug particles for an immediate-release/sustained release dosage form. U.S. Pat. No. 8,211,465 describes dosage forms for an initial release of a drug (NSAID such as ibuprofen) and a second sustained release of the same drug. An osmotic delivery system is described in Patra et al. Osmotic Drug Delivery Systems: Basis and Design Approaches, Recent Patents on Drug Delivery and Formulation, 7 (2013) 1-12.

The active core of the dosage form may be an inert particle or an acidic or alkaline buffer crystal, which is coated with a drug-containing film-forming formulation. In one embodiment a water-soluble film forming composition forms a water-soluble/dispersible particle. Alternatively, the active may be prepared by granulating and milling and/or by extrusion and spheronization of a polymer composition containing the active. The amount of active in the core depends on the dose that is required, and typically varies from about 5 weight % to 60 weight %. The polymeric coating on the active core will typically be from about 4% to 20% based on the weight of the coated particle, depending on the type of release profile required and/or the selected polymers and coating solvents. Those skilled in the art will be able to select an appropriate amount of active for coating onto or incorporating into the core to achieve the desired dosage. In one embodiment, the inactive core may be a sugar sphere or a buffer crystal or an encapsulated buffer crystal such as calcium carbonate, sodium bicarbonate, fumaric acid, tartaric acid, etc. which alters the microenvironment of the active to facilitate its release.

The drug-containing particle may be coated with an extended release (XR) coating comprising a water insoluble polymer or a combination of a water insoluble polymer and a water soluble polymer to provide XR beads. In embodiments, the water insoluble polymer and the water soluble polymer may be present at a weight ratio of from 100:0 to 65:35, or from about 95:5 to 70:30, or from about 85:15 to 75:25. The extended release coating is applied in an amount necessary to provide the desired release profile. In embodiments, the extended release coating is from about 1% to 15% by weight of the coated beads, or from about 7% to 12% by weight of the coated beads.

The modified release dosage form, including a mixture of two bead populations, may be made as follows. A drug-containing core is prepared by coating an inert particle, such as a non-pareil seed, an acidic buffer crystal or an alkaline buffer crystal with an active and a polymeric binder or by granulation and milling or by extrusion/spheronization to form an IR bead. The IR bead is coated with a plasticized water-insoluble polymer alone such as ethylcellulose or in combination with a water soluble polymer such as hydroxypropylmethylcellulose to form an XR bead. Hard gelatin capsules XR beads, alone or combined with IR beads, are filled at a desired ratio to produce modified release (MR) capsules providing the desired release profile.

IR beads using the following dissolution procedure have been reported to release at least about 70%, more specifically at least about 90%, of the active within 30 minutes.

A USP Apparatus 2 (paddles at 50 rpm) is used with the following dissolution medium: 900 mL 0.1 N HCl (or suitable dissolution medium) at 37° C., with active release determined by HPLC.

An aqueous or a pharmaceutically acceptable solvent may be used for preparing active-containing core particles. The type of film forming binder that is used to bind the drug to the inert sugar sphere is not critical but usually water soluble, alcohol soluble, or acetone/water soluble binders are used. Binders such as polyvinylpyrrolidone (PVP), polyethylene oxide, hydroxypropyl methylcellulose (HPMC), hydroxypropylcellulose (HPC), polysaccharides such as dextran, corn starch may be used at concentrations from about 0.5 weight % to about 5 weight %, with other concentrations also being used. The active may be present in this coating formulation in the solution form or may be dispersed at a solid content up to about 35 weight % depending on the viscosity of the coating formulation.

The active, optionally a binder such as PVP, a dissolution rate controlling polymer if used, and optionally other pharmaceutically acceptable excipients are blended in a planetary mixer or a high shear granulator such as FIELDER® and granulated by adding/spraying a granulating fluid such as water or alcohol. The wet mass can be extruded and spheronized to produce spherical particles (beads) using an extruder/marumerizer. In these embodiments, the active load may be as high as 90% by weight based on the total weight of the extruded/spheronized core.

Illustrative but not limited examples of water insoluble polymers useful in the XR coating include ethylcellulose powder or an aqueous dispersion (e.g., AQUACOAT® ECD-30), cellulose acetate, polyvinyl acetate (KOLLICOAT® SR 30D, BASF), neutral copolymers based on ethyl acrylate and methylmethacrylate, copolymers of acrylic and methacrylic acid esters with quaternary ammonium groups such as EUDRAGIT® NE, RS and RS30D, RL or RL30D, etc. Illustrative but not limiting water soluble polymers include low molecular weight hydroxypropyl methylcellulose (HPMC), methylcellulose, hydroxypropylcellulose, polyvinylpyrrolidone, and/or polyethylene glycol (PEG) of molecular weight >3000). The extended release coating is typically applied at a thickness ranging from about 1 weight % up to 15 weight % depending on the solubility of the active in water and the solvent or latex suspension based coating formulation used.

The coating compositions used in forming the membranes are usually plasticized. Illustrative but not limiting plasticizers include triacetin, tributyl citrate, triethyl citrate, acetyl tri-n-butyl citrate diethyl phthalate, polyethylene glycol, polypropylene glycol, castor oil, dibutyl sebacate, and/or acetylated monoglycerides, etc. The plasticizer may comprise about 3 weight % to about 30 weight %, more typically about 10 weight % to about 25 weight % based on the polymer. The type of plasticizer and its content depends on the polymer or polymers and nature of the coating system (e.g., aqueous or solvent based, solution or dispersion based and the total solids).

The particle may be primed by applying a thin hydroxypropyl methylcellulose (HPMC)(OPADRY® Clear) film before applying an extended release membrane coating to separate the different membrane layers. HPMC is typically used, but other primers such as hydroxypropylcellulose (HPC) can also be used.

The membrane coatings can be applied to the core using any coating techniques used in the pharmaceutical industry. In one embodiment, fluid bed coating is used.

Multi-dose forms may be used, i.e., products in the form of multi-particulate dosage forms (pellets, beads, granules, mini-tablets, etc.) or in other forms suitable for oral administration. As used herein, these terms are used interchangeably to refer to multi-particulate dosage forms.

An extended release dosage form that includes a mixture of two or more bead populations can be made as follows. An inert particle such as a non-pareil seed, an acidic buffer crystal, or an alkaline buffer crystal is coated with an active and a polymeric binder to form an active particle, i.e., immediate release (IR) bead, that may be in the unit dosage form to act as a bolus dose. The active particle is coated with a solution or suspension of a water insoluble polymer or a mixture of water soluble and water insoluble polymers to form an extended release coated active particle, i.e., extended release (XR). Hard gelatin capsule XR beads alone and optionally, in combination with IR beads at a ratio ranging from 95:5 to 70:30 (ER beads:IR beads), are filled to produce a modified release (MR) capsule exhibiting a target active release profile.

In one embodiment, the dosage form has an immediate release portion of active dispersed in an oily or lipid system, and another portion that is formulated in a waxy matrix or particles of active coated with hydrophobic carriers. At least 15%-50% of the active is an immediate release portion and is in a dosage form suitable for immediate release. The remainder of the tablet capsule, by weight, can include a sustained release formulation of active or a portion of the sustained release formulation of active.

The active domperidone or deuterated domperidone may be formulated in a lipid-based delivery system. Encapsulating or solubilizing the active in lipid excipients can lead to increased solubilization and absorption resulting in enhanced bioavailability.

Lipid excipients are commercially available. Because lipids affect absorption, it is necessary to know lipid excipient characteristics. Factors that determine the choice of excipients for lipid-based formulations include miscibility, solvent capacity, self-dispersibility and ability to promote self-dispersion of the formulation, digestibility and fate of digested products, irritancy, toxicity, purity, chemical stability, capsule compatibility, melting point, cost, etc.

Dietary oils composed of medium and long chain triglycerides, along with various solvents and surfactants, are frequently used to prepare lipid-based formulation. Many lipids are amphiphilic, i.e., they have a lipophilic portion (fatty acid) and a hydrophilic portion. The melting point increases as the fatty acid chain length increases, but the melting point decreases with an increase in the unsaturation of the fatty acid which also increases susceptibility to oxidation. Solubilizing agents used in lipid-based formulations are provided in the following table:

| Solubilizing excipients used in commercially available lipid-based oral formulations | | |
|---|---|---|
| Water-insoluble excipients | Triglycerides | Surfactants |
| Bees wax | Long-chain triglycerides | Polysorbate 20 (TWEEN® 20) |
| Oleic acid | Hydrogenated soybean oil | Polysorbate 80 (TWEEN® 80) |
| Soy fatty acids | Hydrogenated vegetable oil | Sorbitanmonolaurate (SPAN® 20) |
| D-α-Tocopherol (vitamin E) | Corn oil, Olive oil, | D-α-Tocopherol PEG 1000 succinate (TPGS) |
| Corn oil mono-di-triglycerides | Soybean oil, Peanut oil | Glycerylmonooleate |
| Medium chain (C8/C10) mono and diglycerides | Sesame oil | Polyoxyl 35 castor oil (CREMOPHOR® EL) |
| Propylene glycol esters of fatty acids | Medium-chain triglycerides | Polyoxyl 40 hydrogenated castor oil (CREMOPHOR® RH40) |
| | Caprylic/capric triglycerides derived from coconut oil or palm seed oil | Polyoxyl 60 hydrogenated castor oil (CREMOPHOR® RH60) |
| | | PEG 300 oleic glycerides (LABRAFIL® M-1944CS) |
| | | PEG 300 linoleic glycerides (LABRAFIL® M-2125CS) |
| | | PEG 400 caprylic/capric glycerides (LABRASOL®) |
| | | PEG 1500 lauric glycerides (GELUCIRE® 44/14) |

Triglyceride vegetable oils are the most common lipid excipients. They are fully digested and absorbed, eliminating safety issues. Triglycerides are long chain triglycerides (LCT), medium chain triglycerides (MCT) and short chain triglycerides (SCT). Their solvent capacity for an active is mainly due to the effective concentration of ester groups. MCT have a higher solvent capacity than LCT and are less prone to oxidation. Oils from different vegetable sources have different proportions of each fatty acid. The fatty acid composition in various lipid excipients is shown below.

Composition of fatty acids found in lipid-based excipients:

| Fatty acid chain length (number of carbons) | Common Name | Melting temperature (° C.) |
|---|---|---|
| 8 | caprylic acid | 16.5 |
| 10 | capric acid | 31.6 |
| 12 | lauric acid | 44.8 |
| 14 | myristic acid | 54.4 |
| 16 | palmitic acid | 62.9 |
| 18 | stearic acid | 70.1 |
| 18 | oleic acid | 16.0 |
| 18 | linoleic acid | −5.0 |
| 18 | γ-linoleic acid | −11.0 |
| 18 | ricinoleic acid | 6.0 |
| 20 | arachidic acid | 76.1 |
| 22 | behenic acid | 80.0 |

D-α-tocopherol polyethylene glycol 1000 succinate (Vitamin E TPGS) is derived from vegetable tocopherols. It is water soluble and acts as absorption enhancer for poorly water-soluble drugs. Pure triglycerides are presented in refined vegetable oils.

Mixed glycerides are obtained by partial hydrolysis of vegetable oils. The triglyceride starting material and the extent of hydrolysis determine the chemical composition of the mixed glycerides produced. Medium chain mixed glycerides are not susceptible to oxidation, have greater solvent capacity, and promote emulsification. These polar oily excipients also improve solvent capacity and the dispersibility of the formulation. Examples of polar oils include sorbitan trioleate (SPAN® 85) and oleic acid.

Co-solvents, e.g., ethanol, glycerol, propylene glycol, polyethylene glycols (PEG)-400, etc. increase the solvent capacity of the formulation for actives and aid the dispersion of systems that contain a high proportion of water soluble surfactants. Practical limits related to co-solvents include precipitation of the solubilized active from the solvent due to loss of the solvent capacity following dilution, immiscibility of some co-solvents with oils, and incompatibilities of low molecular weight solvents with capsule shells.

Water insoluble surfactants are lipid excipients with intermediate hydrophilic-lipophilic balance (HLB 8-12) that adsorb at oil-water interfaces. Depending on the degree of ethoxylation, they have a finite solubility in water. They can form emulsions if subjected to shear and may be referred as being 'dispersible' in water. They can form micelles but cannot self-emulsify due to their insufficiently hydrophilic nature. Oleate esters such as polyoxyethylene (20) sorbitan trioleate (TWEEN®-85) and polyoxyethylene (20) glyceryl trioleate (TAGOT®-TO) exemplify water-insoluble surfactants with HLB 11-11.5. However, a blend of TWEEN®-80 and SPAN®-80 with average HLB of 11 is not similar to TWEEN®-85 in function. A blend of TWEEN®-80 and SPAN®-80 has both water-soluble and water-insoluble molecules, but TWEEN®-85 has predominantly water-insoluble molecules.

Water-soluble surfactants are the most common surfactants for formulating self-emulsifying drug delivery systems. Materials with HLB≥12 can form micellar solutions at low concentrations by dissolving in pure water above their critical micellar concentration (CMC). Water-soluble surfactants are synthesized by PEG with hydrolyzed vegetable oils, or alternatively alcohols can be made to react with ethyleneoxide to produce alkyl ether ethoxylate, a commonly used surfactant (e.g., cetostearyl alcohol ethoxylate 'CETOMACROGOL™'). A reaction of sorbitan esters with ethylene oxide produces polysorbates, predominantly ether ethoxylates. CREMOPHOR® RH40 and RH60 (ethoxylated hydrogenated castor oil) are examples of this type, obtained from hydrogenation of materials derived from vegetable oils. CREMOPHOR® EL (ethoxylated castor oil), which is not hydrogenated, is also widely used. CREMOPHOR® enhances absorption by inhibiting the efflux pumps; while the inhibition mechanism is not determined it may be a non-specific conformational change due to penetration of the surfactant molecules into the membrane, adsorption on to the surface of the efflux pumps, or interaction of molecules with intracellular domains of efflux pump.

Additives may be added to protect the formulation from oxidation. Examples include lipid soluble anti-oxidants such as $\alpha$-tocopherol, $\beta$-carotene, propyl gallate, butylated hydroxyl toluene (BHT), butylated hydroxyanisole (BHA), etc.

Lipid behavior during formulation is assessed because lipid excipients have different chemical compositions that lead to broad melting ranges. Thermal properties of lipids, e.g., crystallization temperature, melting point, glass transition temperature, and determination of solid fat content of the excipient versus temperature, are evaluated using differential scanning calorimetry (DSC). Lipid organization during heating or cooling is assessed by hot-stage microscopy. Crystallinity of a lipid excipient is confirmed by X-ray diffraction (XRD).

High performance liquid chromatography (HPLC) and gas chromatography (GC) can determine the exact composition of ethers, esters, and fatty acid distribution. Other chemical indices include the molecular weight of fatty acids determined from their saponification value, saturation of hydrocarbon chains determined by an iodine-based assay, oxidative changes determined by measuring peroxides, free fatty acids measured from acid content, and free hydroxyl groups determined by measuring hydroxyl group content.

The FDA-required dissolution testing does not correlate to the in vivo behavior of lipid-based formulations. Lipids in the gastrointestinal tract are subjected to digestion processes in the presence of lipases (gastric and pancreatic) that also affect the emulsification and dispersion properties of the lipid excipients, leading to altered solubilization capacity in vivo. Hence, the digestibility of the lipid excipients must be considered when selecting lipid-based formulations. Dissolution testing in biorelevant media can assess such effects and predict in vivo behavior. The effectiveness of self-emulsifying formulations can be determined by dispersion testing (emulsification capacity and particle size). Photon correlation spectroscopy (PCS) or laser light diffraction can be used to measure the particle size, and visual observation can help predict emulsification capacity.

Lipid-based excipients enhance the oral absorption of drugs by affecting various physiological processes, e.g., stimulating bile flow and pancreatic juice secretion, prolonging gastric emptying, increasing the membrane fluidity, opening of tight junctions, promoting lymphatic transport of drugs thus avoiding first pass metabolism, and inhibiting efflux transporters. To assess these effects various in vitro models are available, including intestinal microsomes, Caco-2 cells, everted gut sac using chamber and in situ perfusion assays.

Liposomes may be used; these spherical bilayer structures resemble the cell membrane in their arrangement and are mainly amphiphilic phospholipids (hydrophilic head and hydrophobic fatty acid tail). When hydrated, these phospholipids form spherical bilayer structures, oriented with their hydrophobic tails oriented toward the structure interior and hydrophilic heads oriented toward the structure exterior. Hydrophilic substances can be embedded in the aqueous internal spaces of the globules, while hydrophobic active can be embedded within the inner fatty acid layers.

Solid lipid nanoparticles (SLN) may be used. SLN can enhance bioavailability along with controlled and site-specific drug delivery, so are potential carriers for oral intestinal lymphatic delivery. SLNs are typically spherical particles ranging from 10 nm to 1000 nm with a solid lipid core matrix (stabilized by surfactants) that can solubilize lipophilic molecules. Lipids mainly used include monoglycerides such as glycerol monostearate, diglycerides such as glycerol behenate, triglycerides such as tristearin, fatty acids such as stearic acid, steroids such as cholesterol, and waxes such as cetyl palmitate. Oral bioavailability of one drug was improved by formulating a N-carboxymethyl chitosan polymer that coated the drug loaded SLN using a monoglyceride lipid and soya lecithin and poloxamer 188 surfactants (Venishetty et al.)

In spray congealing, also termed spray cooling, molten lipid is sprayed into a cooling chamber and, on air contact, congeals into spherical solid particles. The solid particles are collected from the bottom of the chamber and filled into hard gelatin capsules or compressed into tablets. Ultrasonic atomizers generate solid particles in the spray cooling process. Parameters to be considered are the melting point of the excipient, the viscosity of the formulation, and the cooling air temperature inside the chamber to allow instant solidification of the droplets. Drug granules have been reported to be prepared by melt granulation using PEG 4000 or Poloxamer 188 as a meltable binder and lactose monohydrate as filler. Microparticles with narrow size distribution were reported when stearoyl polyoxylglycerides (GELUCIRE® 50/13) were used as an excipient and significantly enhanced solubility of poorly water soluble drugs (Cavallari et al.).

Melt granulation, also referred to as pelletization, transforms a powder mix of active into granules or pellets. A meltable binder (molten state) is sprayed onto the powder mix in presence of high-shear mixing ('pump on' technique), or the meltable binder is blended with powder mix and melts due to the friction of particles (solid/semisolid) during high-shear mixing. The melted binder forms liquid bridges between powder particles and forms small granules that transform into spheronized pellets under controlled conditions. Depending on powder fineness, 15%-25% of the lipid-based binder can be used. Parameters to be considered during the process are binder particle size, mixing time, impeller speed, and viscosity of the binder on melting. The dissolution rate of a drug was improved by formulating melt agglomerates containing solid dispersions of drug (Seo et al.). Lactose monohydrate was melt-agglomerated with a meltable binder, e.g., PEG 3000 of GELUCIRE® 50/13 in a high shear mixer.

Polyoxylglycerides, partial glycerides or polysorbates, and lecithins are exemplary lipid excipients used in the melt granulation technique to form self-micro-emulsifying systems.

In embodiments, sustained release matrix tablets may be formulated using hydrophobic carriers or meltable binders such as stearic acid, carnauba wax, and bees wax, by melt granulation techniques, rendering the carriers hydrophobic for sustained delivery.

In one embodiment, a pulsatile release form is used. The pulsatile release form includes an active core having one or more coatings, referred to as a "coated core" formulation.

The coated core may also be used in combination with an amount of the active suitable for immediate release.

In one embodiment, an amount of active formulated for immediate release in combination with at least a second amount of active formulated so the second amount has a delay before onset and release of the second portion is or can be extended over time, referred to as a "delayed extended release" formulation. Each of these pulsatile release dosage formulations is further described, with all percentages by weight unless indicated otherwise.

The "coated core" formulation is an active core of the dosage that includes an inert particle such as a commercially available nonpareil sugar sphere. The amount of active in the core is varied depending on the desired dose to be delivered. In one embodiment, the core contains about 5% active to about 90% active. In one embodiment, the core contains about 5% active to about 60% active. The amount of active is based on the total weight of the core. Those skilled in the art will be able to select an appropriate amount of active for coating or incorporation into the core to achieve the desired dosage form. Typically, the coated core can include about 80 mg, 160 mg, up to about 480 mg active. An aqueous or a pharmaceutically acceptable solvent medium may be used for coating the core particles. Any type of pharmaceutically acceptable inert binder may be used to bind the active to the inert particle. Water soluble binders may be used. Alcohol soluble binders may be used. Binders such as polyvinylpyrrolidone (PVP), carboxyalkylcelluloses, polyethylene oxide, polysaccharides such as dextran, corn starch, hydroxypropyl methylcellulose (HPMC (former) or hypromellose (current)), hydroxypropylcellulose, etc. may be used by dispersing them in water at a concentration from about 0.5 weight % to 5 weight %. The active can be in this coating formulation in solution form or suspension form. The concentration of active may vary from about 0.1 weight % to about 20 weight %, depending on the viscosity of the coating formulation.

In one embodiment, the active core is prepared by granulation or by extrusion and spheronization. The active, a binder such as PVP, an optional dissolution rate controlling polymer such as high viscosity HPMC (hypromellose), and optionally other pharmaceutically acceptable excipients are blended in a high shear granulator (e.g., FIELDER® granulator), or a fluid bed granulator (e.g., GLATT® GPCG granulator), granulated to form agglomerates by adding/spraying a granulating fluid, such as water or alcohol, and dried. The wet mass is extruded and spheronized to produce spherical particles (beads) using an extruder. In these embodiments, the drug load may be 90% by weight based on the total weight of the extruded or granulated core.

In one embodiment, one layer of membrane coating on the particle containing the active includes a plasticized enteric polymer, and the other layer includes a mixture of a water insoluble polymer and a plasticized water dispersible/enteric polymer. The water insoluble polymer and the water dispersible polymer are present at a weight ratio of about 10:1 to 1:1, or about 4:1 to 1:1. The total weight of the coatings is about 15 weight % to 80 weight %, or about 20 weight % to about 60 weight % based on the total weight of the multiparticulate dosage form.

An intermediate acid-containing membrane is optional. If included, the intermediate acid-containing membrane may include an organic acid, e.g., fumaric acid, citric acid, succinic acid, tartaric acid, malic acid, maleic acid, etc.; and a binder, e.g., PVP. Water soluble polymers or alcohol soluble polymers are usually used. The weight of this acid-containing membrane is about 5% to about 20% based on the total weight of the coated beads. The acid in the acid-containing membrane delays dissolution of the enteric polymer in the inner layer, thereby increasing the lag time as well as decreasing the rate of release of the active from the coated bead. The composition of the outer layer of the polymeric membrane, and the individual weights of the inner, intermediate, and outer membrane layers, are further optimized to achieve pulsatile release profiles for the active based on predicted in vitro/in vivo correlations. Thus, the pulsatile release dosage formulation is optimized to release an amount of active after a predetermined time period and/or at a particular point in the digestive tract of the individual administered the formulation.

Examples of enteric polymers include, but are not limited to, the following compounds or composition, either alone or in combination: esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers, and shellac. These polymers may be used as a dry powder or an aqueous dispersion. Methacrylic acid copolymers EUDRAGIT® L100, S100, L30D are available (Rohm Pharma), cellulose acetate phthalate CELLACEFATE® (Eastman Chemical Co.), cellulose acetate phthalate aqueous dispersion AQUATERIC® (FMC Corp.), and hydroxypropyl methylcellulose acetate succinate aqueous dispersion AQOAT® (Shin Etsu K.K.).

Examples of water insoluble polymers include, but are not limited to, the following compounds or composition, either alone or in combination: cellulose derivatives (e.g. ethylcellulose), polyvinyl acetate (KOLLICOAT® SR 30D, BASF), neutral copolymers based on ethyl acrylate and methylmethacrylate, copolymers of acrylic and methacrylic acid esters with quaternary ammonium groups such as EUDRAGIT® NE, RS or RS30D, RL or RL30D, etc.

Membrane coatings can be applied to the core using any pharmaceutical coating method known in the art. For example, fluid bed coating may be used.

A pulsatile release dosage formulation may be prepared by (i) coating an inert particle, e.g., a non-pareil seed (sugar sphere), with the active and polymeric binder, or by preparing the particle containing the active by granulation and/or extrusion/spheronization to form an active particle; (ii) coating the active particle with a plasticized enteric coating, forming the plasticized enteric coated active particle; and (iii) coating the plasticized enteric coated active particle with a mixture of a water insoluble polymer and an enteric polymer. The release characteristics can be modulated by interchanging parts (ii) and (iii). An organic acid, as previously described, can be added to the membrane between parts (ii) and (iii) to further modulate the lag time and active release profile from the particle.

In one embodiment, the formulation may use a single form of the particulate to provide a time-controlled pulsatile release of the active several hours after oral administration, or to target to specific absorption sites. In one embodiment, dosage forms incorporating the multicoated active containing particles are combined in a composite dosage formulation with an amount of active for immediate release, e.g., in a gelatin, either hard gelatin or soft gelatin, capsule. This embodiment provides a composite dosage form having both an immediate release portion and time-controlled pulsatile release portion of active.

The optional immediate release portion and the active of the coated core can each include about 10 mg, 20 mg, etc.

of active, a coated core dosage form of the present invention can contain about 10 to 80 mg of active.

In one embodiment, a delayed extended release form is used.

In one embodiment, a dosage form can provide at least a bi-modal blood profile of active, e.g., the profile shown in FIG. 2. In this embodiment, the dosage form contains at least a first amount of active for immediate release, and a second amount of active for delayed extended release. For example, a first portion of active is immediately released during the first hour after administration from the inventive dosage form. There is an elapsed time period where substantially no active is released and/or is capable of entering the circulation, and/or is bioavailable from a second portion of administered active. Then, after another elapsed time, e.g., a few hours, additional active is released, and the release of this second portion occurs over an extended period of time, e.g., up to 12 hours after initial administration or even longer. This release of the second portion typically occurs after a lag time during which no active is released, so such dosage forms that can exhibit a delay before the initiation of release of an amount of active are termed "delayed extended release" dosage forms. Such a dosage form can be administered alone, or it can be administered in combination with other dosage forms.

It is desirable for the blood level of active to increase, with the blood concentration corresponding to the amount of active that is bioavailable after the immediate release in the first hour after administration. After a time, blood levels of active decreases to less than desirable or therapeutic levels. The second portion of active can enter the circulation after the immediate release portion of active has been released. In embodiments, after blood levels of active begin to decrease, the formulation desirably increases and/or maintains blood levels at or above about the desired concentration without the need to administer a second dose of active.

The following example illustrates one embodiment. The first immediate-release portion of active has an initial pharmacokinetic profile. Fillers, excipients, etc. can account for the final weight percent.

Formulations for delayed sustained or extended release are as follows. Each sustained release composition includes an amount of active formulated to release the active over a period of 4 hours to 12 hours, typically 6 to 12 hours.

Polyalcohols such as mannitol, coagulants such as a POLYOX®, coagulants and lubricants such as stearic acid are added to yield a granulation that can provide a delayed and extended release active formulation. Caplets, tablets, or other dosage forms of the delayed release formulation are prepared using procedures known in the art, including encapsulating procedures. Such dosage forms, without more, typically exhibit "sustained release" blood profiles, i.e., the dosage forms typically immediately releases active after ingestion and continues to release active over time. These compositions can also be formulated into a dosage form, and can exhibit extended release profiles, releasing active for a period of a few hours up to 12 hours after ingestion.

In one embodiment, the dosage forms formed from the compositions can be optionally base coated to seal the tablets for subsequent processing. Sealers include, e.g., HPMC, (poly)ethylene glycol (PEG), etc.

Figure 17:
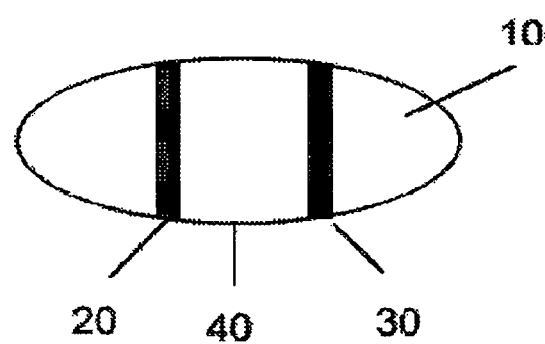
FIG. 17 shows a tablet with intermediate layers separated by bands.
Figure 18:
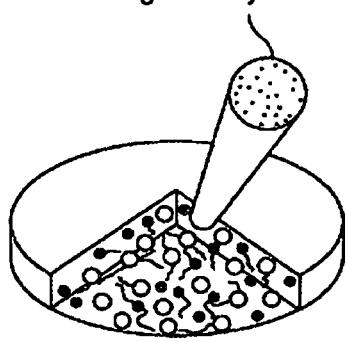
FIG. 18 shows an orally disintegrating tablet containing coated, delayed/ER drug particles, beads or granules; the inset shows a drug in a polymer matrix.
Figure 19:
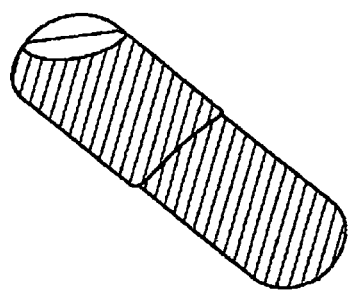
FIG. 19 shows a capsule containing drug solution and coated, delayed/ER drug particles, beads or granules.
Figure 20:
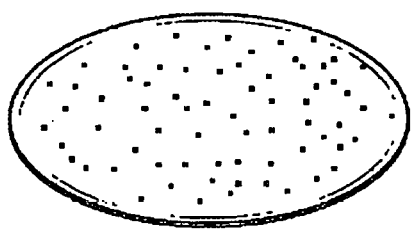
FIG. 20 shows a softgel containing drug solution and coated, delayed/ER drug particles, beads or granules.

In one embodiment, a dosage form is banded with one or more bands of one or more polymeric materials, as subsequently described and shown in FIG. 17. One or more circumferential or other types of bands of polymeric material are used, e.g., a relatively insoluble polymeric material that does only minimally or does not erode or degrade during the dispensing period. Typical insoluble polymers include the water insoluble polymers previously described. The number of bands, the position or spacing between bands, and the thickness of the bands can control the rate of release of active. For example, a space of 0.5 mm, 1.0 mm, 1.5 mm, 2.0 mm, 2.5 mm, or 3.0 mm can be present between bands if multiple bands are used. For example, each band can be 0.5 mm, 1.0 mm, 1.5 mm, or 2.0 mm wide and have a thickness of about 0.1 micron to 100 micron, or 0.1 micron to 50 micron, or 0.1 micron to 20 micron. As shown in FIG. 17, in one embodiment, a caplet has two circumferential polymeric bands, each band 20 and 30 has a width of about 1 mm and a spacing 40 of about 2 mm. The banded formulation slows the release of the active and extends the period of time over which the active can be released and/or enter the circulation, i.e., to be rendered bioavailable. In embodiments, the band(s) delays the onset of release of active such that there is a lag time, also termed a delay of onset or delayed release during which no active is released. A delay of onset can be from 0 hour to 4 hours, or may be 0 hour to 3 hours, or may be 0.5 hour to 4 hours, or may be 1 hour to 2 hours after administration.

The enteric coating may also include other excipients or fillers, e.g., talc, lactose, dicalcium phosphate, lubricants such as magnesium stearate, etc.

The banded dosage form can be coated with an enteric coating at a level of about 2 $\mu g/cm^2$ to 10 $\mu g/cm^2$, typically about 7 $\mu g/cm^2$. The enteric coating delays the onset of active such that there is time during which no active is released after administration of the dosage form. Typically, after enteric coating, delay of onset of active from a coated banded dosage form (e.g., an enteric coated banded caplet) can be from 0.5 hour to 4 hours, typically 1 hour to 2 hours.

In one embodiment, an immediate release dose of active previously described is combined with an enterically coated banded caplet using methods known in the art to produce a single composite dosage form, e.g., into a single gelatin capsule. The formulation may be tailored to provide a specific desired blood profile.

In embodiments, the compositions include at least an immediate release formulation and a sustained release formulation, subsequently described below. Sustained release formulations do not typically exhibit a delayed onset of active. Sustained release formulation do not typically exhibit a significant time period during which no drug is made bioavailable from the dosage form after administration.

In one embodiment, a tablet capsule is a capsule containing a first portion of active in a tablet form that is formulated for immediate release upon ingestion or administration, and at least a second portion of active that is in a tablet form that is formulated for sustained release, i.e., the second portion continues to release an amount of active up to 6-12 hours after ingestion. At least 15%-50% of the active is an immediate release formulation and is in a tablet form and is suitable for immediate release. The remainder of the tablet capsule, by weight, can include a sustained release formulation of active or a portion of the sustained release formulation of active. The tablet containing an immediate release formulation of active and the tablet containing a sustained release formulation of active may be combined in a single dosage form, e.g. a gelatin capsule, using methods known in the art.

In one embodiment, a granulation caplet is capsule or caplet containing a first portion of a granulation of active that is formulated for immediate release, and at least a second portion of active that is in tablet form that is formulated for sustained release. At least 15%-50% of active is an immediate release formulation and can be in granules versus a tablet. In one embodiment, at least about 80% of the granulation capsule includes a composition of active for immediate release in a granular form, typically contained in a separate caplet. The remainder of the granulation caplet, by weight, may include a sustained release formulation of active, or the granulation caplet may include a portion of the sustained release formulation of active. The caplet containing an immediate release formulation of active and the caplet containing a sustained release formulation of active may be combined in a single dosage form, e.g. a gelatin capsule, using methods known in the art.

In one embodiment, a layered tablet contains a tablet having two or more layers with the active that is formulated for immediate release, and a layer of active that is formulated for sustained release. The layered tablet contains an amount of active for immediate release upon ingestion, and at least a second portion of active that can immediately provide an amount of active for up to 6 hours-12 hours after layered tablet ingestion. At least 15%-50% of active is an immediate release formulation. In one embodiment, at least about 80% of the layered tablet includes a composition of active for immediate release. The remainder of the layered tablet, by weight, may include a sustained release formulation of active, or may include a portion of the sustained release formulation of active. The formulations can be combined in a conventional manner, e.g. in a tablet press, so that after processing, the final tableted dosage form has two or more layers, at least a first layer containing the immediate release formulation of active and a second layer containing the sustained release formulation of active.

In one embodiment, the active is least 20% to 30%, 30% to 60%, or 70% by weight of the sustained release composition, with the remaining weight of the composition excipients, e.g., fillers, lubricants, polymers, etc. The polymer can be present from 5% to 20% by weight of the sustained release composition in one embodiment, and from 7% to 10% by weight of the sustained release composition in one embodiment, and from 10% to 16.5% by weight of the sustained release composition in one embodiment. In one embodiment, the polymer is a cellulosic polymer, e.g. Methocel K4M and is present at about 10% by weight. The sustained release formulation can be prepared by direct compression or wet granulation.

The formulation may be compressed into tablets, or may be incorporated directly with food. Such compositions should contain at least 0.1% of active compound. The percentage of the compositions and preparations may vary, e.g., about 2% to about 60% of the weight of the unit.

Excipients include, but are not limited to, one or more of a pharmaceutically acceptable inert diluent; an assimilable edible carrier; a disintegrant to facilitate disintegration, e.g., modified cellulose derivatives, modified starch derivatives, etc., noting that one skilled in the art appreciates that other ingredients including binders and lubricants can also affect the dissolution profile of the dosage form; a hard or soft shell gelatin capsule; dicalcium phosphate; a binder such as gum tragacanth, acacia, corn starch, or gelatin; a disintegrating agent such as corn starch, potato starch, alginic acid, etc.; a lubricant such as magnesium stearate; a sweetening agent such as sucrose, lactose, or saccharin; a flavoring agent such as peppermint, oil of wintergreen, cherry flavoring; one or more surfactants such as ionic, non-ionic, and/or bile salt surfactants, with anionic surfactants including sodium alkyl sulfate (sodium lauryl sulfate) and sulfosuccinate derivatives such as docusate sodium, non-ionic surfactants including polyoxyethylene sorbitan fatty acid esters (polysorbates) such as TWEEN® 20, TWEEN® 80, TWEEN® 40, SPAN® 20, fatty acid esters of polyethylene glycols such as GELUCIRE® 44/14, GELUCIRE® 50/13, saturated polyglycolized (including mono, di or tri)glycerides, medium chain monoglycerides (6-10 carbons) such as glyceryl monocaprylate (IMWITOR® 308), glyceryl monocaproate (CAPMUL® MCM C-8), glyceryl caprylate/caprate (CAPMUL® MCM), polyoxyethylene glyceryl caprylate, and polyoxyethylene glyceryl caproate (LABRASOL®), medium chain fatty acid esters such as glyceryl tri caprate and glyceryltricarilate (MIGLYOL® 612), block polymers of ethylene oxide and propylene oxide, polyoxyethylene-polyoxyl propylene block copolymers such as Poloxamer 188 (PLURONIC® F-68), Poloxamer 237 (PLURONIC® F-87), Poloxamer 338 (PLURONIC® F-108), Poloxamer 407 (PLURONIC® F-127), Poloxamer 124 (PLURONIC® L-44), polyoxyl stearate-polyethoxylated (40) stearic acid (MYRJ® 52), ethoxylated castor oil-polyethoxylated (60) hydrogenated castor oil (CREMOPHOR® EL), ethoxylated hydrostearic acid polyethylene glycol 660 hydroxystearate (SOLUTOL® HS 15), polyoxyethylene alkyl ethers (12-18 carbons) such as polyoxyl 20 cetostearyl ether (ATLAS® G-3713), polyoxyl 10 oleyl ether (BRIJ® 96, BRIJ® 97, Oleth 10), polyethylene glycol ether (TRITON™ X-100, TRITON' X-114, TRITON™ X-405, TRITON' N-101) and lecithins such as phospholipids (dimyristoyl DL-alpha-phophatidylcholine), bile salt surfactants including deoxycholic acid, sodium deoxycholate, cholic acid, sodium taurocholate; etc. A capsule dosage form may also contain a liquid carrier. Other materials may be present as coatings or to otherwise modify the physical form of the dosage form, e.g., tablets, pills, or capsules may be coated with shellac and/or sugar. A syrup or elixir may contain the active, sucrose as a sweetening agent, methyl and propylparabens as preservatives, a dye, and a flavoring agent.

In embodiments, other actives may be included in the formulation.

In one embodiment the dosage forms are a liquid filled soft gel capsule containing excipients that have lipids, surfactants and solvents. The capsules may contain formulations for immediate release, delayed release, sustained release, or controlled release.

The formulation may contain excipients such as one or more fatty acids. The method involves dissolving, melting, or suspending a poorly water soluble active agent in one or more fatty acids, conjugated fatty acids, (semi-) solid surfactants having a high HLB value, and/or hydrophilic polymers. Suitable fatty acids include $C_{10}$-$C_{18}$ fatty acids, preferably $C_{16}$-$C_{18}$ fatty acids. Suitable conjugated fatty acids include $C_{10}$-$C_{18}$ fatty acids, preferably $C_{16}$-$C_{18}$ fatty acids, conjugated with glycerol (e.g., monoglycerides), monosaccharides, and/or polyethylene glycol (PEG). Suitable hydrophilic polymers include poloxomers and poloxamines.

Suitable fatty acids include $C_{10}$-$C_{18}$ fatty acids, more preferably $C_{16}$-$C_{18}$ fatty acids. Exemplary fatty acids include, but are not limited to, dodecanoic (lauric) acid, tetradecanoic (myristic) acid, hexadecanoic (palmitic) acid, heptadecanoic (margaric) acid, octadecanoic (stearic) acid, eicosanoic (arachidic) acid, docosanoic (behenic) acid, tetracosanoic (lignoceric) acid, hexacosanoic (cerotic) acid, heptacosanoic (carboceric) acid, octacosanoic (montanic) acid, triacontanoic (melissic) acid, dotriacontanoic (lacceroic) acid, tritriacontanoic (ceromelissic) acid, tetratriacontanoic (geddic) acid, and pentatriacontanoic (ceroplastic)

acid. The fatty acids can be saturated fatty acids, monounsaturated fatty acids, polyunsaturated fatty acid, or combinations thereof.

Oils, for example, vegetable oils, such as soybean oil can be used alone or in combination with the coating materials listed above. Soybean oil contains 14.4% saturated fatty acids, 23.3% monounsaturated fatty acids, such as oleic acid, and 57.9% polyunsaturated fatty acids, such as linoleic acid and alpha linoleic acid.

In one embodiment, the fatty acid is covalently coupled to glycerol, a monosaccharide, such as sorbitol or sorbitan, a polyalkylene oxide, such as polyethylene glycol and polypropylene glycol, or combinations thereof. These materials are referred to as conjugated fatty acids. Suitable conjugated fatty acids include, but are not limited to, polyethylene glycol esters of fatty acids, such as those available commercially under the tradename GELUCIRE®, sorbitan esters of fatty acids, such as sorbitan monostearate, glycerol fatty acid esters of the fatty acids listed above, such as glycerol behenate and glyceryl monostearate, and combinations thereof.

The concentration range of the fatty acid is from about 1% to about 20% by weight of the composition, preferably from about 5% to about 15% by weight of the composition (microparticles and carrier).

The water-insoluble active can be coated with one or more surfactants, alone or in combination with or more fatty acids or conjugated fatty acids and/or one or more hydrophilic polymers. In one embodiment, the surfactant has an HLB value greater than about 10, greater than about 12, greater than about 14, or greater than about 16 (on a scale of 1-18). Surfactants having the desired HLB are known in the art. The surfactant can be anionic, cationic, or non-ionic. In one embodiment, the surfactant is a non-ionic surfactant.

Examples of such surfactants include, but are not limited to, polysorbate 20, 40, and 80 (marketed under the name TWEEN®), polyoxyethylene monostearate, some sugar esters, such as sucrose monolaurate, ethoxylated nonyl phenols, alpha olefin sulfonates, ethoxylated tallow amines, ethylene oxide/propylene oxide block copolymers, ethoxylated soya amines, fatty acids and alcohols, polyethoxylated castor oil, polysorbates, polyoxyethylene alkyl ethers, and polyoxyethylene stearates.

In one embodiment, the surfactant is a high HLB surfactant containing a fatty acid chain. Suitable surfactants include, but are not limited to, polyethoxylated castor oil, polysorbates, polyoxyethylene alkyl ethers, and polyoxyethylene stearates.

Polyoxyethylene castor oil derivatives contain mainly ricinoleyl glycerol ethoxylated with 30-50 molecules of ethylene oxide. Polysorbates or polyoxyethylene sorbitan fatty acid esters are a series of partial fatty acids esters of sorbitol and its anhydrides copolymerized with approximately 20, 5, or 4 moles of ethylene oxide for each mole of sorbitol and its anhydrides. The resulting product is a mixture of molecules having a wide range of molecular weights. Polyoxyethylene alkyl ethers are a series of polyoxyethylene glycol ethers of linear fatty alcohols (n-alcohols), such as lauryl, myristyl, cetyl, and stearyl alcohol. Polyoxyethylene stearates are produced by polyethoxylation of stearic acid.

Without desiring to be bound by any theory, it is believed that the hydrophilic part of the surfactant enhances the compatibility of the active agent with the aqueous dissolution media in vitro or in vivo and that the fatty acid side chain enhances absorption via fatty acid oxidation. During fatty acid oxidation, intracellular $Ca^{2+}$ is consumed which results in the widening of gap junctions, allowing passage of the active agent between cells. Further, such coated particles may be more stable than drug alone, for example, by preventing oxidation of the active agent.

The concentration of the surfactant is from about 1% to about 50%, preferably from about 5% to about 15% by weight of the composition (microparticles and carrier).

Suitable hydrophilic polymers include, but are not limited to, poloxamers, poloxamines, polyethylene glycols, polyvinyl alcohols, polyvinylpyrrolidone, poly(vinyl alcohol), cellulosic materials, such as hydroxypropylcellulose, hydroxymethylcellulose, hydroxypropylmethyl-cellulose, gelatin, carboxymethyl cellulose, and polypeptides.

The concentration of the hydrophilic polymer is from about 1 to about 50% by weight of the composition, more preferably from about 5% to about 15% by weight of the composition. If the hydrophilic polymer is a polyethylene glycol, the concentration is from about 1% to about 80% by weight of the composition, from about 30% to about 60%, from about 35% to about 60%, or from about 40% to about 60% by weight of the composition (microparticles and carrier).

In one embodiment, the microparticles are formed by adding a mixture of the drug and coating material(s) to a pharmaceutically acceptable carrier. In one embodiment, the carrier is a hydrophilic or lipophilic carrier. The resulting particles are suspended in the carrier. The carrier may be a single component or a mixture of components. The carrier can include solvents, surfactants, or other excipients. The carrier materials can alter or modify the rate of release of the drug from the microparticles and/or the rate of dissolution of the drug. The compositions may exhibit a biphasic release profile due to the controlled release properties of the microparticles and the controlled release properties of the carrier. Varying the qualitative and quantitative composition of the carrier materials may allow one to modulate the release profile of the active agent. The carrier may contain one or more rate controlling excipients which regulate release of the active agent. Exemplary rate controlling excipients include, but are not limited to, glyceryl behenate, GELUCIRE®, CREMOPHOR®, hydrogenated vegetable oil, bees wax, cellulosic polymers such as hypromellose, alginates, CARBOPOL® and combinations thereof.

In one embodiment, the carrier is a hydrophilic carrier containing a surfactant having a HLB value greater than about 10, greater than about 12, greater than about 14, or greater than about 16, and/or is water soluble. Exemplary hydrophilic carriers include, but are not limited to, polyethylene glycols, polyoxyethylene 32 lauric glycerides (available from Abitech under the tradename ACCONON® M-44), polyoxyethylene 8 capryliclearic glycerides (available from Abitech under the tradename ACCONON® MC-8) and glycofurol. The hydrophilic vehicle can further contain one or more miscible solvents such as glycerin, ethanol, glycofurol, and caprylocaproyl macrogol-8 (available from Gattefosse S.A., Saint Priest, France under the tradename LABRASOL®).

In one embodiment, the hydrophilic carrier is water or an alcohol. In another embodiment, the carrier is a hydrophilic carrier mixture containing polyethylene glycol, and optionally one or more surfactants and/or water. In a particular embodiment, the hydrophilic carrier is a mixture of PEG 400 (e.g., 57% by weight of the composition), water (e.g., 8% by weight of the composition), and TWEEN® 20 (e.g., 10% by weight of the composition). The hydrophilic carrier can also contain CREMOPHOR® RH 40. The concentration of the hydrophilic carrier is generally from about 50% to about 85% by weight of the composition (microparticles and carrier), preferably from about 70 to about 80% by weight of the composition.

In another embodiment, the carrier is a lipophilic carrier. In a preferred embodiment, the lipophilic carrier has an HLB value of less than about 10 and/or is oil soluble. Exemplary lipophilic oily vehicles include, but are not limited to, vegetable oils, medium chain mono-, di-, and triglycerides, glyceryl stearates (available from Sasol under the tradename IMWITOR®), polyoxyethylated oleic glycerides (available from Gattefosse, SA., Saint Priest, France, under the tradename LABRAFIL®), mineral oil, mono- and diglyceride emulsifiers such as glyceryl monooleate, glyceryl monocaprate, glyceryl monocaprylate, propylene glycol monocaprylate, and propylene glycol monolaurate (available from Abitec Corp., Columbus, Ohio, under the tradename CAPMUL®), and dimethylpolysiloxanes such as simethicone.

The concentration of the lipophilic carrier is generally from about 10% to about 50% by weight of the composition (microparticles and carrier), preferably from about 5% to about 35% by weight of the composition.

The compositions described can contain one or more pharmaceutically acceptable excipients that are considered safe and effective and may be administered to an individual without causing undesirable biological side effects or unwanted interactions. Exemplary additives include, but are not limited to, solvents, suspending agents, dispersants, buffers, pH modifying agents, isotonicity modifying agents, preservatives, antimicrobial agents, and combinations thereof.

Suitable additives for inclusion in the compositions described herein include, but are not limited to, antioxidants (e.g., alpha tocopherols, such as vitamin E acetate, ascorbic acid, butylated hydroxyanisole, and butylated hydroxytoluene); polar solvents (e.g., water, propylene glycol, and glycerin); hydrophobic solvents (e.g., corn oil, castor oil, soybean oil, olive oil, fish oil, peanut oil, peppermint oil, safflower oil, sesame oil, medium chain triglycerides, caprylic triglycerides, capric triglycerides derived from coconut oil or palm seed oil); and viscosity increasing agents (e.g., gelatin, glycerin, carrageenan, colloidal silicon dioxide, hydrogenated vegetable oil; povidone, and propylene glycol alginate).

Figure 21:
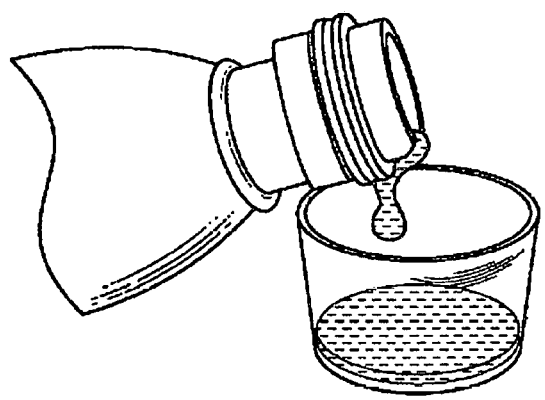
FIG. 21 shows a liquid vehicle containing coated, delayed/ER drug particles, beads or granules.

The microparticle compositions described herein are generally formulated for oral or parenteral administration. Suitable oral dosage forms include capsules, such as hard or soft, gelatin or non-gelatin capsules, or oral suspensions or syrups (e.g., FIG. 21). Suitable parenteral formulations include suspensions.

In one embodiment, the microparticle compositions (microparticles suspended in a hydrophilic or lipophilic carrier) are encapsulated in a capsule, such as a hard or soft capsule. The capsules can be prepared from natural and/or synthetic film forming polymers. Suitable natural film forming materials include, but are not limited to gelatin. Non-gelatin capsules include, but are not limited to, capsules made from carageenan, shellac, alginates, pectin, and zeins. Suitable synthetic film-forming polymers include, but are not limited to, methyl cellulose, hydroxypropyl methyl cellulose acetate succinate, hydroxypropyl methyl cellulose phthalate, cellulose acetate phthalate, and acrylates such as poly (meth) acrylate.

The compositions can also be encapsulated in an enteric capsule, wherein the capsule is coated with an enteric coating or the capsule shell contains an enteric polymer as described in WO 2004/030658 to Banner Pharmacaps, Inc.

Hard shell capsules are typically prepared by forming the two capsule halves, filling one of the halves with the fill solution, and then sealing the capsule halves together to form the finished capsule. Soft gelatin capsules are typically prepared using a rotary die encapsulation process. Such processes are known in the art.

The capsule shell can contain one or more additives. Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

Medium chain triglycerides may also be used. As used herein, "medium chain triglycerides" means $C_{6-12}$ ester chains formed via the esterification of glycerol with three fatty acids. There are various sources of medium chain triglycerides, for example coconut oil, palm kernel oils, etc. Fractionated coconut oils are the most commonly used sources for medium chain triglycerides. Examples of commercially available medium chain triglycerides may include MIGLYOL® 810, 812 or 881 produced by Sasol Germany GMBH, CAPTEX® 300, 355, or 810D produced by the Abitec Corporation, NEOBEE® M5 by the Stepan Company, CRODAMOL® GTC/C produced by Croda Inc, and LABRAFAC® Lipophile WL 1349 produced by the Gattesfosse Group. In one exemplary embodiment, the medium chain triglyceride may comprise CAPTEX® 355, which is a triglyc-eride of caprylic (C8)/capric (C10) acid.

Various amounts of the medium chain triglycerides may be included in the pharmaceutical formulation. In one or more embodiments, the pharmaceutical formulation may comprise about 50% to about 95% by weight medium chain triglycerides, or about 85% to about 95% by weight medium chain triglycerides. Moreover, in exemplary embodiments, the pharmaceutical formulation may include from about 100 mg to about 300 mg, or from about 200 mg to 300 mg of the weight medium chain triglycerides, or about 225 mg to 275 mg of the weight medium chain triglycerides, or about 250 mg of the weight medium chain triglycerides.

Similar to medium chain triglycerides, "medium chain monoglycerides" and "medium chain diglycerides" are $C_{6-12}$ ester chains formed via the esterification of glycerol with one fatty acid or two fatty acids, respectively. Examples of commercially available medium chain mono/diglycerides may include the CAPMUL® products produced by Abitec. It is also contemplated to use medium chain mono/diglyceride compounds that also include medium chain triglycerides, for example, the commercially available IMWITOR® compositions produced by Sasol.

In exemplary embodiments, the medium chain mono/diglycerides may comprise CAPMUL® MCM, which include medium chain mono/diglycerides of caprylic (C8)/capric (C10) acid. While all grades of the CAPMUL® MCM product line are suitable for use in the present invention, e.g., national formulary (NF) grade or CAPMUL® MCM EP, it may be desirable to use to EP grade as it includes 3% glycerol, whereas the NF grade includes 7% glycerol.

In accordance with one or more embodiment, the pharmaceutical formulation may comprise about 5% to about 25% by weight medium chain mono/diglycerides, or from about 5% to about 15% by weight medium chain mono/diglycerides. Moreover, in exemplary embodiments, the pharmaceutical formulation may include about 20 mg to about 50 mg of the weight medium chain mono/diglycerides, or about 25 mg to about 30 mg of the weight medium chain mono/diglycerides, or about 25 mg of the weight medium chain mono/diglycerides.

Without being bound by theory, the mixture of medium chain triglycerides and medium chain mono/diglycerides is important for the bioavailability of the active ingredient inside the liquid-filled bard gel capsule formulation. While a soft gel capsule may only include medium chain mono/diglycerides, a hard gelatin capsule with only medium chain mono/diglycerides may not provide the requisite physical stability of the finished dosage forms. However, a mixture of medium chain triglycerides and medium chain mono/diglycerides inside a hard gelatin capsule may achieve the desired product stability, solubility and bioavailability of the active pharmaceutical ingredient. Consequently, in accord with the invention, the ratio by weight of the medium chain triglycerides to the medium chain mono/diglycerides facilitates the solubility and stability of the active pharmaceutical ingredient (e.g., dutasteride) within the non-emulsified mixture prior to and after the addition of the mixture into the capsule. The medium chain triglycerides and medium chain mono/diglycerides may be present at a ratio by weight of from about 10:1 to about 5:1, or from about 10:1 to about 7:1.

In addition to the above components, other excipients known to one skilled in the art may be used, e.g., excipients used in the oral composition may be diluents, binders, lubricants, disintegrants, flavoring agents, coloring agents, stabilizers, glidants, plasticizers, preservatives and sweeteners.

Diluents may include liquid diluents such as any long chain triglyceride (arachis oil, almond oil, peanut oil, palm oil, palm kernel oil, blackcurrent seed oil, rice bran oil, soybean oil, canola oil, corn oil, coconut oil, cotton seed oil, castor oil, olive oil, Linn oils (Neem), sesame oil, primrose oil, vegetable oil, Lipex 108 (Abitec), wheat germ oil, fish oil, rapeseed oil, sunflower oil and saffola oil. In alternative embodiments, it is contemplated that other diluents may be used, for example, diluents selected from calcium-aluminum silicates (SIPERNAT® 106PQ), calcium carbonate, calcium phosphate dibasic, calcium phosphate tribasic, calcium sulfate, microcrystalline cellulose, microcrystalline silicified cellulose, powdered cellulose, dextrates, dextrose, fructose, lactitol, lactose anhydrous, lactose monohydrate, lactose dihydrate, lactose trihydrate, mannitol sorbitol, starch, pregelatinized starch, sucrose, talc, xylitol, maltose maltodextrin, maltitol, silicon dioxide, HPMC and combinations thereof.

The formulation includes the route of administration, type of preparation, non-active ingredients release of active, stability, scale-up, new processes for preparation of active, new processes for formulation.

In vivo performance evaluation includes pharmacokinetic data such as pK/pD such as $T_{max}$, $C_{max}$, plasma concentration curve, efficacy, side effects, etc.

Other release profiles include but are not limited to controlled, enteric, sustained, fast, multi-phasic, etc.

Other known and to be determined uses of the inventive formulations of domperidone and deuterated domperidone are encompassed by the invention.

Each of the references previously cited as well as listed below is incorporated by reference herein in its entirety:

Chang and Robinson, chapter 4: Sustained Drug Release from Tablets and Particles Through Coating, Pharmaceutical Dosage Forms: Tablets, vol. 3, Eds. Lieberman, Lachman, and Schwartz, Marcel Dekker, Inc., 1991

Campbell and Sackett, Chapter 3: Film coating, Pharmaceutical Unit Operations: Coating, edited by Avis, Shukla, and Chang, Interpharm Press, Inc., 1999.

Youssef et al., Identification of Domperidone Metabolites in Plasma and Urine of Gastroparesis Patients with LC-ESI-MS/MS, Xenobiotica 43 (2013) 1073-1083.

Michaud et al., An Improved HPLC Assay with Fluorescence Detection for the Determination of Domperidone and Three Major Metabolites for Application to in vitro Drug Metabolism Studies, J. Chromatogr. B, 852 (2007) 611-616.

The disclosed compositions include a therapeutic amount of domperidone or deuterated domperidone or a pharmaceutically acceptable salt thereof and at least one excipient. The excipient may, e.g., facilitate delivery of the active agent. As previously disclosed, other active agents may be included, e.g., analgesic agents, anesthetic agents, antioxidants, antimicrobial agents, antifungal agents, vitamins, etc.

One or more analgesic agents can be included in the pharmaceutical compositions to provide relief from pain that may result from gastroparesis. Examples of analgesics include, but are not limited to, simple analgesics such as paracetamol or aspirin; non-steroidal anti-inflammatory drugs (NSAIDS) such as ibuprofen, diclofenac sodium, or naproxen sodium; and/or opioids such as codeine, dihydrocodeine, codeine phosphate, fentanyl, methadone, tramadol hydrochloride, dextropropoxyphe hydrochloride, morphine, oxycodone, buprenorphine, or pethidine hydrochloride.

One or more anesthetic agents can be included in the pharmaceutical compositions to induce temporary and reversible absence of pain sensation caused by gastroparesis. Examples of anesthetics include, but are not limited to, one or more of lidocaine, benzocaine, bupivacaine, articaine, cocaine, etidocaine, flecamide, mepivacaine, pramoxine, prilocalne, procaine, chloroprocaine, oxyprocaine, proparacaine, ropivacaine, tetracaine, dyclonine, dibucaine, chloroxylenol, cinchocaine, dexivacaine, diamocaine, hexylcaine, levobupivacaine, propoxycaine, pyrrocaine, risocaine, rodocaine, and pharmaceutically acceptable derivatives thereof.

One or more antioxidants can be included in the pharmaceutical compositions. Examples of antioxidants include, but are not limited to, ascorbyl palmitate, butylated hydroxyanisole, butylated hydroxytoluene, diethylenetriaminepentaacetic acid (DTPA), edetates (EDTA), monothioglycerol, sodium ascorbate, sodium formaldehyde sulfoxylate, sodium metabisulfite, butylated hyrodxytoluene (BHT), butylated hydorxyanisole (BHA), sodium bisulfate, triglycolamate, vitamin E or a derivative thereof, and propyl gallate.

In one embodiment, domperidone or deuterated domperidone, and optionally any other agent, is incorporated into or on particles, including nanoparticles. Domperidone or deuterated domperidone particles may be suspended or dispersed in an aqueous medium. The particle size thus may range from microparticles (μm) to nanoparticles (nm).

A human or other mammal afflicted with gastroparesis, or other gastrointestinal motility disorders, can be treated through periodic administration of the inventive disclosed pharmaceutical compositions one or more times daily. The pharmaceutical agents, including domperidone or deuterated domperidone and any supplemental therapeutic agent, is present in the composition in an amount constituting a therapeutically effective dose. A therapeutically effective dose is an amount of the pharmaceutical agent that, upon treatment, results in a degree of reduction of symptoms relative to the pre-dose status of such symptoms.

The pharmaceutical compositions can be administered one to four times per day.

In one embodiment, domperidone or deuterated domperidone is administered in the range between about 0.1 mg to about 120 mg, or the range between 0.01% to 12.0% w/w, or in the range between about 0.0014 mg/kg to about 1.71 mg/kg. In other embodiments, domperidone or deuterated domperidone is administered in the range between about 0.5 mg to about 100 mg, or in the range between about 0.05% to about 10.0%, or in the range between about 0.007 mg/kg to about 1.43 mg/kg. In one embodiment, domperidone or deuterated domperidone is administered in the range between about 1 mg to about 60 mg, or between about 0.1% to about 6.0%, or between about 0.014 mg/kg to about 0.86 mg/kg. In one embodiment, domperidone or deuterated domperidone is administered in the range between about 2.0 mg to about 30 mg, or between about 0.2% to about 3.0%, or between about 0.028 mg/kg to about 0.43 mg/kg. In one embodiment, domperidone or deuterated domperidone is administered in the range between about 0.5 mg to about 120 mg, or between about 0.05% to about 12.0%, or between about 0.007 mg/kg to about 1.71 mg/kg. In one embodiment, domperidone or deuterated domperidone is administered in the range between about 2.0 mg to about 40 mg, or between about 0.2% to about 4.0%, or between about 0.028 mg/kg to about 0.57 mg/kg. All % designations are w/w.

The formulations can also include excipients. Exemplary excipients include, but are not limited to, binders, fillers, solvents, lubricants, antioxidants, buffering agents, salts, surfactants, vitamins, pigments, flavorants, disintegrating agents, and/or plasticizers.

Solid excipients can be added to the pharmaceutical composition and then ground and formed into tablets. Exemplary solid excipients include, but are not limited to, sugars, including lactose, sucrose, sucralose, mannitol, or sorbitol; cellulose-based materials, such as corn starch, wheat starch, rice starch, potato starch, gum tragacanth, gelatin, methyl cellulose, polyvinylpyrrolidone, hydroxypropylmethyl-cellulose, and/or sodium carboxymethyl cellulose. Excipients to facilitate tablet disintegration upon ingestion include, but are not limited to, agar, alginic acid and/or salts thereof, mannitol, microcrystalline cellulose, maize starch, citrus pulp, sodium lauryl sulfate, bentonite, sodium starch glycolate, calcium carboxymethyl-cellulose, clays, aligns, gums, wood cellulose, powdered natural sponge, and/or cation-exchange resins.

The composition can include other excipients and additives to modify one or more composition characteristics, such as coating ability, viscosity, palatability, etc. Excipients to improve palatability may include, but are not limited to, sugars such as lactose, sucrose, sucralose, dextrose, mannitol, or sorbitol; natural sweeteners such as honey; cellulose based additives such as corn starch, wheat starch, rice starch; other sweeteners such as alitame, aspartame, cyclamic acid and salts thereof, dihydrochalcones, glycyrrhizinates, monellin, sodium saccharine, thaumatin, or acesulfame potassium; and/or other sweeteners or flavorants.

Optional viscosity modifier excipients can be added to a liquid formulation of the composition to alter the composition's flow characteristics. Flow characteristics can be modified for incorporation into a specific device or application mechanism to apply the composition to a treatment site. Exemplary viscosity modifying excipients include, but are not limited to, glycerine, a carbomer homopolymer, a carbomer copolymer, acacia (gum arabic), agar, aluminum magnesium silicate, sodium alginate, sodium stearate, bladderwrack, bentonite, carbomer, carrageenan, ceratonia, chondrus, dextrose, furcellaran, gelatin, Ghatti gum, guar gum, sterculia gum, gum tragacanth, xanthum gum, hectorite, lactose, maltodextrin, mannitol, sucrose, sorbitol, honey, maize starch, wheat starch, rice starch, potato starch, polyethylene glycols, cellulose, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, propylene carbonate, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl-cellulose, carboxymethyl-cellulose (CMC) (including salts thereof), silicon dioxide, polyvinylpyrrolidone (PVP), and/or SPLENDA®.

The pharmaceutical compositions can also include one or more binders, fillers, solvents, lubricants, antioxidants, buffering agents, salts, surfactants, vitamins, pigments, flavorants, disintegrating agents, and/or plasticizers. Exemplary binders include, but are not limited to, any of the previously disclosed starches such as maize starch, wheat starch, rice starch, and/or potato starch, cellulosic derivatives such as methylcellulose, carboxymethyl cellulose, hydroxyethyl cellulose, hydroxy-ethylmethyl cellulose, etc., POLYOX™ polyethylene oxide polymers of any molecular weight or grade, irradiated or not, polyvinylpyrrolidone (PVP), AVICEL® microcrystalline cellulose powder, etc. Exemplary fillers include, but are not limited to, any of the previously disclosed sugars and starches, cellulose, calcium salts, diatomaceous earth, and/or titanium dioxide. Exemplary buffers include, but are not limited to, acetate buffers, citrate buffers, and/or phosphate buffers.

Surfactants added to the pharmaceutical composition can be anionic, cationic, non-ionic, or zwitterionic. Exemplary surfactants include, but are not limited to, sodium alkyl sulfates (e.g. sodium dodecyl sulfate (SDS)), quaternary ammonium and pyridinium cationic surfactants, polysorbates, sorbitan esters, bile acids, bile acid salts, nonoxynol or polyoxytheylene glycol fatty acid esters, and/or poloxamers. Exemplary lubricants include, but are not limited to, talc, hydrogenated fatty oils, magnesium stearate, calcium stearate, and/or stearic acid. Flavorants can include natural or synthetic flavors. Plasticizers include, but are not limited to, glycerol and sorbitol.

Pharmaceutical compositions for treating gastroparesis and other gastrointestinal motility disorders with domperidone or deuterated domperidone can be formulated for topical oral administration to mucosal surfaces. Mucoadhesive delivery technologies provide safe and efficacious delivery of domperidone or deuterated domperidone through the oral mucosa. These mucoadhesive delivery technologies include all methods of diffusion in the oral mucosa: (i) passive diffusion including trans-cellular (through cells) and para-cellular (where material passes through lipid rich domains around the cells), (ii) carrier mediated transport, and (iii) endocytosis/exocytosis where material is actively taken up and excreted by cells via the endocytic pathway. Bioadhesion, also known as mucoadhesion, defines the ability of a biological or synthetic material to adhere or "stick" to a mucous membrane, resulting in adhesion of the material to the tissue for a protracted time. This ability provides application in drug delivery and enhanced drug bioavailability that results from the lengthened time in which the bioadhesive dosage form is in contact with the absorbing tissues, versus a standard dosage form. For a material to be bioadhesive, it must interact with mucus. Mucus is a highly hydrated, viscous anionic hydrogel layer protecting the mucosa. Mucin is composed of flexible glycoprotein chains.

In this embodiment, the pharmaceutical composition includes a therapeutic amount of domperidone or deuterated domperidone and any optional other active agent if present, and at least one excipient that can include a mucoadhesive or bioadhesive to increase the duration of contact between the pharmaceutically active agent and the oral mucosa, and to increase mucosal absorption of the active agent. The absorption surface is the tissue surface underneath the oral mucosa to which the pharmaceutically active agent is intended to be applied. The pharmaceutical compositions can be applied in the form of ointments, creams, lotions, gels, powders or pastes, and can be applied to treatment sites with or without occlusion by films or tapes or by specific adhesive bandages. The compositions can also include a vehicle to facilitate administration of the composition to the oral mucosa.

Exemplary mucoadhesive or bioadhesive excipients include, but are not limited to, polymers that are natural, synthetic or biological; lipids, phospholipids, etc. Examples of natural and/or synthetic polymers include cellulosic derivatives such as methylcellulose, carboxymethyl cellulose, hydroxyethyl cellulose, hydroxyethylmethyl microcrystalline cellulose, etc.; natural gums such as guar gum, xanthan gum, locust bean gum, karaya gum, vee-gum, etc.; polyacrylates such as CARBOPOL® polymers, polycarbophil, etc.; alginates, thiol-containing polymers, polyoxyethylenes, polyethylene glycols (PEG) with molecular weights preferably between 1000 and 40,000 Da whether linear or branched, dextrans with molecular weights preferably between 1000 and 40,000 Da of any source, block copolymers e.g., combinations of lactic acid and glycolic acid such as PLA, PGA, PLGA of various viscosities, molecular weights and lactic-to-glycolic acid ratios; polyethylene glycol-polypropylene glycol block copolymers of any number and combination of repeating units such as PLURONIC® block copolymers, TETRONIC® block copolymers, or GENAPOL® block copolymers, combination of the above copolymers either physically or chemically linked units, e.g., PEG-PLA or PEG-PLGA copolymer mixtures. The bioadhesive material may be selected from polyethylene glycols, polyoxyethylenes, polyacrylic acid polymers, such as CARBOPOL® polymers (such as CARBOPOL® 71G, 934P, 971P 974P) and polycarbophils (such as NOVEON® AA-1, CA-1, and CA-2 polycarbophils), cellulose and its derivatives, polyethylene glycol, CARBOPOL® polymers, and/or a cellulosic derivative or combination; a soluble polyvinylpyrrolidone polymer (PVP), a carbomer homopolymer, a carbomer copolymer, one or more maltodextrin, alginate, a cross-linked alginate gum gel, a water-swellable but water-insoluble fibrous cross-linked carboxy-functional polymer, a hydrophilic polysaccharide gum, thiomers e.g., thiolated chitosan, thiolated polycarbophil, thiolated alginate, thiolated cellulose derivatives, thiolated carboxymethyl cellulose, thiolated polyacrylic acid, or thiolated polyacrylates; lectin, hydroxypropyl methyl cellulose (HPMC), cellulose derivatives, HPMA copolymers, a water-dispersible polycarboxylated vinyl polymer, cationic polymers, non-ionic polymers, or anionic polymers. Cationic polymers include but are not limited to chitosan (Wella "low viscosity"), chitosan (Wella "high viscosity"), chitosan (Dr. Knapczyk), daichitosan H, daichitosan VH, Sea Cure 240, Sea Cure 210+, chitosan (Sigma), Polycarbophil/Diachitosan VH blend, DEAE-dextran, and aminodextran. Non-ionic polymers include but are not limited to Scleroglucan, Hestarch, and HPC. Anionic polymers include but are not limited to carboxymethylcellulose (CMC) low, medium, or high viscosity), pectin, xanthan gum, and/or polycarbophil. In one embodiment the mucoadhesive agent is a CARBOPOL® polymer and/or a cellulosic derivative.

Chitosan, due to its mucoadhesive character (Lehr et al. 1992) and favorable toxicological properties, is an absorption enhancer across intestinal epithelia. Chitosan glutamate reduced transepithelial electrical resistance (TEER) in vitro of a cultured intestinal epithelial cell line (Caco-2) (Borchard et al., 1996) and increased the transport of hydrophilic molecules such as [$^{14}$C]mannitol, molecular weight (MW) 182.2 and a fluorescein-dextran (MW 4400) significantly in Caco-2 cell monolayers (Artursson et al. 1994; Borchard et al., 1996; Schipper et al., 1996). Similarly, transport of the peptide drug 9-desglycinamide, 8-arginine vasopressin (DGAVP, MW 1412) increased markedly after coadministration with chitosan glutamate in Caco-2 cell monolayers (Luessen et al. 1997). Chitosan salts such as chitosan glutamate and chitosan hydrochloride are used in vivo as absorption enhancers for peptide drugs. Nasal application of insulin with chitosan glutamate significantly reduced blood glucose levels of rats and sheep (Ilium et al. 1994), and intraduodenal application of buserelin (MW 1299.5) and chitosan hydrochloride in a gel formulation increased the absolute bioavailability of buserelin from 0.1±0.1 to 5.1±1.5% (Luessen et al. 1996a). These increases in absorption could be attributed to the effect of chitosan on the integrity of the epithelial tight junctions. Tight junctions play a crucial part in maintaining the selective barrier function of cell membranes and in sealing cells together to form a continuous cell layer through which even small molecules cannot penetrate. However, tight junctions are permeable to water, electrolytes, and other charged or uncharged molecules up to a certain size (Madara 1989; Wilson and Washington 1989). Tight junctions are known to respond to changes in calcium concentrations, cyclic AMP (cAMP), osmolarity, pH, and the status of the cytoskeleton (Cereijido et al., 1993).

Chitosan salts are proposed to open tight junctions in a concentration- and pH-dependent way to allow paracellular transport of large hydrophilic compounds. The increase in the transport of these compounds could be attributed to an interaction of a positively charged amino group on the C-2 position of chitosan with negatively charged sites on the cell membranes and tight junctions of the mucosal epithelial cells to allow opening of the tight junctions. It is known that chitosan glutamate induces changes in F-actin distribution (Artursson et al. 1994). It is also known that pharmacological agents that interact with cytoskeletal F-actin simultaneously increase paracellular permeability (Meza et al. 1982). This agrees with the hypothesis that F-actin is directly or indirectly associated with the proteins in the tight junctions such as ZO-1 (Madara 1987). Schipper et al. (1997) have shown that chitosan induces a redistribution of cytoskeletal F-actin and the tight junction protein ZO-1. Confocal laser scanning microscopy has confirmed that chitosan is able to open the tight junctions to allow paracellular transport of large hydrophilic compounds (Borchard et al. 1996; Schipper et al. 1997). Mucoadhesion may play an additional role in this process by increasing the residence time of the drugs on the cell surfaces.

In embodiments, the mucoadhesive/bioadhesive excipient is typically present in a range of about 1% to about 50% w/w, or in a range of about 1% to about 40% w/w, or in a range of about 2 to about 30% w/w. A single mucoadhesive or bioadhesive or combinations may be used. Bioadhesion increases residence time of a dosage form at the absorption site, and thereby may result in increased drug bioavailability. Use of a mucoadhesive facilitates prolonged contact between the pharmaceutical composition and the oral mucus membrane. Upon contact of the pharmaceutical composition with the mucus membrane, moisture in the mucus plasticizes the mucoadhesive, which may then consolidate with the mucus membrane by forming weak bonds with the glycoproteins in the mucus and/or mechanically interlocking with the glycoproteins and lipids in the mucus. The mucoadhesive may increase the residence time of contact of the pharmaceutically active agent and the absorption surface and may facilitate absorption of the pharmaceutically active agents by the absorption surface.

Aspects

Aspect 1. A deuterated domperidone formulation comprising domperidone-$d_4$ in an oral dosage formulation.

Aspect 2. The formulation of Aspect 1 where a deuterated domperidone solution or suspension is in a softgel, capsule, or tablet to result in a unit dose.

Aspect 3. A deuterated domperidone formulation comprising domperidone-$d_4$ in a liquid filled capsule containing excipients selected from the group consisting of lipids, fatty acids, surfactants, solvents, and combinations thereof.

Aspect 4. A compound selected from the group consisting of formula 1 where at least one hydrogen atom is replaced by a deuterium atom with the proviso that six propyl hydrogen atoms are not replaced, compound 2, compound 3, compound 4, compound 5, and combinations thereof.

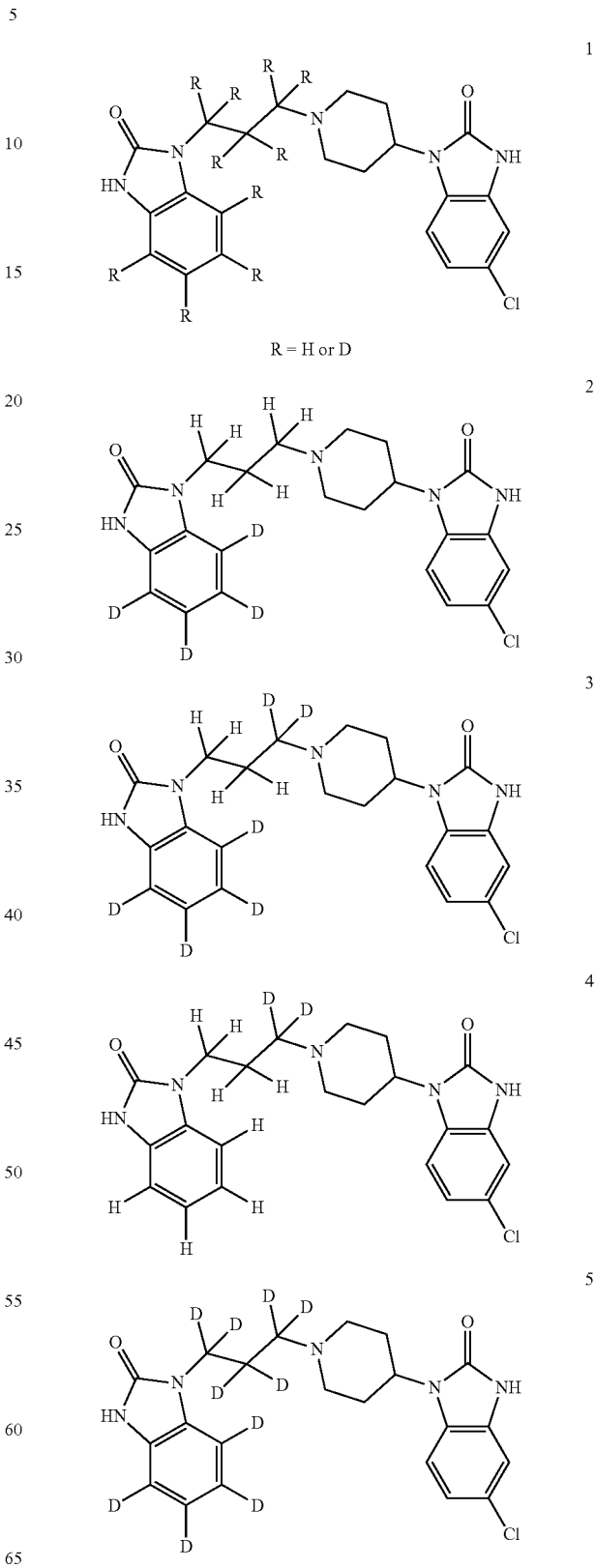

Aspect 5. A method of making a compound of Aspect 4, the method comprising reacting 1,2-diaminobenzene having 0 to 4 deuteriums with a reactive carbonyl species to produce a cyclic imide;

reacting the cyclic imide with a protecting group to produce a monoprotected cyclic imide;

reacting the monoprotected cyclic imide with a 1,3-bifunctional propyl derivative having 0 to 6 deuteriums to produce an intermediate;

reacting the intermediate with 5-chloro-1-(4-piperidinyl)-1,3-dihydro-2H-benzimidazol-2-one; and removing the protecting group either before or after reacting the intermediate with the 5-chloro-1-(4-piperidinyl)-1,3-dihydro-2H-benzimidazol-2-one.

Aspect 6. A domperidone formulation comprising domperidone-d$_4$ in a liquid filled capsule containing excipients selected from the group consisting of lipids, fatty acids, surfactants, solvents, and combinations thereof.

Aspect 7. A method of making compound 1 according to Scheme 1,

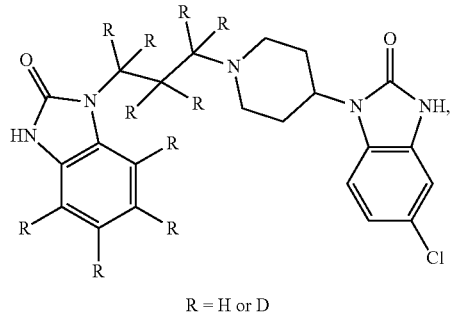

R = H or D the method comprising reacting 1,2-diaminobenzene having 0 to 4 deuteriums with a reactive carbonyl species to produce a cyclic imide;

reacting the cyclic imide with a protecting group to produce a monoprotected cyclic imide;

reacting the monoprotected cyclic imide with a 1,3-bifunctional propyl derivative having 0 to 6 deuteriums to produce an intermediate;

reacting the intermediate with 5-chloro-1-(4-piperidinyl)-1,3-dihydro-2H-benzimidazol-2-one; and removing the protecting group either before or after reacting the intermediate with the 5-chloro-1-(4-piperidinyl)-1,3-dihydro-2H-benzimidazol-2-one, where the 1,2-diaminobenzene has at least one deuterium or the 1,3-bifunctional propyl derivative has at least one deuterium or both the 1,2-diaminobenzene and the 1,3-bifunctional propyl derivative each have at least one deuterium.

Aspect 8. A method of making a deuterated domperidone compound of Aspect 4, the method comprising reacting 1,2-diaminobenzene having 0-4 deuteriums with a reactive carbonyl species to produce a cyclic imide;

reacting the cyclic imide with a protecting group to produce a monoprotected cyclic imide;

reacting the monoprotected cyclic imide with a 1,3-bifunctional propyl derivative having 0-5 deuteriums to produce an intermediate;

reacting the intermediate with 5-chloro-1-(4-piperidyl)-1H-benzimidazol-2(3H)-one; and removing the protecting group either before or after reacting the intermediate with the 5-chloro-1-(4-piperidyl)-1H-benzimidazol-2(3H)-one;

where the 1,2-diaminobenzene has at least one deuterium or the 1,3-bifunctional propyl derivative has at least one deuterium or both the 1,2-diaminobenzene and the 1,3-bifunctional propyl derivative each have at least one deuterium.

Aspect 9. A method of making deuterated domperidone Compound 1 according to Scheme 2,

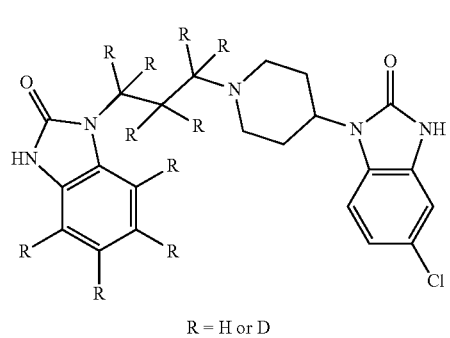

R = H or D the method comprising reacting 1,2-diaminobenzene having 0-4 deuteriums with tetraethyl orthocarbonate to produce a protected cyclic imide;

reacting the protected cyclic imide with a 1,3-bifunctional propyl derivative having 0-6 deuteriums to produce an intermediate; and reacting the intermediate with 5-chloro-1-(4-piperidyl)-1H-benzimidazol-2(3H)-one.

Aspect 10. A method of making deuterated domperidone Compound 2 according to Scheme 1,

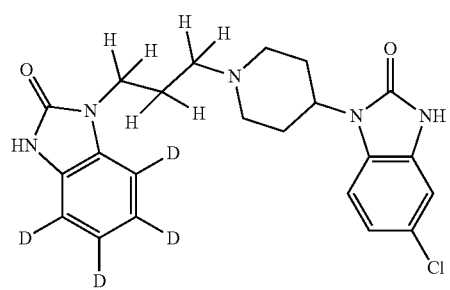

the method comprising reacting 1,2-diaminobenzene having 4 deuteriums with a reactive carbonyl species to produce a cyclic imide;

reacting the cyclic imide with a protecting group to produce a monoprotected cyclic imide;

reacting the monoprotected cyclic imide with a 1,3-bifunctional propyl derivative to produce an intermediate;

reacting the intermediate with 5-chloro-1-(4-piperidyl)-1H-benzimidazol-2(3H)-one; and removing the protecting group either before or after reacting the intermediate with the 5-chloro-1-(4-piperidinyl)-1,3-dihydro-2H-benzimidazol-2-one.

Aspect 11. A method of making deuterated domperidone Compound 2 according to Scheme 2, the method comprising reacting 1,2-diaminobenzene having 4 deuteriums with tetraethyl orthocarbonate to produce a protected cyclic imide;

reacting the protected cyclic imide with a 1,3-bifunctional propyl derivative to produce an intermediate; and reacting the intermediate with 5-chloro-1-(4-piperidyl)-1H-benzimidazol-2(3H)-one.

Aspect 12. A 1-(3-chloropropyl)-4,5,6,7-tetradeutero-2-ethoxy-benzimidazole compound of formula 16 where R=H or D.

Aspect 13. A 1-(3-chloropropyl)-4,5,6,7-tetradeutero-2-ethoxy-benzimidazole compound of formula 16 where R=D.

Aspect 14. The compound of Aspect 13 containing four deuterium atoms.

Aspect 15. A therapeutic method comprising administering to a patient in need thereof deuterated domperidone or a pharmaceutically acceptable salt thereof to ameliorate a disorder, the disorder selected from the group consisting of gastroparesis, nausea apart from gastroparesis, vomiting apart from gastroparesis, nausea associated with gastroparesis, vomiting associated with gastroparesis, gastroesophageal reflux disease, insufficient lactation, and combinations thereof, with the proviso that the deuterated domperidone is not compound 6.

Aspect 16. The method of Aspect 15 where administering a $d_4$ deuterated form of domperidone reduces domperidone metabolism to a greater extent than a $d_6$ deuterated form of domperidone.

Aspect 17. The method of Aspect 15 where a route of administration reduces domperidone metabolism.

Aspect 18. The method of Aspect 15 where a formulation of deuterated domperidone increases domperidone bioavailability.

Aspect 19. The method of Aspect 15 where the compounds administered are selected from the group consisting of compounds 2, compound 3, compound 4, compound 5, and combinations thereof.

Aspect 20. The method of Aspect 15 where deuterated domperidone is administered by transdermal administration.

Aspect 21. The method of Aspect 15 where deuterated domperidone is administered by a route of administration selected from the group consisting of oral administration, transdermal administration, parenteral administration, and combinations thereof.

Aspect 22. The method of Aspect 21 where deuterated domperidone is administered orally in a formulation selected from the group consisting of a tablet, a capsule, a softgel, a liquid, and combinations thereof.

Aspect 23. The method of Aspect 15 where deuterated domperidone is administered in the range between 0.5 mg to 120 mg.

Aspect 24. The method of Aspect 15 where deuterated domperidone is administered in the range between 0.05% to 12.0%.

Aspect 25. The method of Aspect 15 where deuterated domperidone is administered in the range between 0.07 mg/kg to 1.71 mg/kg.

Aspect 26. The method of Aspect 15 where deuterated domperidone is administered in the range between 1 mg to 60 mg.

Aspect 27. The method of Aspect 15 where deuterated domperidone is administered in the range between 0.1% to 6.0%.

Aspect 28. The method of Aspect 15 where deuterated domperidone is administered in the range between 0.014 mg/kg to 0.86 mg/kg.

Aspect 39. The method of Aspect 15 where deuterated domperidone is administered in the range between 2.0 mg to 40 mg.

Aspect 30. The method of Aspect 15 where deuterated domperidone is administered in the range between 0.2% to 4.0%.

Aspect 31. The method of Aspect 15 where deuterated domperidone is administered in the range between 0.028 mg/kg to 0.57 mg/kg.

Aspect 32. The method of Aspect 15 where deuterated domperidone ameliorates gastroparesis in the patient.

Aspect 33. The method of Aspect 15 where deuterated domperidone ameliorates at least one of nausea or vomiting as a separate disorder apart from nausea or vomiting as a result of gastroparesis in the patient.

Aspect 34. The method of Aspect 15 where domperidone administration is selected from the group consisting of an increased surface area form, a transdermal route, a lipid-based oral route, and combinations thereof.

Aspect 35. A method to facilitate treatment of a disease in a patient, the method comprising administering to a patient in need thereof deuterated domperidone under conditions that reduce domperidone metabolism relative to conditions resulting in normal domperidone metabolism and/or increases domperidone bioavailability, with the proviso that the deuterated domperidone is not compound 6.

Aspect 36. The method of Aspect 35 where administering a $d_4$ deuterated form of domperidone reduces domperidone metabolism to a greater extent than a $d_6$ deuterated form of domperidone.

Aspect 37. The method of Aspect 35 where a route of administration reduces domperidone metabolism.

Aspect 38. The method of Aspect 35 where a formulation of deuterated domperidone increases domperidone bioavailability.

Aspect 39. The method of Aspect 35 where the compounds administered are selected from the group consisting of compounds 2, compound 3, compound 4, compound 5, and combinations thereof.

Aspect 40. The method of Aspect 35 where deuterated domperidone is administered by transdermal administration.

Aspect 41. The method of Aspect 35 where deuterated domperidone is administered by a route of administration selected from the group consisting of oral administration, transdermal administration, parenteral administration, and combinations thereof.

Aspect 42. The method of Aspect 39 where deuterated domperidone is administered orally in a formulation selected from the group consisting of a tablet, a capsule, a softgel, a liquid, and combinations thereof.

Aspect 43. The method of Aspect 35 where increased surface area of a particulate formulation of deuterated domperidone increases domperidone bioavailability.

Aspect 44. The method of Aspect 35 where deuterated domperidone is administered in the range between 0.5 mg to 120 mg.

Aspect 45. The method of Aspect 35 where deuterated domperidone is administered in the range between 0.05% to 12.0%.

Aspect 46. The method of Aspect 35 where deuterated domperidone is administered in the range between 0.07 mg/kg to 1.71 mg/kg.

Aspect 47. The method of Aspect 35 where deuterated domperidone is administered in the range between 1 mg to 60 mg.

Aspect 48. The method of Aspect 35 where deuterated domperidone is administered in the range between 0.1% to 6.0%.

Aspect 49. The method of Aspect 35 where deuterated domperidone is administered in the range between 0.014 mg/kg to 0.86 mg/kg.

Aspect 50. The method of Aspect 35 where deuterated domperidone is administered in the range between 2.0 mg to 40 mg.

Aspect 51. The method of Aspect 35 where deuterated domperidone is administered in the range between 0.2% to 4.0%.

Aspect 52. The method of Aspect 35 where deuterated domperidone is administered in the range between 0.028 mg/kg to 0.57 mg/kg.

Aspect 53. The method of Aspect 35 where domperidone ameliorates gastroparesis in the patient.

Aspect 54. The method of Aspect 35 where domperidone ameliorates at least one of nausea or vomiting as a separate disorder apart from nausea or vomiting as a result of gastroparesis in the patient.

Aspect 55. The method of Aspect 35 where domperidone administration is selected from the group consisting of an increased surface area form, a transdermal route, a lipid-based oral route, and combinations thereof.

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

The following examples are not limiting. Examples 1-5 are according to synthesis Scheme 1. Examples 6-8 are according to synthesis Scheme 2.

From synthesis scheme 1

Example 1: Preparation of 2,3-dihydro(4,5,6,7-$D_4$)-1H-1,3-benzodiazol-2-one

A 100 mL round-bottomed flask equipped with a stir bar and nitrogen in/outlet was charged with ($D_4$)benzene-1,2-diamine (1 eq, 2 g, 17.83 mmol) and 30 ml of dry DMF then agitated under nitrogen to dissolve before charging 1-(1H-imidazole-1-carbonyl)-1H-imidazole (1 eq, 2.89 g, 17.83 mmol) and stirring at RT for 22 h. The solvent was evaporated under vacuum to afford a yellow dense oil which was diluted in a minimal amount of dichloromethane (DCM) to crystallize. The desired solid was collected by vacuum filtration, washed with DCM and dried under vacuum to yield 2.09 g (15.13 mmol, 85%) of the desired product.

Example 2: Preparation of tert-butyl 2-oxo-2,3-dihydro(4,5,6,7-$D_4$)-1H-1,3-benzodiazole-1-carboxylate To a 100 mL three-neck round-bottomed flask equipped with a stir bar and nitrogen in/outlet was charged 2,3-dihydro(4,5,6,7-$D_4$)-1H-1,3-benzodiazol-2-one (1 eq, 2.09 g, 15.13 mmol) and 40 ml of dry DMF. To this stirred solution, sodium hydride (1.1 eq, 197 mg, 8.200 mmol) was added portion-wise and the reaction was left under the same conditions for 1.5 h. After this period, di-tert-butyl dicarbonate (1 eq, 3.30 g, 15.13 mmol), dissolved in 8 ml of dry DMF, was added dropwise and left to react for 3 h. The reaction was complete and it was treated with a saturated solution of $NH_4Cl$, followed by dilution with $H_2O$ and extraction with 4×50 ml of EtOAc. The organic fractions were combined, dried over $Na_2SO_4$, filtered and concentrated to dryness under vacuum. The crude material thus obtained was purified through a silica gel chromatography (Biotage ISOLERA™, KP-Sil 50 g cartridge, eluting with a gradient of Cy:EtOAc from 90:10 to pure AcOEt) to yield 3.134 g (13.15 mmol, 87%) of desired compound.

Example 3: Preparation of tert-butyl 3-(3-chloropropyl)-2-oxo-2,3-dihydro($D_4$)-1H-1,3-benzodiazole-1-carboxylate To a three-necked round-bottomed flask was charged tert-butyl 2-oxo-2,3-dihydro-1H-1,3-benzodiazole-1-carboxylate (1 eq, 3.134 g, 13.15 mmol) in 60 ml of dry DMF and stirred at room temperature. To this solution, potassium carbonate (3 eq, 5.452 g, 39.45 mmol) was added portion-wise and left under the same conditions for 30 minutes. After this, 1-bromo-3-chloropropane (1 eq, 1.300 ml, 13.15 mmol) was added to the solution and stirred at room temperature overnight. The reaction was then quenched by diluting with ethyl acetate (EtOAc) and $H_2O$. The layers were separated and the aqueous phase was extracted with 3×25 ml of EtOAc and the organic layers were combined, washed with brine, dried over $Na_2SO_4$, filtered and concentrated to dryness under vacuum. The crude material, thus obtained, was purified using a silica gel chromatography (Biotage ISOLERA™, KP-Sil 50 g cartridge, eluting with a gradient of Cy:EtOAc from 90:10 to Cy:EtOAc from 1:1) to give the desired compound (3.929 g, 12.48 mmol, 95%).

Example 4: Preparation of 1-(3-iodopropyl)-2,3-dihydro(4,5,6,7-$D_4$)-1H-1,3-benzodiazol-2-one A 250 mL round-bottomed flask was charged with tert-butyl 3-(3-chloropropyl)-2-oxo-2,3-dihydro($D_4$)-1H-1,3-benzodiazole-1-carboxylate (1 eq, 3.929 g, 12.48 mmol), dissolved in 100 ml of acetonitrile, and stirred at room temperature. Sodium iodide (4.5 eq, 8.417 g, 56.16 mmol) was added portion-wise and the reaction was refluxed overnight. After cooling to room temperature the reaction was filtered and the solvent was removed under vacuum. The crude material, thus obtained, was purified with a silica gel chromatography (Biotage ISOLERA™KP-Sil 100 g cartridge, eluting with a gradient from pure DCM to pure DCM:MeOH/1:1) to give the desired compound (3.631 g, 11.86 mmol, yield=95%).

Example 5: Preparation of 1-{3-[4-(5-chloro-2-oxo-2,3-dihydro-1H-1,3-benzodiazol-1-yl)piperidin-1-yl]propyl}-2,3-dihydro(4,5,6,7-$D_4$)-1H-1,3-benzodiazol-2-one (Compound 2)

A 500 mL round-bottomed flask was charged with 5-chloro-1-(4-piperidyl)-1H-benzimidazol-2(3H)-one (1.2 eq, 3.582 g, 14.23 mmol) then dissolved in 250 ml of dry THF and 25 ml of dry DMF. This solution was stirred under nitrogen at room temperature and a solution of 1-(3-iodopropyl)-2,3-dihydro(4,5,6,7-$D_4$)-1H-1,3-benzodiazol-2-one (1 eq, 3.631 g, 11.86 mmol) in 120 ml of dry THF was added drop-wise over 10 minutes. The resulting yellow solution was stirred for 2 h before charging potassium carbonate (1.5 eq, 2.458 g, 17.79 mmol) and stirring at RT for 48 h until the yellow color disappeared. The reaction was filtered and the solid was washed with EtOAc and the filtrate was concentrated to dryness under vacuum. The crude material thus obtained was passed through a silica gel chromatography (Biotage ISOLERA™, KP-Sil 340 g cartridge, eluting with a gradient of DCM:MeOH from 98:2 to DCM:MeOH/1:1). At the end of the purification process, 3.245 g (7.45 mmol, 64%) of desired compound 2 was obtained as a white crystalline solid.

From synthesis scheme 2

Example 6: Preparation of 4,5,6,7-tetradeutero-2-ethoxy-1H-benzimidazole (Compound 15)

To a round-bottomed flask equipped with a stir bar, thermocouple, condenser and nitrogen in/outlet was charged 6.5 g (58 mmol, 1 eq) of 2-amino-3,4,5,6-tetradeuteroaniline, which was suspended in 13.3 mL (12.25 g, 63 mmol, 1.1 eq) of tetraethyl orthocarbonate and 0.3 mL (0.35 g, 5.8 mmol, 0.1 eq) of acetic acid. Absolute ethanol 19.5 mL was added to the suspension, and the resultant mixture was heated to reflux where it was stirred for one hour until complete by HPLC analysis. The orange solution was distilled to remove 20.5 mL of ethanol before a solution of 13 mL of saturated sodium carbonate and 26 mL of water was added at just below reflux to precipitate the product. Once addition was complete the suspension was cooled to room temperature where the solid was collected by vacuum filtration. The resultant wet-cake was washed with water (26 mL), then dried in a vacuum oven overnight at 50° C. to yield 9.34 g (97.4%) of the desired product, with >99.5% purity by HPLC.

Example 7: Preparation of 1-(3-chloropropyl)-4,5,6,7-tetradeutero-2-ethoxy-benzimidazole (Compound 16)

To a round-bottomed flask equipped with a stir bar, nitrogen in/outlet and condenser was charged 9.2 g (55.3 mmol, 1.0 eq) of Compound 15, potassium carbonate (15.3 g, 110.1 mmol, 2.0 eq), 1-bromo-3-chloro-propane (8.21 mL, 83.1 mmol, 1.5 eq) and 55 mL of methyl isobutyl ketone (MIBK). The resultant suspension was heated to reflux and stirred for 3 h until complete by HPLC analysis. After cooling to room temperature, 36.8 mL of water was added and the mixture stirred to dissolve salts before separating the phases. The aqueous layer was extracted with MIBK (1×36.8 mL), the organic layers were combined then concentrated to an oil. MIBK (36.8 mL) was added to the oil and concentrated again. This procedure was repeated until 1H NMR analysis indicated <1 mol % 1-bromo-2-chloropropane remaining. This oil was then used directly in the next step.

Example 8: Preparation of 1-{3-[4-(5-chloro-2-oxo-2,3-dihydro-1H-1,3-benzodiazol-1-yl)piperidin-1yl]propyl}-2,3-dihydro(4,5,6,7-D4)-1H-1,3-benzodiazol-2-one (Compound 2)

A 0.5 L jacketed reactor equipped with a mechanical stirrer, thermocouple, and condenser under a nitrogen atmosphere was charged with 5-chloro-1-(4-piperidyl)-1H-benzimidazol-2(3H)-one (Compound 14, 13.8 g, 54.9 mmol, 1.0 eq), potassium iodide (9.1 g, 54.9 mmol, 1.0 eq), potassium bicarbonate (5.5 g, 54.9 mmol, 1.0 eq) and 60 mL of water. To this stirred suspension was charged a solution of 13.33 g (54.9 mmol, 1.0 eq) of compound 16 in 60 mL of isopropanol. After heating to reflux with a jacket temperature of 105° C. the reaction was stirred at this temperature for 18 h until complete by HPLC analysis. An additional 30 ml of water and 30 mL of isopropanol was added and reflux continued for 20 min to dissolve solids, before adding 36 ml of 4M HCl (144 mmol, 2.6 eq) to the refluxing mixture. Reflux was continued for 2 h until the deprotection was complete. While still at reflux the batch was quenched to pH 11 with 12 M sodium hydroxide. Product precipitation was observed and completed by cooling the batch to 15° C. and then collecting the solid by vacuum filtration. The wet-cake was washed with water (3×51 mL), then dried under vacuum to give 20.37 g (86.3%) of desired product with 94.5% purity. Purity could be improved to >97% by recrystallization from DMSO/water or trituration with IPA/water or MeOH/water.

Example 9: Comparison of Deuterated and Nondeuterated Domperidone

Figure 22A:
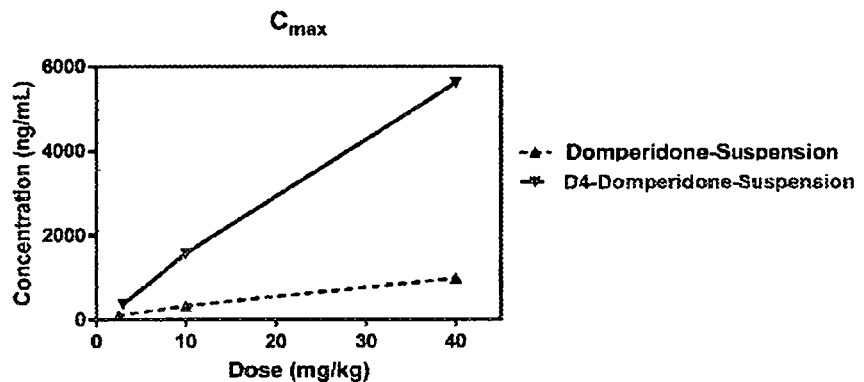
FIGS. 22A-22B are line graphs showing the effect of domperidone or $d_4$-domperidone suspensions on $C_{max}$ and AUC, respectively.
Figure 22B:
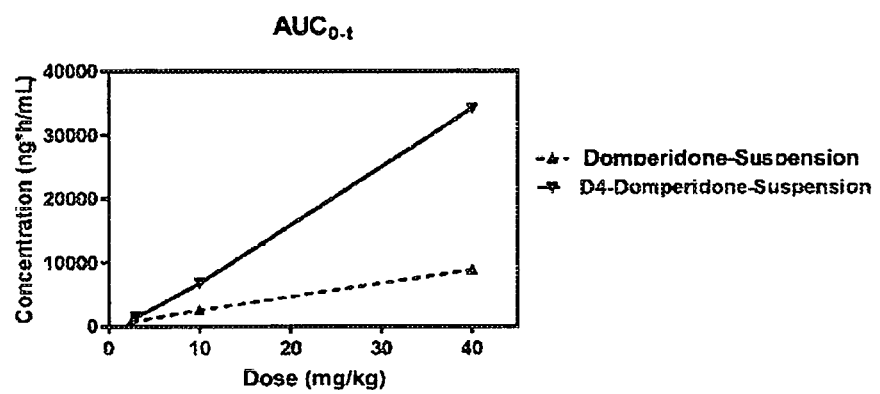

In this example, the activity of domperidone and $d_4$-domperidone were compared. In summary, the oral exposure of domperidone and deuterated domperidone ($d_4$-domperidone) was evaluated in Beagle dogs following oral administration of suspension formulations containing domperidone or $d_4$-domperidone and 0.5% methocel, 0.2% polysorbate 80, and 0.72% lactic acid. Each compound was dosed orally at 3 mg/kg, 10 mg/kg and 40 mg/kg. Blood samples were collected up to 24 hours post-dose, and plasma concentrations of domperidone were determined by LCMS/MS. Pharmacokinetic parameters were determined using Phoenix WinNonlin (v7.0). See, FIGS. 22A and 22B.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. Each of the references cited are expressly incorporated by reference herein in its entirety.

What is claimed is:
1. A method for ameliorating gastroesophageal reflux disease, functional dyspepsia, or nausea and vomiting associated with chemotherapy, in a patient, comprising administering a therapeutically effective amount of a compound that is $d_2$-domperidone 4, $d_4$-domperidone 2, $d_6$-domperidone 3, or $d_{10}$-domperidone 5, or a pharmaceutically acceptable salt thereof to the patient:

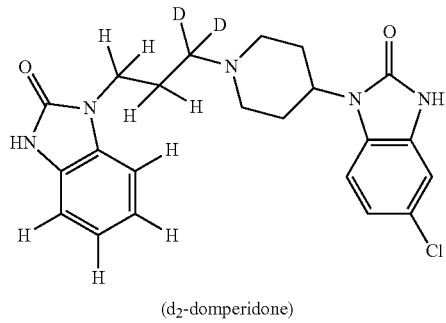

(d₂-domperidone)

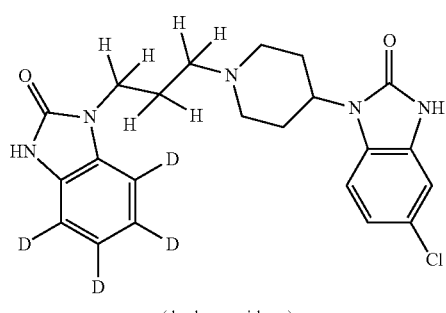

(d₄-domperidone)

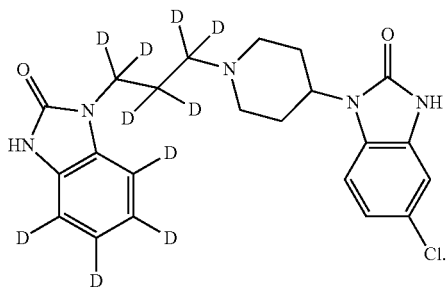

(d₆-domperidone)

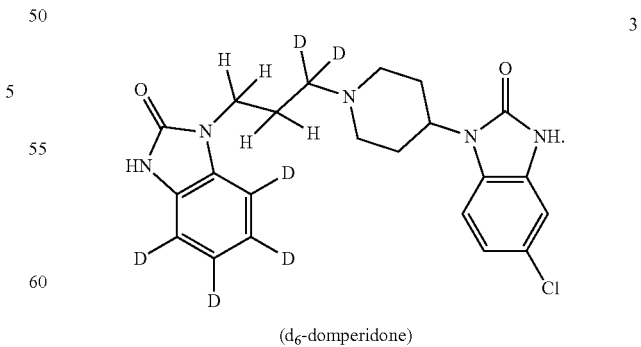

(d₁₀-domperidone)

2. The method of claim 1, wherein the compound is d₂-domperidone 4 or a pharmaceutically acceptable salt thereof:

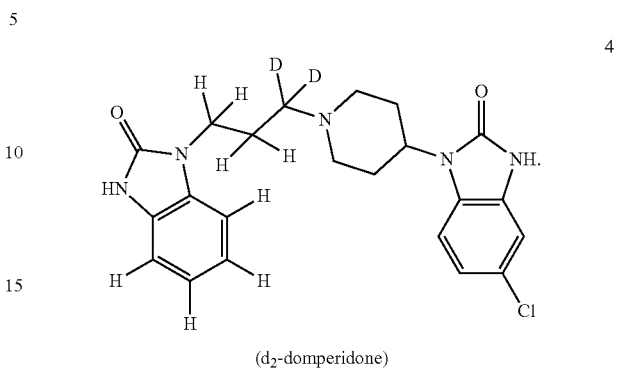

(d₂-domperidone)

3. The method of claim 1, wherein the compound is d₄-domperidone 2 or a pharmaceutically acceptable salt thereof:

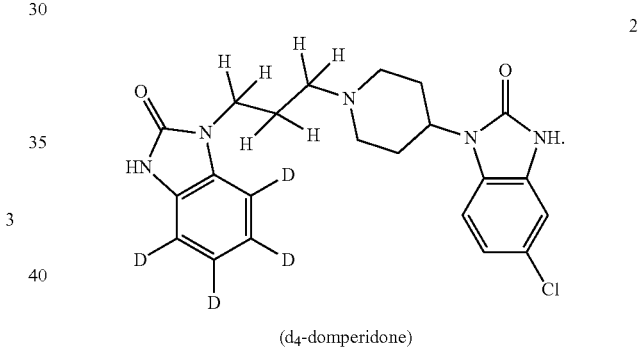

(d₄-domperidone)

4. The method of claim 1, wherein the compound is d₆-domperidone 3 or a pharmaceutically acceptable salt thereof:

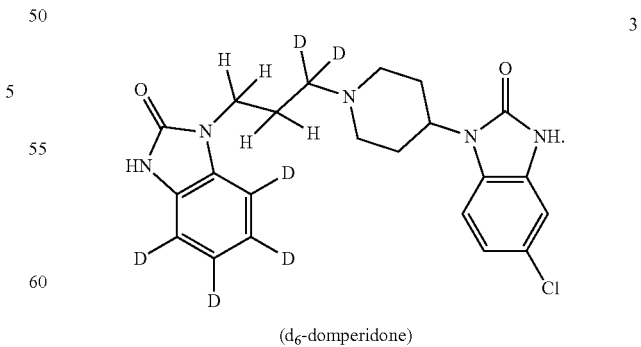

(d₆-domperidone)

5. The method of claim 1, wherein the compound is d₁₀-domperidone 5 or a pharmaceutically acceptable salt thereof:

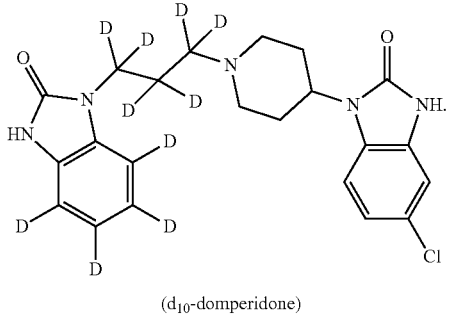

($d_{10}$-domperidone)

6. The method of claim 1, wherein the deuterated domperidone is administered orally, transdermally, parenterally, or a combination thereof.

7. The method of claim 6, where the deuterated domperidone is administered orally.

8. The method of claim 1, wherein the therapeutically effective amount is in the range of 0.1 mg to 120 mg.

9. The method of claim 8, wherein the therapeutically effective amount is in the range of 1 mg to 60 mg.

10. The method of claim 9, wherein the therapeutically effective amount is in the range of 2.0 mg to 40 mg.

11. The method of claim 1, wherein the therapeutically effective amount is in the range of 0.01% to 12.0% w/w.

12. The method of claim 11, wherein the therapeutically effective amount is in the range of 0.1% to 6.0% w/w.

13. The method of claim 12, wherein the therapeutically effective amount is in the range of 0.2% to 4.0% w/w.

14. The method of claim 1, wherein the therapeutically effective amount is in the range of 0.0014 mg/kg to 1.71 mg/kg.

15. The method of claim 14, wherein the therapeutically effective amount is in the range of 0.014 mg/kg to 0.86 mg/kg.

16. The method of claim 15, wherein the therapeutically effective amount is in the range of 0.028 mg/kg to 0.57 mg/kg.

17. The method of claim 1, for ameliorating gastroesophageal reflux disease.

18. The method of claim 1, for ameliorating functional dyspepsia.

19. The method of claim 1, for ameliorating nausea and vomiting associated with chemotherapy.

* * * * *